(12) United States Patent
Swensgard

(10) Patent No.: US 9,198,661 B2
(45) Date of Patent: Dec. 1, 2015

(54) STAPLING INSTRUMENT COMPRISING A PLURALITY OF STAPLE CARTRIDGES STORED THEREIN

(75) Inventor: Brett E. Swensgard, West Chester, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 370 days.

(21) Appl. No.: 13/225,850

(22) Filed: Sep. 6, 2011

(65) Prior Publication Data

US 2013/0056518 A1     Mar. 7, 2013

(51) Int. Cl.
*A61B 17/072*     (2006.01)

(52) U.S. Cl.
CPC ..... *A61B 17/07207* (2013.01); *A61B 17/07292* (2013.01); *A61B 2017/07271* (2013.01)

(58) Field of Classification Search
CPC . A61B 17/068; A61B 17/072; A61B 17/1155
USPC ...................... 227/175.1, 176.1, 178.1, 180.1; 606/139, 153, 219
See application file for complete search history.

(56) References Cited

U.S. PATENT DOCUMENTS

| | | | |
|---|---|---|---|
| 2,853,074 A | 9/1958 | Olson | |
| 3,166,072 A | 1/1965 | Sullivan, Jr. | |
| 3,490,675 A | 1/1970 | Green et al. | |
| 3,494,533 A | 2/1970 | Green et al. | |
| 3,551,987 A | 1/1971 | Wilkinson | |
| 3,643,851 A | 2/1972 | Green et al. | |
| 3,650,453 A | 3/1972 | Smith, Jr. | |
| 3,662,939 A | 5/1972 | Bryan | |
| 3,717,294 A | 2/1973 | Green | |
| 3,819,100 A | 6/1974 | Noiles et al. | |
| RE28,932 E | 8/1976 | Noiles et al. | |
| 4,127,227 A | 11/1978 | Green | |
| 4,198,982 A | 4/1980 | Fortner et al. | |
| 4,207,898 A | 6/1980 | Becht | |
| 4,331,277 A | 5/1982 | Green | |
| 4,383,634 A | 5/1983 | Green | |
| 4,396,139 A | 8/1983 | Hall et al. | |
| 4,402,445 A | 9/1983 | Green | |
| 4,415,112 A | 11/1983 | Green | |

(Continued)

FOREIGN PATENT DOCUMENTS

| AU | 2012200178 B2 | 7/2013 |
|---|---|---|
| CA | 2458946 A1 | 3/2003 |

(Continued)

OTHER PUBLICATIONS

Disclosed Anonymously, "Motor-Driven Surgical Stapler Improvements," Research Disclosure Database No. 526041, Published: Feb. 2008.

(Continued)

*Primary Examiner* — Hemant M Desai
*Assistant Examiner* — Nathaniel Chukwurah

(57) ABSTRACT

A surgical stapling instrument can comprise an end effector configured to receive a staple cartridge, a shaft including a plurality of staple cartridges positioned therein, and a staple cartridge driver configured to sequentially advance the staple cartridges from the shaft into the end effector. In various embodiments, the staple cartridges can comprise different configurations which can be arranged within the shaft such that they are supplied in a specific predetermined order.

20 Claims, 20 Drawing Sheets

(56) References Cited

U.S. PATENT DOCUMENTS

| | | |
|---|---|---|
| 4,429,695 A | 2/1984 | Green |
| 4,475,679 A | 10/1984 | Fleury, Jr. |
| 4,489,875 A | 12/1984 | Crawford et al. |
| 4,500,024 A | 2/1985 | DiGiovanni et al. |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,522,327 A | 6/1985 | Korthoff et al. |
| 4,530,453 A | 7/1985 | Green |
| 4,566,620 A | 1/1986 | Green et al. |
| 4,573,468 A | 3/1986 | Conta et al. |
| 4,573,622 A | 3/1986 | Green et al. |
| 4,580,712 A | 4/1986 | Green |
| 4,605,004 A | 8/1986 | Di Giovanni et al. |
| 4,610,383 A | 9/1986 | Rothfuss et al. |
| 4,619,262 A | 10/1986 | Taylor |
| 4,629,107 A | 12/1986 | Fedotov et al. |
| 4,632,290 A | 12/1986 | Green et al. |
| 4,655,222 A | 4/1987 | Florez et al. |
| 4,664,305 A | 5/1987 | Blake, III et al. |
| 4,671,445 A | 6/1987 | Barker et al. |
| 4,715,520 A | 12/1987 | Roehr, Jr. et al. |
| 4,728,020 A | 3/1988 | Green et al. |
| 4,752,024 A | 6/1988 | Green et al. |
| 4,754,909 A | 7/1988 | Barker et al. |
| 4,767,044 A | 8/1988 | Green |
| 4,773,420 A | 9/1988 | Green |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,844,068 A | 7/1989 | Arata et al. |
| 4,848,637 A | 7/1989 | Pruitt |
| 4,869,414 A | 9/1989 | Green et al. |
| 4,869,415 A | 9/1989 | Fox |
| 4,893,622 A | 1/1990 | Green et al. |
| 4,903,697 A | 2/1990 | Resnick et al. |
| 4,930,674 A | 6/1990 | Barak |
| 4,941,623 A | 7/1990 | Pruitt |
| 4,944,443 A | 7/1990 | Oddsen et al. |
| 5,027,834 A * | 7/1991 | Pruitt ............................ 128/898 |
| 5,065,929 A | 11/1991 | Schulze et al. |
| 5,071,430 A | 12/1991 | de Salis et al. |
| 5,074,454 A | 12/1991 | Peters |
| 5,122,156 A | 6/1992 | Granger et al. |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,158,567 A | 10/1992 | Green |
| 5,192,288 A | 3/1993 | Thompson et al. |
| 5,211,649 A | 5/1993 | Kohler et al. |
| 5,221,036 A | 6/1993 | Takase |
| 5,222,963 A | 6/1993 | Brinkerhoff et al. |
| 5,222,975 A | 6/1993 | Crainich |
| 5,234,447 A | 8/1993 | Kaster et al. |
| 5,236,440 A | 8/1993 | Hlavacek |
| 5,258,009 A | 11/1993 | Conners |
| 5,282,806 A | 2/1994 | Haber et al. |
| 5,282,829 A | 2/1994 | Hermes |
| 5,304,204 A | 4/1994 | Bregen |
| 5,312,023 A | 5/1994 | Green et al. |
| 5,333,772 A | 8/1994 | Rothfuss et al. |
| 5,342,395 A | 8/1994 | Jarrett et al. |
| 5,342,396 A | 8/1994 | Cook |
| 5,350,400 A | 9/1994 | Esposito et al. |
| 5,366,479 A | 11/1994 | McGarry et al. |
| 5,397,324 A | 3/1995 | Carroll et al. |
| 5,405,072 A | 4/1995 | Zlock et al. |
| 5,411,508 A | 5/1995 | Bessler et al. |
| 5,413,272 A | 5/1995 | Green et al. |
| 5,417,361 A | 5/1995 | Williamson, IV |
| 5,425,745 A | 6/1995 | Green et al. |
| 5,452,837 A | 9/1995 | Williamson, IV et al. |
| 5,474,566 A | 12/1995 | Alesi et al. |
| 5,478,354 A | 12/1995 | Tovey et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,497,933 A | 3/1996 | DeFonzo et al. |
| 5,503,320 A | 4/1996 | Webster et al. |
| 5,503,635 A | 4/1996 | Sauer et al. |
| 5,505,363 A | 4/1996 | Green et al. |
| 5,507,426 A | 4/1996 | Young et al. |
| 5,509,596 A | 4/1996 | Green et al. |
| 5,520,700 A | 5/1996 | Beyar et al. |
| 5,529,235 A | 6/1996 | Boiarski et al. |
| 5,533,661 A | 7/1996 | Main et al. |
| 5,535,934 A | 7/1996 | Boiarski et al. |
| 5,540,375 A | 7/1996 | Bolanos et al. |
| 5,542,594 A | 8/1996 | McKean et al. |
| 5,542,949 A | 8/1996 | Yoon |
| 5,551,622 A | 9/1996 | Yoon |
| 5,553,765 A | 9/1996 | Knodel et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,241 A | 10/1996 | Knodel et al. |
| 5,562,682 A | 10/1996 | Oberlin et al. |
| 5,564,615 A | 10/1996 | Bishop et al. |
| 5,571,116 A | 11/1996 | Bolanos et al. |
| 5,571,285 A | 11/1996 | Chow et al. |
| 5,575,799 A | 11/1996 | Bolanos et al. |
| 5,577,654 A | 11/1996 | Bishop |
| 5,580,067 A | 12/1996 | Hamblin et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,601,224 A | 2/1997 | Bishop et al. |
| 5,603,443 A | 2/1997 | Clark et al. |
| 5,605,273 A | 2/1997 | Hamblin et al. |
| 5,607,094 A | 3/1997 | Clark et al. |
| 5,607,095 A | 3/1997 | Smith et al. |
| 5,609,285 A | 3/1997 | Grant et al. |
| 5,615,820 A | 4/1997 | Viola |
| 5,624,452 A | 4/1997 | Yates |
| 5,628,446 A | 5/1997 | Geiste et al. |
| 5,630,539 A | 5/1997 | Plyley et al. |
| 5,630,540 A | 5/1997 | Blewett |
| 5,632,432 A | 5/1997 | Schulze et al. |
| 5,632,433 A | 5/1997 | Grant et al. |
| 5,634,584 A | 6/1997 | Okorocha et al. |
| 5,636,780 A | 6/1997 | Green et al. |
| 5,639,008 A | 6/1997 | Gallagher et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,655,698 A | 8/1997 | Yoon |
| 5,657,921 A | 8/1997 | Young et al. |
| 5,662,258 A | 9/1997 | Knodel et al. |
| 5,662,260 A * | 9/1997 | Yoon ............................ 227/176.1 |
| 5,667,527 A | 9/1997 | Cook |
| 5,669,544 A | 9/1997 | Schulze et al. |
| 5,669,918 A | 9/1997 | Balazs et al. |
| 5,673,840 A | 10/1997 | Schulze et al. |
| 5,673,841 A | 10/1997 | Schulze et al. |
| 5,680,981 A | 10/1997 | Mililli et al. |
| 5,680,982 A | 10/1997 | Schulze et al. |
| 5,685,474 A | 11/1997 | Seeber |
| 5,690,269 A | 11/1997 | Bolanos et al. |
| 5,692,668 A | 12/1997 | Schulze et al. |
| 5,695,504 A | 12/1997 | Gifford, III et al. |
| 5,695,524 A | 12/1997 | Kelley et al. |
| 5,697,543 A | 12/1997 | Burdorff |

(56) References Cited

U.S. PATENT DOCUMENTS

| | | | |
|---|---|---|---|
| 5,697,943 A | 12/1997 | Sauer et al. |
| 5,702,408 A | 12/1997 | Wales et al. |
| 5,704,534 A | 1/1998 | Huitema et al. |
| 5,711,472 A | 1/1998 | Bryan |
| 5,713,505 A | 2/1998 | Huitema |
| 5,715,987 A | 2/1998 | Kelley et al. |
| 5,716,366 A | 2/1998 | Yates |
| 5,718,360 A | 2/1998 | Green et al. |
| 5,725,536 A | 3/1998 | Oberlin et al. |
| 5,725,554 A | 3/1998 | Simon et al. |
| 5,730,758 A | 3/1998 | Allgeyer |
| 5,732,871 A | 3/1998 | Clark et al. |
| 5,732,872 A | 3/1998 | Bolduc et al. |
| 5,743,456 A | 4/1998 | Jones et al. |
| 5,752,644 A | 5/1998 | Bolanos et al. |
| 5,758,814 A | 6/1998 | Gallagher et al. |
| 5,762,256 A | 6/1998 | Mastri et al. |
| 5,779,130 A | 7/1998 | Alesi et al. |
| 5,779,131 A | 7/1998 | Knodel et al. |
| 5,779,132 A | 7/1998 | Knodel et al. |
| 5,782,397 A | 7/1998 | Koukline |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,799,857 A | 9/1998 | Robertson et al. |
| 5,820,009 A | 10/1998 | Melling et al. |
| 5,826,776 A | 10/1998 | Schulze et al. |
| 5,827,298 A | 10/1998 | Hart et al. |
| 5,829,662 A | 11/1998 | Allen et al. |
| 5,833,695 A * | 11/1998 | Yoon ............................ 606/139 |
| 5,836,503 A | 11/1998 | Ehrenfels et al. |
| 5,839,639 A | 11/1998 | Sauer et al. |
| 5,855,311 A | 1/1999 | Hamblin et al. |
| 5,855,583 A | 1/1999 | Wang et al. |
| 5,860,581 A | 1/1999 | Robertson et al. |
| 5,865,361 A | 2/1999 | Milliman et al. |
| 5,868,760 A | 2/1999 | McGuckin, Jr. |
| 5,871,135 A | 2/1999 | Williamson, IV et al. |
| 5,897,562 A | 4/1999 | Bolanos et al. |
| 5,901,895 A | 5/1999 | Heaton et al. |
| 5,908,427 A | 6/1999 | McKean et al. |
| 5,911,353 A | 6/1999 | Bolanos et al. |
| 5,915,616 A | 6/1999 | Viola et al. |
| 5,919,198 A | 7/1999 | Graves, Jr. et al. |
| 5,937,951 A | 8/1999 | Izuchukwu et al. |
| 5,941,442 A | 8/1999 | Geiste et al. |
| 5,954,259 A | 9/1999 | Viola et al. |
| 6,010,054 A | 1/2000 | Johnson et al. |
| 6,024,748 A | 2/2000 | Manzo et al. |
| 6,032,849 A | 3/2000 | Mastri et al. |
| 6,045,560 A | 4/2000 | McKean et al. |
| 6,053,390 A | 4/2000 | Green et al. |
| RE36,720 E | 5/2000 | Green et al. |
| 6,074,401 A | 6/2000 | Gardiner et al. |
| 6,083,234 A | 7/2000 | Nicholas et al. |
| 6,083,242 A | 7/2000 | Cook |
| 6,086,600 A | 7/2000 | Kortenbach |
| 6,099,551 A | 8/2000 | Gabbay |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,171,330 B1 | 1/2001 | Benchetrit |
| 6,193,129 B1 | 2/2001 | Bittner et al. |
| 6,202,914 B1 | 3/2001 | Geiste et al. |
| 6,241,139 B1 | 6/2001 | Milliman et al. |
| 6,248,117 B1 | 6/2001 | Blatter |
| 6,250,532 B1 | 6/2001 | Green et al. |
| 6,258,107 B1 | 7/2001 | Balázs et al. |
| 6,264,086 B1 | 7/2001 | McGuckin, Jr. |
| 6,264,087 B1 | 7/2001 | Whitman |
| 6,273,897 B1 | 8/2001 | Dalessandro et al. |
| 6,302,311 B1 | 10/2001 | Adams et al. |
| 6,315,184 B1 | 11/2001 | Whitman |
| 6,330,965 B1 | 12/2001 | Milliman et al. |
| 6,338,737 B1 | 1/2002 | Toledano |
| 6,387,113 B1 | 5/2002 | Hawkins et al. |
| 6,391,038 B2 | 5/2002 | Vargas et al. |
| 6,398,797 B2 | 6/2002 | Bombard et al. |
| RE37,814 E | 8/2002 | Allgeyer |
| 6,436,107 B1 | 8/2002 | Wang et al. |
| 6,440,146 B2 | 8/2002 | Nicholas et al. |
| 6,443,973 B1 | 9/2002 | Whitman |
| 6,450,391 B1 | 9/2002 | Kayan et al. |
| 6,488,196 B1 | 12/2002 | Fenton, Jr. |
| 6,488,197 B1 | 12/2002 | Whitman |
| 6,491,201 B1 | 12/2002 | Whitman |
| 6,503,259 B2 | 1/2003 | Huxel et al. |
| 6,505,768 B2 | 1/2003 | Whitman |
| 6,517,565 B1 | 2/2003 | Whitman et al. |
| 6,517,566 B1 | 2/2003 | Hovland et al. |
| 6,533,157 B1 | 3/2003 | Whitman |
| 6,578,751 B2 | 6/2003 | Hartwick |
| 6,588,643 B2 | 7/2003 | Bolduc et al. |
| 6,601,749 B2 | 8/2003 | Sullivan et al. |
| 6,616,686 B2 | 9/2003 | Coleman et al. |
| 6,619,529 B2 | 9/2003 | Green et al. |
| 6,629,630 B2 | 10/2003 | Adams |
| 6,629,988 B2 | 10/2003 | Weadock |
| 6,638,297 B1 | 10/2003 | Huitema |
| 6,644,532 B2 | 11/2003 | Green et al. |
| 6,681,978 B2 | 1/2004 | Geiste et al. |
| 6,681,979 B2 | 1/2004 | Whitman |
| 6,692,507 B2 | 2/2004 | Pugsley et al. |
| 6,695,199 B2 | 2/2004 | Whitman |
| 6,698,643 B2 | 3/2004 | Whitman |
| 6,716,233 B1 | 4/2004 | Whitman |
| 6,722,552 B2 | 4/2004 | Fenton, Jr. |
| 6,726,697 B2 | 4/2004 | Nicholas et al. |
| 6,736,825 B2 | 5/2004 | Blatter et al. |
| 6,755,338 B2 | 6/2004 | Hahnen et al. |
| 6,769,590 B2 | 8/2004 | Vresh et al. |
| 6,769,594 B2 | 8/2004 | Orban, III |
| 6,773,438 B1 | 8/2004 | Knodel et al. |
| 6,786,382 B1 | 9/2004 | Hoffman |
| 6,805,273 B2 | 10/2004 | Bilotti et al. |
| 6,817,508 B1 | 11/2004 | Racenet et al. |
| 6,817,509 B2 | 11/2004 | Geiste et al. |
| 6,830,174 B2 | 12/2004 | Hillstead et al. |
| 6,843,403 B2 | 1/2005 | Whitman |
| RE38,708 E | 3/2005 | Bolanos et al. |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,851 B2 | 11/2005 | Heinrich |
| 6,960,220 B2 | 11/2005 | Marino et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,978 B2 | 1/2006 | Gannoe |
| 6,986,451 B1 | 1/2006 | Mastri et al. |
| 6,988,650 B2 | 1/2006 | Schwemberger et al. |
| 6,997,931 B2 | 2/2006 | Sauer et al. |
| 7,000,818 B2 | 2/2006 | Shelton, IV et al. |
| 7,000,819 B2 | 2/2006 | Swayze et al. |
| 7,008,435 B2 | 3/2006 | Cummins |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,731 B2 | 6/2006 | Shelton, IV et al. |
| 7,056,330 B2 | 6/2006 | Gayton |
| 7,063,712 B2 | 6/2006 | Vargas et al. |
| 7,070,083 B2 | 7/2006 | Jankowski |
| 7,077,856 B2 | 7/2006 | Whitman |
| 7,080,769 B2 | 7/2006 | Vresh et al. |
| 7,083,075 B2 | 8/2006 | Swayze et al. |

(56) References Cited

U.S. PATENT DOCUMENTS

| | | |
|---|---|---|
| 7,090,684 B2 | 8/2006 | McGuckin, Jr. et al. |
| 7,094,247 B2 | 8/2006 | Monassevitch et al. |
| 7,108,701 B2 | 9/2006 | Evens et al. |
| 7,108,709 B2 | 9/2006 | Cummins |
| 7,111,769 B2 | 9/2006 | Wales et al. |
| 7,114,642 B2 | 10/2006 | Whitman |
| 7,118,582 B1 | 10/2006 | Wang et al. |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,134,587 B2 | 11/2006 | Schwemberger et al. |
| 7,140,527 B2 | 11/2006 | Ehrenfels et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,156,863 B2 | 1/2007 | Sonnenschein et al. |
| 7,159,750 B2 | 1/2007 | Racenet et al. |
| 7,168,604 B2 | 1/2007 | Milliman et al. |
| 7,179,267 B2 | 2/2007 | Nolan et al. |
| 7,182,239 B1 | 2/2007 | Myers |
| 7,188,758 B2 | 3/2007 | Viola et al. |
| 7,207,471 B2 | 4/2007 | Heinrich et al. |
| 7,207,472 B2 | 4/2007 | Wukusick et al. |
| 7,210,609 B2 | 5/2007 | Leiboff et al. |
| 7,213,736 B2 | 5/2007 | Wales et al. |
| 7,220,272 B2 | 5/2007 | Weadock |
| 7,225,964 B2 | 6/2007 | Mastri et al. |
| 7,234,624 B2 | 6/2007 | Gresham et al. |
| 7,237,708 B1 | 7/2007 | Guy et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,296,722 B2 | 11/2007 | Ivanko |
| 7,296,724 B2 | 11/2007 | Green et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,334,718 B2 | 2/2008 | McAlister et al. |
| RE40,237 E | 4/2008 | Bilotti et al. |
| 7,354,447 B2 | 4/2008 | Shelton, IV et al. |
| 7,357,287 B2 | 4/2008 | Shelton, IV et al. |
| 7,364,060 B2 | 4/2008 | Milliman |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,398,907 B2 | 7/2008 | Racenet et al. |
| 7,398,908 B2 | 7/2008 | Holsten et al. |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,076 B2 | 8/2008 | Racenet et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| RE40,514 E | 9/2008 | Mastri et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,431,730 B2 | 10/2008 | Viola |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,455,208 B2 | 11/2008 | Wales et al. |
| 7,455,676 B2 | 11/2008 | Holsten et al. |
| 7,455,682 B2 | 11/2008 | Viola |
| 7,464,846 B2 | 12/2008 | Shelton, IV et al. |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 7,481,347 B2 | 1/2009 | Roy |
| 7,481,349 B2 | 1/2009 | Holsten et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,517,356 B2 | 4/2009 | Heinrich |
| 7,546,940 B2 | 6/2009 | Milliman et al. |
| 7,549,563 B2 | 6/2009 | Mather et al. |
| 7,549,564 B2 | 6/2009 | Boudreaux |
| 7,556,185 B2 | 7/2009 | Viola |
| 7,559,449 B2 | 7/2009 | Viola |
| 7,559,450 B2 | 7/2009 | Wales et al. |
| 7,559,452 B2 | 7/2009 | Wales et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,575,144 B2 | 8/2009 | Ortiz et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,624,902 B2 | 12/2009 | Marczyk et al. |
| 7,624,903 B2 | 12/2009 | Green et al. |
| 7,631,793 B2 | 12/2009 | Rethy et al. |
| 7,635,074 B2 | 12/2009 | Olson et al. |
| 7,637,409 B2 | 12/2009 | Marczyk |
| 7,641,095 B2 | 1/2010 | Viola |
| 7,644,848 B2 | 1/2010 | Swayze et al. |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,686,201 B2 | 3/2010 | Csiky |
| 7,699,204 B2 | 4/2010 | Viola |
| 7,699,859 B2 | 4/2010 | Bombard et al. |
| 7,708,180 B2 | 5/2010 | Murray et al. |
| 7,717,312 B2 | 5/2010 | Beetel |
| 7,717,313 B2 | 5/2010 | Criscuolo et al. |
| 7,721,930 B2 | 5/2010 | McKenna et al. |
| 7,721,931 B2 | 5/2010 | Shelton, IV et al. |
| 7,721,934 B2 | 5/2010 | Shelton, IV et al. |
| 7,721,936 B2 | 5/2010 | Shelton, IV et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,904 B2 | 7/2010 | Shelton, IV et al. |
| 7,758,612 B2 | 7/2010 | Shipp |

(56) References Cited

U.S. PATENT DOCUMENTS

| | | | |
|---|---|---|---|
| 7,766,209 B2 | 8/2010 | Baxter, III et al. |
| 7,766,210 B2 | 8/2010 | Shelton, IV et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,780,054 B2 | 8/2010 | Wales |
| 7,784,662 B2 | 8/2010 | Wales et al. |
| 7,784,663 B2 | 8/2010 | Shelton, IV |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,824,426 B2 | 11/2010 | Racenet et al. |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,533 B2 | 12/2010 | Marczyk et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,857,183 B2 | 12/2010 | Shelton, IV |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,871,418 B2 | 1/2011 | Thompson et al. |
| 7,891,531 B1 | 2/2011 | Ward |
| 7,891,532 B2 | 2/2011 | Mastri et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,909,220 B2 | 3/2011 | Viola |
| 7,909,221 B2 | 3/2011 | Viola et al. |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,376 B1 | 4/2011 | Knodel et al. |
| 7,918,377 B2 | 4/2011 | Measamer et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,926,691 B2 | 4/2011 | Viola et al. |
| 7,934,630 B2 | 5/2011 | Shelton, IV et al. |
| 7,934,631 B2 | 5/2011 | Balbierz et al. |
| 7,938,307 B2 | 5/2011 | Bettuchi |
| 7,942,890 B2 | 5/2011 | D'Agostino et al. |
| 7,950,560 B2 | 5/2011 | Zemlok et al. |
| 7,950,561 B2 | 5/2011 | Aranyi |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,432 B2 | 6/2011 | Knodel et al. |
| 7,966,799 B2 | 6/2011 | Morgan et al. |
| 7,967,180 B2 | 6/2011 | Scirica |
| 7,967,181 B2 | 6/2011 | Viola et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,992,757 B2 | 8/2011 | Wheeler et al. |
| 7,997,469 B2 | 8/2011 | Olson et al. |
| 8,002,795 B2 | 8/2011 | Beetel |
| 8,006,885 B2 | 8/2011 | Marczyk |
| 8,006,889 B2 | 8/2011 | Adams et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,858 B2 | 9/2011 | Whitman |
| 8,020,742 B2 | 9/2011 | Marczyk |
| 8,020,743 B2 | 9/2011 | Shelton, IV |
| 8,025,199 B2 | 9/2011 | Whitman et al. |
| 8,028,883 B2 | 10/2011 | Stopek |
| 8,028,885 B2 | 10/2011 | Smith et al. |
| 8,034,077 B2 | 10/2011 | Smith et al. |
| 8,038,045 B2 | 10/2011 | Bettuchi et al. |
| 8,038,046 B2 | 10/2011 | Smith et al. |
| 8,056,787 B2 | 11/2011 | Boudreaux et al. |
| 8,056,788 B2 | 11/2011 | Mastri et al. |
| 8,066,167 B2 | 11/2011 | Measamer et al. |
| D650,074 S | 12/2011 | Hunt et al. |
| 8,083,119 B2 | 12/2011 | Prommersberger |
| 8,083,120 B2 | 12/2011 | Shelton, IV et al. |
| 8,091,756 B2 | 1/2012 | Viola |
| 8,097,017 B2 | 1/2012 | Viola |
| 8,100,310 B2 | 1/2012 | Zemlok |
| 8,109,426 B2 | 2/2012 | Milliman et al. |
| 8,113,410 B2 | 2/2012 | Hall et al. |
| 8,123,103 B2 | 2/2012 | Milliman |
| 8,128,645 B2 | 3/2012 | Sonnenschein et al. |
| 8,136,712 B2 | 3/2012 | Zingman |
| 8,141,762 B2 | 3/2012 | Bedi et al. |
| 8,141,763 B2 | 3/2012 | Milliman |
| 8,152,041 B2 | 4/2012 | Kostrzewski |
| 8,157,145 B2 | 4/2012 | Shelton, IV et al. |
| 8,157,152 B2 | 4/2012 | Holsten et al. |
| 8,157,153 B2 | 4/2012 | Shelton, IV et al. |
| 8,161,977 B2 | 4/2012 | Shelton, IV et al. |
| 8,162,197 B2 | 4/2012 | Mastri et al. |
| 8,167,185 B2 | 5/2012 | Shelton, IV et al. |
| 8,167,895 B2 | 5/2012 | D'Agostino et al. |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,186,555 B2 | 5/2012 | Shelton, IV et al. |
| 8,186,560 B2 | 5/2012 | Hess et al. |
| 8,191,752 B2 | 6/2012 | Scirica |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,781 B2 | 6/2012 | Baxter, III et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,215,531 B2 | 7/2012 | Shelton, IV et al. |
| 8,215,533 B2 | 7/2012 | Viola et al. |
| 8,220,688 B2 | 7/2012 | Laurent et al. |
| 8,220,690 B2 | 7/2012 | Hess et al. |
| 8,231,040 B2 | 7/2012 | Zemlok et al. |
| 8,231,041 B2 | 7/2012 | Marczyk et al. |
| 8,231,042 B2 | 7/2012 | Hessler et al. |
| 8,231,043 B2 | 7/2012 | Tarinelli et al. |
| 8,236,010 B2 | 8/2012 | Ortiz et al. |
| 8,245,899 B2 | 8/2012 | Swensgard et al. |
| 8,245,901 B2 | 8/2012 | Stopek |
| 8,256,654 B2 | 9/2012 | Bettuchi et al. |
| 8,256,655 B2 | 9/2012 | Sniffin et al. |
| 8,267,300 B2 | 9/2012 | Boudreaux |
| 8,272,553 B2 | 9/2012 | Mastri et al. |
| 8,276,801 B2 | 10/2012 | Zemlok et al. |
| 8,276,802 B2 | 10/2012 | Kostrzewski |
| 8,281,973 B2 | 10/2012 | Wenchell et al. |
| 8,286,845 B2 | 10/2012 | Perry et al. |
| 8,292,151 B2 | 10/2012 | Viola |
| 8,292,155 B2 | 10/2012 | Shelton, IV et al. |
| 8,292,157 B2 | 10/2012 | Smith et al. |

(56) References Cited

U.S. PATENT DOCUMENTS

| | | |
|---|---|---|
| 8,308,040 B2 | 11/2012 | Huang et al. |
| 8,308,042 B2 | 11/2012 | Aranyi |
| 8,308,046 B2 | 11/2012 | Prommersberger |
| 8,313,496 B2 | 11/2012 | Sauer et al. |
| 8,317,070 B2 | 11/2012 | Hueil et al. |
| 8,317,074 B2 | 11/2012 | Ortiz et al. |
| 8,322,455 B2 | 12/2012 | Shelton, IV et al. |
| 8,322,589 B2 | 12/2012 | Boudreaux |
| 8,328,062 B2 | 12/2012 | Viola |
| 8,328,063 B2 | 12/2012 | Milliman et al. |
| 8,328,064 B2 | 12/2012 | Racenet et al. |
| 8,333,313 B2 | 12/2012 | Boudreaux et al. |
| 8,348,123 B2 | 1/2013 | Scirica et al. |
| 8,348,127 B2 | 1/2013 | Marczyk |
| 8,348,129 B2 | 1/2013 | Bedi et al. |
| 8,348,131 B2 | 1/2013 | Omaits et al. |
| 8,348,972 B2 | 1/2013 | Soltz et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,360,296 B2 | 1/2013 | Zingman |
| 8,360,297 B2 | 1/2013 | Shelton, IV et al. |
| 8,360,299 B2 | 1/2013 | Zemlok et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,513 B2 | 3/2013 | Jankowski |
| 8,393,514 B2 | 3/2013 | Shelton, IV et al. |
| 8,397,971 B2 | 3/2013 | Yates et al. |
| 8,403,198 B2 | 3/2013 | Sorrentino et al. |
| 8,408,439 B2 | 4/2013 | Huang et al. |
| 8,408,442 B2 | 4/2013 | Racenet et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,577 B2 | 4/2013 | Boudreaux et al. |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,444,036 B2 | 5/2013 | Shelton, IV |
| 8,453,904 B2 | 6/2013 | Eskaros et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,459,520 B2 | 6/2013 | Giordano et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,925 B2 | 6/2013 | Hull et al. |
| 8,474,677 B2 | 7/2013 | Woodard, Jr. et al. |
| 8,479,969 B2 | 7/2013 | Shelton, IV |
| 8,485,412 B2 | 7/2013 | Shelton, IV et al. |
| 8,485,413 B2 | 7/2013 | Scheib et al. |
| 8,490,853 B2 | 7/2013 | Criscuolo et al. |
| 8,496,156 B2 | 7/2013 | Sniffin et al. |
| 8,499,993 B2 | 8/2013 | Shelton, IV et al. |
| 8,517,239 B2 | 8/2013 | Scheib et al. |
| 8,517,243 B2 | 8/2013 | Giordano et al. |
| 8,517,244 B2 | 8/2013 | Shelton, IV et al. |
| 8,529,600 B2 | 9/2013 | Woodard, Jr. et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,561,870 B2 | 10/2013 | Baxter, III et al. |
| 8,567,656 B2 | 10/2013 | Shelton, IV et al. |
| 8,573,461 B2 | 11/2013 | Shelton, IV et al. |
| 8,573,465 B2 | 11/2013 | Shelton, IV et al. |
| 8,579,937 B2 | 11/2013 | Gresham |
| 8,584,919 B2 | 11/2013 | Hueil et al. |
| 8,590,762 B2 | 11/2013 | Hess et al. |
| 8,602,287 B2 | 12/2013 | Yates et al. |
| 8,602,288 B2 | 12/2013 | Shelton, IV et al. |
| 8,608,044 B2 | 12/2013 | Hueil et al. |
| 8,608,045 B2 | 12/2013 | Smith et al. |
| 8,608,046 B2 | 12/2013 | Laurent et al. |
| 2002/0117534 A1 | 8/2002 | Green et al. |
| 2004/0006372 A1 | 1/2004 | Racenet et al. |
| 2004/0034369 A1 | 2/2004 | Sauer et al. |
| 2004/0094597 A1 | 5/2004 | Whitman et al. |
| 2004/0108357 A1 | 6/2004 | Milliman et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0222268 A1 | 11/2004 | Bilotti et al. |
| 2004/0232201 A1 | 11/2004 | Wenchell et al. |
| 2004/0236352 A1 | 11/2004 | Wang et al. |
| 2004/0243151 A1 | 12/2004 | Demmy et al. |
| 2004/0254608 A1 | 12/2004 | Huitema et al. |
| 2004/0267310 A1 | 12/2004 | Racenet et al. |
| 2005/0059997 A1 | 3/2005 | Bauman et al. |
| 2005/0103819 A1 | 5/2005 | Racenet et al. |
| 2005/0119669 A1 | 6/2005 | Demmy |
| 2005/0125009 A1 | 6/2005 | Perry et al. |
| 2005/0143759 A1 | 6/2005 | Kelly |
| 2005/0145675 A1 | 7/2005 | Hartwick et al. |
| 2005/0187576 A1 | 8/2005 | Whitman et al. |
| 2005/0189397 A1 | 9/2005 | Jankowski |
| 2005/0192628 A1 | 9/2005 | Viola |
| 2005/0216055 A1 | 9/2005 | Scirica et al. |
| 2005/0240222 A1 | 10/2005 | Shipp |
| 2005/0263563 A1 | 12/2005 | Racenet et al. |
| 2005/0274768 A1 | 12/2005 | Cummins et al. |
| 2006/0011699 A1 | 1/2006 | Olson et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0085033 A1 | 4/2006 | Criscuolo et al. |
| 2006/0100643 A1 | 5/2006 | Laufer et al. |
| 2006/0108393 A1 | 5/2006 | Heinrich et al. |
| 2006/0161185 A1 | 7/2006 | Saadat et al. |
| 2006/0180634 A1 | 8/2006 | Shelton, IV et al. |
| 2006/0201989 A1 | 9/2006 | Ojeda |
| 2006/0226196 A1 | 10/2006 | Hueil et al. |
| 2006/0235469 A1 | 10/2006 | Viola |
| 2006/0241692 A1 | 10/2006 | McGuckin, Jr. et al. |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0023476 A1 | 2/2007 | Whitman et al. |
| 2007/0023477 A1 | 2/2007 | Whitman et al. |
| 2007/0034668 A1 | 2/2007 | Holsten et al. |
| 2007/0066981 A1 | 3/2007 | Meagher |
| 2007/0073341 A1 | 3/2007 | Smith |
| 2007/0084897 A1 | 4/2007 | Shelton, IV et al. |
| 2007/0093869 A1 | 4/2007 | Bloom et al. |
| 2007/0102472 A1 | 5/2007 | Shelton, IV |
| 2007/0106317 A1 | 5/2007 | Shelton, IV et al. |
| 2007/0114261 A1 | 5/2007 | Ortiz et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175955 A1 | 8/2007 | Shelton, IV et al. |
| 2007/0179528 A1 | 8/2007 | Soltz et al. |
| 2007/0181632 A1 | 8/2007 | Milliman |
| 2007/0194079 A1 | 8/2007 | Hueil et al. |
| 2007/0194082 A1 | 8/2007 | Morgan et al. |
| 2007/0203510 A1 | 8/2007 | Bettuchi |
| 2007/0219571 A1 | 9/2007 | Balbierz et al. |
| 2007/0221700 A1 | 9/2007 | Ortiz et al. |
| 2007/0225562 A1 | 9/2007 | Spivey et al. |
| 2007/0239028 A1 | 10/2007 | Houser et al. |
| 2007/0246505 A1 | 10/2007 | Pace-Floridia et al. |
| 2007/0270884 A1 | 11/2007 | Smith et al. |
| 2007/0276409 A1 | 11/2007 | Ortiz et al. |
| 2008/0029570 A1 | 2/2008 | Shelton et al. |
| 2008/0029573 A1 | 2/2008 | Shelton et al. |

(56) References Cited

U.S. PATENT DOCUMENTS

| | | |
|---|---|---|
| 2008/0029574 A1 | 2/2008 | Shelton et al. |
| 2008/0029575 A1 | 2/2008 | Shelton et al. |
| 2008/0035701 A1 | 2/2008 | Racenet et al. |
| 2008/0041917 A1 | 2/2008 | Racenet et al. |
| 2008/0078800 A1 | 4/2008 | Hess et al. |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083808 A1 | 4/2008 | Scirica |
| 2008/0083813 A1 | 4/2008 | Zemlok et al. |
| 2008/0140115 A1 | 6/2008 | Stopek |
| 2008/0167522 A1 | 7/2008 | Giordano et al. |
| 2008/0169328 A1 | 7/2008 | Shelton |
| 2008/0169329 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0172088 A1 | 7/2008 | Smith et al. |
| 2008/0185419 A1 | 8/2008 | Smith et al. |
| 2008/0197167 A1 | 8/2008 | Viola et al. |
| 2008/0251568 A1 | 10/2008 | Zemlok et al. |
| 2008/0251569 A1 | 10/2008 | Smith et al. |
| 2008/0283570 A1 | 11/2008 | Boyden et al. |
| 2008/0290134 A1 | 11/2008 | Bettuchi et al. |
| 2008/0296346 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0078736 A1 | 3/2009 | Van Lue |
| 2009/0108048 A1 | 4/2009 | Zemlok et al. |
| 2009/0114701 A1 | 5/2009 | Zemlok et al. |
| 2009/0149871 A9 | 6/2009 | Kagan et al. |
| 2009/0152324 A1* | 6/2009 | Holsten et al. ............ 227/176.1 |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0209946 A1 | 8/2009 | Swayze et al. |
| 2009/0209990 A1 | 8/2009 | Yates et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2010/0012704 A1 | 1/2010 | Tarinelli Racenet et al. |
| 2010/0069942 A1 | 3/2010 | Shelton, IV |
| 2010/0072254 A1 | 3/2010 | Aranyi et al. |
| 2010/0076475 A1 | 3/2010 | Yates et al. |
| 2010/0108740 A1 | 5/2010 | Pastorelli et al. |
| 2010/0108741 A1 | 5/2010 | Hessler et al. |
| 2010/0133317 A1 | 6/2010 | Shelton, IV et al. |
| 2010/0147922 A1 | 6/2010 | Olson |
| 2010/0163598 A1 | 7/2010 | Belzer |
| 2010/0179382 A1 | 7/2010 | Shelton, IV et al. |
| 2010/0193566 A1 | 8/2010 | Schieb et al. |
| 2010/0200637 A1 | 8/2010 | Beetel |
| 2010/0222901 A1 | 9/2010 | Swayze et al. |
| 2010/0224669 A1 | 9/2010 | Shelton, IV et al. |
| 2010/0230465 A1 | 9/2010 | Smith et al. |
| 2010/0243707 A1 | 9/2010 | Olson et al. |
| 2010/0243708 A1 | 9/2010 | Aranyi et al. |
| 2010/0243709 A1 | 9/2010 | Hess et al. |
| 2010/0258611 A1 | 10/2010 | Smith et al. |
| 2010/0276471 A1 | 11/2010 | Whitman |
| 2010/0294827 A1 | 11/2010 | Boyden et al. |
| 2010/0294829 A1 | 11/2010 | Giordano et al. |
| 2010/0301095 A1 | 12/2010 | Shelton, IV et al. |
| 2010/0305552 A1 | 12/2010 | Shelton, IV et al. |
| 2010/0312261 A1 | 12/2010 | Suzuki et al. |
| 2010/0331880 A1 | 12/2010 | Stopek |
| 2011/0006099 A1 | 1/2011 | Hall et al. |
| 2011/0006101 A1 | 1/2011 | Hall et al. |
| 2011/0011916 A1 | 1/2011 | Levine |
| 2011/0017801 A1 | 1/2011 | Zemlok et al. |
| 2011/0024477 A1 | 2/2011 | Hall et al. |
| 2011/0024478 A1 | 2/2011 | Shelton, IV |
| 2011/0024479 A1 | 2/2011 | Swensgard et al. |
| 2011/0036887 A1 | 2/2011 | Zemlok et al. |
| 2011/0060363 A1 | 3/2011 | Hess et al. |
| 2011/0068148 A1 | 3/2011 | Hall et al. |
| 2011/0084112 A1 | 4/2011 | Kostrzewski |
| 2011/0087276 A1 | 4/2011 | Bedi et al. |
| 2011/0087279 A1 | 4/2011 | Shah et al. |
| 2011/0095068 A1 | 4/2011 | Patel |
| 2011/0101065 A1 | 5/2011 | Milliman |
| 2011/0114697 A1 | 5/2011 | Baxter, III et al. |
| 2011/0114700 A1 | 5/2011 | Baxter, III et al. |
| 2011/0118761 A1 | 5/2011 | Baxter, III et al. |
| 2011/0125176 A1 | 5/2011 | Yates et al. |
| 2011/0125177 A1 | 5/2011 | Yates et al. |
| 2011/0132964 A1 | 6/2011 | Weisenburgh, II et al. |
| 2011/0144430 A1 | 6/2011 | Spivey et al. |
| 2011/0147433 A1 | 6/2011 | Shelton, IV et al. |
| 2011/0147434 A1 | 6/2011 | Hueil et al. |
| 2011/0155781 A1 | 6/2011 | Swensgard et al. |
| 2011/0155784 A1 | 6/2011 | Shelton, IV et al. |
| 2011/0155786 A1 | 6/2011 | Shelton, IV |
| 2011/0155787 A1 | 6/2011 | Baxter, III et al. |
| 2011/0163146 A1 | 7/2011 | Ortiz et al. |
| 2011/0174861 A1 | 7/2011 | Shelton, IV et al. |
| 2011/0174862 A1 | 7/2011 | Shelton, IV et al. |
| 2011/0192882 A1 | 8/2011 | Hess et al. |
| 2011/0210156 A1 | 9/2011 | Smith et al. |
| 2011/0253765 A1 | 10/2011 | Nicholas et al. |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2011/0295242 A1 | 12/2011 | Spivey et al. |
| 2011/0295269 A1 | 12/2011 | Swensgard et al. |
| 2011/0295270 A1 | 12/2011 | Giordano et al. |
| 2011/0295295 A1 | 12/2011 | Shelton, IV et al. |
| 2012/0024934 A1 | 2/2012 | Shelton, IV et al. |
| 2012/0024935 A1 | 2/2012 | Shelton, IV et al. |
| 2012/0024936 A1 | 2/2012 | Baxter, III et al. |
| 2012/0029272 A1 | 2/2012 | Shelton, IV et al. |
| 2012/0029544 A1 | 2/2012 | Shelton, IV et al. |
| 2012/0029547 A1 | 2/2012 | Shelton, IV et al. |
| 2012/0046692 A1 | 2/2012 | Smith et al. |
| 2012/0071711 A1 | 3/2012 | Shelton, IV et al. |
| 2012/0071866 A1 | 3/2012 | Kerr et al. |
| 2012/0074196 A1 | 3/2012 | Shelton, IV et al. |
| 2012/0074198 A1 | 3/2012 | Huitema et al. |
| 2012/0074200 A1 | 3/2012 | Schmid et al. |
| 2012/0074201 A1 | 3/2012 | Baxter, III et al. |
| 2012/0080332 A1 | 4/2012 | Shelton, IV et al. |
| 2012/0080335 A1 | 4/2012 | Shelton, IV et al. |
| 2012/0080336 A1 | 4/2012 | Shelton, IV et al. |
| 2012/0080337 A1 | 4/2012 | Shelton, IV et al. |
| 2012/0080338 A1 | 4/2012 | Shelton, IV et al. |
| 2012/0080339 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080345 A1 | 4/2012 | Morgan et al. |

(56) References Cited

U.S. PATENT DOCUMENTS

| | | |
|---|---|---|
| 2012/0080475 A1 | 4/2012 | Smith et al. |
| 2012/0080477 A1 | 4/2012 | Leimbach et al. |
| 2012/0080478 A1 | 4/2012 | Morgan et al. |
| 2012/0080479 A1 | 4/2012 | Shelton, IV |
| 2012/0080480 A1 | 4/2012 | Woodard, Jr. et al. |
| 2012/0080481 A1 | 4/2012 | Widenhouse et al. |
| 2012/0080482 A1 | 4/2012 | Schall et al. |
| 2012/0080483 A1 | 4/2012 | Riestenberg et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080496 A1 | 4/2012 | Schall et al. |
| 2012/0080498 A1 | 4/2012 | Shelton, IV et al. |
| 2012/0080499 A1 | 4/2012 | Schall et al. |
| 2012/0080500 A1 | 4/2012 | Morgan et al. |
| 2012/0080501 A1 | 4/2012 | Morgan et al. |
| 2012/0080502 A1 | 4/2012 | Morgan et al. |
| 2012/0080503 A1 | 4/2012 | Woodard, Jr. et al. |
| 2012/0083833 A1 | 4/2012 | Shelton, IV et al. |
| 2012/0083834 A1 | 4/2012 | Shelton, IV et al. |
| 2012/0083835 A1 | 4/2012 | Shelton, IV et al. |
| 2012/0083836 A1 | 4/2012 | Shelton, IV et al. |
| 2012/0132450 A1 | 5/2012 | Timm et al. |
| 2012/0138658 A1 | 6/2012 | Ullrich et al. |
| 2012/0138660 A1 | 6/2012 | Shelton, IV |
| 2012/0160721 A1 | 6/2012 | Shelton, IV et al. |
| 2012/0175399 A1 | 7/2012 | Shelton et al. |
| 2012/0187179 A1 | 7/2012 | Gleiman |
| 2012/0199630 A1 | 8/2012 | Shelton, IV et al |
| 2012/0199632 A1 | 8/2012 | Spivey et al. |
| 2012/0203247 A1 | 8/2012 | Shelton, IV et al. |
| 2012/0234890 A1 | 9/2012 | Aronhalt et al. |
| 2012/0234891 A1 | 9/2012 | Aronhalt et al. |
| 2012/0234892 A1 | 9/2012 | Aronhalt et al. |
| 2012/0234893 A1 | 9/2012 | Schuckmann et al. |
| 2012/0234895 A1 | 9/2012 | O'Connor et al. |
| 2012/0234896 A1 | 9/2012 | Ellerhorst et al. |
| 2012/0234897 A1 | 9/2012 | Shelton, IV et al. |
| 2012/0234898 A1 | 9/2012 | Shelton, IV et al. |
| 2012/0234899 A1 | 9/2012 | Scheib et al. |
| 2012/0238823 A1 | 9/2012 | Hagerty et al. |
| 2012/0238824 A1 | 9/2012 | Widenhouse et al. |
| 2012/0238826 A1 | 9/2012 | Yoo et al. |
| 2012/0238829 A1 | 9/2012 | Shelton, IV et al. |
| 2012/0239009 A1 | 9/2012 | Mollere et al. |
| 2012/0239010 A1 | 9/2012 | Shelton, IV et al. |
| 2012/0239075 A1 | 9/2012 | Widenhouse et al. |
| 2012/0239082 A1 | 9/2012 | Shelton, IV et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241505 A1 | 9/2012 | Alexander, III et al. |
| 2012/0248169 A1 | 10/2012 | Widenhouse et al. |
| 2012/0253298 A1 | 10/2012 | Henderson et al. |
| 2012/0283707 A1 | 11/2012 | Giordano et al. |
| 2012/0283748 A1 | 11/2012 | Ortiz et al. |
| 2012/0292367 A1 | 11/2012 | Morgan et al. |
| 2012/0292370 A1 | 11/2012 | Hess et al. |
| 2012/0298719 A1 | 11/2012 | Shelton, IV et al. |
| 2012/0298722 A1 | 11/2012 | Hess et al. |
| 2012/0312860 A1 | 12/2012 | Ming et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2012/0325892 A1 | 12/2012 | Kostrzewski |
| 2013/0012931 A1 | 1/2013 | Spivey et al. |
| 2013/0012957 A1 | 1/2013 | Shelton, IV et al. |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0037596 A1 | 2/2013 | Bear et al. |
| 2013/0048697 A1 | 2/2013 | Shelton, IV et al. |
| 2013/0056520 A1 | 3/2013 | Swensgard |
| 2013/0056521 A1 | 3/2013 | Swensgard |
| 2013/0056522 A1 | 3/2013 | Swensgard |
| 2013/0075443 A1 | 3/2013 | Giordano et al. |
| 2013/0075448 A1 | 3/2013 | Schmid et al. |
| 2013/0075449 A1 | 3/2013 | Schmid et al. |
| 2013/0075450 A1 | 3/2013 | Schmid et al. |
| 2013/0079814 A1 | 3/2013 | Hess et al. |
| 2013/0087597 A1 | 4/2013 | Shelton, IV et al. |
| 2013/0105551 A1 | 5/2013 | Zingman |
| 2013/0116668 A1 | 5/2013 | Shelton, IV et al. |
| 2013/0116669 A1 | 5/2013 | Shelton, IV et al. |
| 2013/0126581 A1 | 5/2013 | Yates et al. |
| 2013/0126582 A1 | 5/2013 | Shelton, IV et al. |
| 2013/0126583 A1 | 5/2013 | Hueil et al. |
| 2013/0146641 A1 | 6/2013 | Shelton, IV et al. |
| 2013/0146642 A1 | 6/2013 | Shelton, IV et al. |
| 2013/0146643 A1 | 6/2013 | Schmid et al. |
| 2013/0153636 A1 | 6/2013 | Shelton, IV et al. |
| 2013/0153641 A1 | 6/2013 | Shelton, IV et al. |
| 2013/0168435 A1 | 7/2013 | Huang et al. |
| 2013/0172929 A1 | 7/2013 | Hess et al. |
| 2013/0175317 A1 | 7/2013 | Yates et al. |
| 2013/0175321 A1 | 7/2013 | Shelton, IV et al. |
| 2013/0175322 A1 | 7/2013 | Yates et al. |
| 2013/0181030 A1 | 7/2013 | Hess et al. |
| 2013/0181033 A1 | 7/2013 | Shelton, IV et al. |
| 2013/0181034 A1 | 7/2013 | Shelton, IV et al. |
| 2013/0184718 A1 | 7/2013 | Smith et al. |
| 2013/0184719 A1 | 7/2013 | Shelton, IV et al. |
| 2013/0186932 A1 | 7/2013 | Shelton, IV et al. |
| 2013/0186933 A1 | 7/2013 | Shelton, IV et al. |
| 2013/0186934 A1 | 7/2013 | Shelton, IV et al. |
| 2013/0186936 A1 | 7/2013 | Shelton, IV |
| 2013/0190733 A1 | 7/2013 | Giordano et al. |
| 2013/0190757 A1 | 7/2013 | Yates et al. |
| 2013/0193188 A1 | 8/2013 | Shelton, IV et al. |
| 2013/0193189 A1 | 8/2013 | Swensgard et al. |
| 2013/0197556 A1 | 8/2013 | Shelton, IV et al. |
| 2013/0200132 A1 | 8/2013 | Moore et al. |
| 2013/0206814 A1 | 8/2013 | Morgan et al. |
| 2013/0214030 A1 | 8/2013 | Aronhalt et al. |
| 2013/0221063 A1 | 8/2013 | Aronhalt et al. |
| 2013/0221064 A1 | 8/2013 | Aronhalt et al. |
| 2013/0221065 A1 | 8/2013 | Aronhalt et al. |
| 2013/0233906 A1 | 9/2013 | Hess et al. |
| 2013/0248576 A1 | 9/2013 | Laurent et al. |
| 2013/0248577 A1 | 9/2013 | Leimbach et al. |
| 2013/0256365 A1 | 10/2013 | Shelton, IV et al. |
| 2013/0256366 A1 | 10/2013 | Shelton, IV et al. |
| 2013/0256367 A1 | 10/2013 | Scheib et al. |
| 2013/0256368 A1 | 10/2013 | Timm et al. |
| 2013/0256369 A1 | 10/2013 | Schmid et al. |
| 2013/0256371 A1 | 10/2013 | Shelton, IV et al. |
| 2013/0256372 A1 | 10/2013 | Baxter, III et al. |
| 2013/0256373 A1 | 10/2013 | Schmid et al. |
| 2013/0256374 A1 | 10/2013 | Shelton, IV et al. |
| 2013/0256375 A1 | 10/2013 | Shelton, IV et al. |
| 2013/0256376 A1 | 10/2013 | Barton et al. |
| 2013/0256377 A1 | 10/2013 | Schmid et al. |
| 2013/0256378 A1 | 10/2013 | Schmid et al. |
| 2013/0256379 A1 | 10/2013 | Schmid et al. |
| 2013/0256380 A1 | 10/2013 | Schmid et al. |
| 2013/0256382 A1 | 10/2013 | Swayze et al. |
| 2013/0256383 A1 | 10/2013 | Aronhalt et al. |
| 2013/0261648 A1 | 10/2013 | Laurent et al. |
| 2013/0270322 A1 | 10/2013 | Scheib et al. |

(56) References Cited

U.S. PATENT DOCUMENTS

| | | |
|---|---|---|
| 2013/0313303 A1 | 11/2013 | Shelton, IV et al. |
| 2013/0313304 A1 | 11/2013 | Shelton, IV et al. |
| 2013/0313306 A1 | 11/2013 | Shelton, IV et al. |
| 2013/0327809 A1 | 12/2013 | Shelton, IV et al. |
| 2013/0327810 A1 | 12/2013 | Swayze et al. |

FOREIGN PATENT DOCUMENTS

| | | |
|---|---|---|
| CA | 2512960 A1 | 1/2006 |
| CA | 2514274 A1 | 1/2006 |
| CN | 2488482 Y | 5/2002 |
| CN | 1523725 A | 8/2004 |
| CN | 1634601 A | 7/2005 |
| CN | 1868411 A | 11/2006 |
| CN | 1915180 A | 2/2007 |
| CN | 101011286 A | 8/2007 |
| CN | 101095621 A | 1/2008 |
| CN | 101023879 B | 3/2013 |
| DE | 273689 C | 5/1914 |
| DE | 1775926 A | 1/1972 |
| DE | 3036217 A1 | 4/1982 |
| DE | 3212828 A1 | 11/1982 |
| DE | 3210466 A1 | 9/1983 |
| DE | 3709067 A1 | 9/1988 |
| DE | 9412228 U | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 20016423 U1 | 2/2001 |
| DE | 10052679 A1 | 5/2001 |
| DE | 20112837 U1 | 10/2001 |
| DE | 20121753 U1 | 4/2003 |
| DE | 10314072 A1 | 10/2004 |
| DE | 202007003114 U1 | 6/2007 |
| EP | 0122046 A1 | 10/1984 |
| EP | 0070230 B1 | 10/1985 |
| EP | 0156774 A2 | 10/1985 |
| EP | 0387980 B1 | 10/1985 |
| EP | 0033548 B1 | 5/1986 |
| EP | 0129442 B1 | 11/1987 |
| EP | 0276104 A2 | 7/1988 |
| EP | 0178940 B1 | 1/1991 |
| EP | 0178941 B1 | 1/1991 |
| EP | 0248844 B1 | 1/1993 |
| EP | 0545029 A1 | 6/1993 |
| EP | 0277959 B1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0505036 B1 | 5/1995 |
| EP | 0653189 A2 | 5/1995 |
| EP | 0669104 A1 | 8/1995 |
| EP | 0511470 B1 | 10/1995 |
| EP | 0674876 A2 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0705571 A1 | 4/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0843906 B1 | 3/2000 |
| EP | 0552050 B1 | 5/2000 |
| EP | 0833592 B1 | 5/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1090592 A1 | 4/2001 |
| EP | 1095627 A1 | 5/2001 |
| EP | 1256318 B1 | 5/2001 |
| EP | 0806914 B1 | 9/2001 |
| EP | 0768840 B1 | 12/2001 |
| EP | 0908152 B1 | 1/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 0717960 B1 | 2/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0741996 B1 | 2/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1086713 B1 | 5/2004 |
| EP | 0996378 B1 | 6/2004 |
| EP | 1426012 A1 | 6/2004 |

(56) References Cited

FOREIGN PATENT DOCUMENTS

| | | | |
|---|---|---|---|
| EP | 0833593 | B2 | 7/2004 |
| EP | 1442694 | A1 | 8/2004 |
| EP | 0888749 | B1 | 9/2004 |
| EP | 0959786 | B1 | 9/2004 |
| EP | 1459695 | A1 | 9/2004 |
| EP | 1254636 | B1 | 10/2004 |
| EP | 1473819 | A1 | 11/2004 |
| EP | 1477119 | A1 | 11/2004 |
| EP | 1479345 | A1 | 11/2004 |
| EP | 1479347 | A1 | 11/2004 |
| EP | 1479348 | A1 | 11/2004 |
| EP | 0754437 | B2 | 12/2004 |
| EP | 1025807 | B1 | 12/2004 |
| EP | 1001710 | B1 | 1/2005 |
| EP | 1520521 | A1 | 4/2005 |
| EP | 1520522 | A1 | 4/2005 |
| EP | 1520523 | A1 | 4/2005 |
| EP | 1520525 | A1 | 4/2005 |
| EP | 1522264 | A1 | 4/2005 |
| EP | 1523942 | A2 | 4/2005 |
| EP | 1550408 | A1 | 7/2005 |
| EP | 1557129 | A1 | 7/2005 |
| EP | 1064883 | B1 | 8/2005 |
| EP | 1067876 | B1 | 8/2005 |
| EP | 0870473 | B1 | 9/2005 |
| EP | 1157666 | B1 | 9/2005 |
| EP | 0880338 | B1 | 10/2005 |
| EP | 1158917 | B1 | 11/2005 |
| EP | 1344498 | B1 | 11/2005 |
| EP | 0906764 | B1 | 12/2005 |
| EP | 1330989 | B1 | 12/2005 |
| EP | 0771176 | B2 | 1/2006 |
| EP | 1621138 | A2 | 2/2006 |
| EP | 1621139 | A2 | 2/2006 |
| EP | 1621141 | A2 | 2/2006 |
| EP | 1621145 | A2 | 2/2006 |
| EP | 1621151 | A2 | 2/2006 |
| EP | 1034746 | B1 | 3/2006 |
| EP | 1201196 | B1 | 3/2006 |
| EP | 1632191 | A2 | 3/2006 |
| EP | 1647231 | A1 | 4/2006 |
| EP | 1065981 | B1 | 5/2006 |
| EP | 1082944 | B1 | 5/2006 |
| EP | 1652481 | A2 | 5/2006 |
| EP | 1382303 | B1 | 6/2006 |
| EP | 1253866 | B1 | 7/2006 |
| EP | 1032318 | B1 | 8/2006 |
| EP | 1045672 | B1 | 8/2006 |
| EP | 1617768 | B1 | 8/2006 |
| EP | 1693015 | A2 | 8/2006 |
| EP | 1400214 | B1 | 9/2006 |
| EP | 1702567 | A2 | 9/2006 |
| EP | 1129665 | B1 | 11/2006 |
| EP | 1400206 | B1 | 11/2006 |
| EP | 1721568 | A1 | 11/2006 |
| EP | 1256317 | B1 | 12/2006 |
| EP | 1285633 | B1 | 12/2006 |
| EP | 1728473 | A1 | 12/2006 |
| EP | 1728475 | A2 | 12/2006 |
| EP | 1011494 | B1 | 1/2007 |
| EP | 1479346 | B1 | 1/2007 |
| EP | 1484024 | B1 | 1/2007 |
| EP | 1754445 | A2 | 2/2007 |
| EP | 1759812 | A1 | 3/2007 |
| EP | 1767163 | A1 | 3/2007 |
| EP | 1769756 | A1 | 4/2007 |
| EP | 1769758 | A1 | 4/2007 |
| EP | 1581128 | B1 | 5/2007 |
| EP | 1780825 | A1 | 5/2007 |
| EP | 1785097 | A2 | 5/2007 |
| EP | 1790293 | A2 | 5/2007 |
| EP | 1790294 | A1 | 5/2007 |
| EP | 1800610 | A1 | 6/2007 |
| EP | 1300117 | B1 | 8/2007 |
| EP | 1813199 | A1 | 8/2007 |
| EP | 1813200 | A2 | 8/2007 |
| EP | 1813201 | A1 | 8/2007 |
| EP | 1813202 | A1 | 8/2007 |
| EP | 1813203 | A2 | 8/2007 |
| EP | 1813207 | A1 | 8/2007 |
| EP | 1813209 | A1 | 8/2007 |
| EP | 1837041 | A1 | 9/2007 |
| EP | 0922435 | B1 | 10/2007 |
| EP | 1487359 | B1 | 10/2007 |
| EP | 1599146 | B1 | 10/2007 |
| EP | 1839596 | A1 | 10/2007 |
| EP | 2110083 | A2 | 10/2007 |
| EP | 1857057 | A2 | 11/2007 |
| EP | 1402821 | B1 | 12/2007 |
| EP | 1872727 | A1 | 1/2008 |
| EP | 1550410 | B1 | 2/2008 |
| EP | 1671593 | B1 | 2/2008 |
| EP | 1897502 | A1 | 3/2008 |
| EP | 1611856 | B1 | 4/2008 |
| EP | 1908417 | A2 | 4/2008 |
| EP | 1330201 | B1 | 6/2008 |
| EP | 1702568 | B1 | 7/2008 |
| EP | 1943955 | A2 | 7/2008 |
| EP | 1943957 | A2 | 7/2008 |
| EP | 1943964 | A1 | 7/2008 |
| EP | 1943976 | A2 | 7/2008 |
| EP | 1593337 | B1 | 8/2008 |
| EP | 1970014 | A1 | 9/2008 |
| EP | 1980213 | A2 | 10/2008 |
| EP | 1759645 | B1 | 11/2008 |
| EP | 1990014 | A2 | 11/2008 |
| EP | 1552795 | B1 | 12/2008 |
| EP | 1693008 | B1 | 12/2008 |
| EP | 1759640 | B1 | 12/2008 |
| EP | 1997439 | A2 | 12/2008 |
| EP | 2000102 | A2 | 12/2008 |
| EP | 2005894 | A2 | 12/2008 |
| EP | 2005901 | A1 | 12/2008 |
| EP | 2008595 | A2 | 12/2008 |
| EP | 1736104 | B1 | 3/2009 |
| EP | 1749486 | B1 | 3/2009 |
| EP | 1782743 | B1 | 3/2009 |
| EP | 2039302 | A2 | 3/2009 |
| EP | 2039316 | A2 | 3/2009 |
| EP | 1721576 | B1 | 4/2009 |
| EP | 1733686 | B1 | 4/2009 |
| EP | 2044890 | A1 | 4/2009 |
| EP | 1550409 | B1 | 6/2009 |
| EP | 1550413 | B1 | 6/2009 |
| EP | 1719461 | B1 | 6/2009 |
| EP | 1834594 | B1 | 6/2009 |
| EP | 1745748 | B1 | 8/2009 |
| EP | 2090237 | A1 | 8/2009 |
| EP | 2090241 | A1 | 8/2009 |
| EP | 2090244 | A2 | 8/2009 |
| EP | 2090245 | A1 | 8/2009 |
| EP | 2090256 | A2 | 8/2009 |
| EP | 2095777 | A2 | 9/2009 |
| EP | 2098170 | A2 | 9/2009 |
| EP | 2110082 | A1 | 10/2009 |
| EP | 2111803 | A2 | 10/2009 |
| EP | 1813208 | B1 | 11/2009 |
| EP | 1908426 | B1 | 11/2009 |
| EP | 2116195 | A1 | 11/2009 |
| EP | 1607050 | B1 | 12/2009 |
| EP | 1815804 | B1 | 12/2009 |
| EP | 1875870 | B1 | 12/2009 |
| EP | 2151204 | A1 | 2/2010 |
| EP | 2165660 | A2 | 3/2010 |
| EP | 1566150 | B1 | 4/2010 |
| EP | 1813206 | B1 | 4/2010 |
| EP | 1769754 | B1 | 6/2010 |
| EP | 1854416 | B1 | 6/2010 |
| EP | 2198787 | A1 | 6/2010 |
| EP | 1647286 | B1 | 9/2010 |
| EP | 1825821 | B1 | 9/2010 |
| EP | 1535565 | B1 | 10/2010 |
| EP | 1702570 | B1 | 10/2010 |
| EP | 1785098 | B1 | 10/2010 |

(56) References Cited

FOREIGN PATENT DOCUMENTS

| | | | |
|---|---|---|---|
| EP | 2005896 B1 | 10/2010 |
| EP | 2030578 B1 | 11/2010 |
| EP | 1627605 B1 | 12/2010 |
| EP | 2130498 B1 | 12/2010 |
| EP | 1994890 B1 | 1/2011 |
| EP | 2286738 A2 | 2/2011 |
| EP | 1690502 B1 | 3/2011 |
| EP | 2292153 A1 | 3/2011 |
| EP | 1769755 B1 | 4/2011 |
| EP | 2090240 B1 | 4/2011 |
| EP | 2305135 A1 | 4/2011 |
| EP | 1813205 B1 | 6/2011 |
| EP | 2090243 B1 | 6/2011 |
| EP | 2329773 A1 | 6/2011 |
| EP | 1908414 B1 | 11/2011 |
| EP | 2153781 B1 | 11/2011 |
| EP | 1847225 B1 | 12/2011 |
| EP | 1785102 B1 | 1/2012 |
| EP | 2090253 B1 | 3/2012 |
| EP | 1813204 B1 | 7/2012 |
| EP | 2005895 B1 | 8/2012 |
| EP | 2090248 B1 | 8/2012 |
| EP | 2090252 B1 | 10/2012 |
| EP | 2517637 A1 | 10/2012 |
| EP | 2517645 A2 | 10/2012 |
| EP | 2517649 A2 | 10/2012 |
| EP | 2517651 A2 | 10/2012 |
| EP | 1884206 B1 | 3/2013 |
| FR | 459743 A | 11/1913 |
| FR | 999646 A | 2/1952 |
| FR | 1112936 A | 3/1956 |
| FR | 2598905 A1 | 11/1987 |
| FR | 2765794 A | 1/1999 |
| GB | 939929 A | 10/1963 |
| GB | 1210522 A | 10/1970 |
| GB | 1217159 A | 12/1970 |
| GB | 1339394 A | 12/1973 |
| GB | 2109241 A | 6/1983 |
| GB | 2272159 A | 5/1994 |
| GB | 2284242 A | 5/1995 |
| GB | 2336214 A | 10/1999 |
| GB | 2425903 A | 11/2006 |
| GR | 930100110 A | 11/1993 |
| JP | 50-33988 U | 4/1975 |
| JP | S 58500053 A | 1/1983 |
| JP | 61-98249 A | 5/1986 |
| JP | S 61502036 A | 9/1986 |
| JP | S 63-59764 A | 3/1988 |
| JP | S 63-147449 A | 6/1988 |
| JP | 63-203149 | 8/1988 |
| JP | H 02-279149 A | 11/1990 |
| JP | 3-12126 A | 1/1991 |
| JP | H 05-084252 A | 4/1993 |
| JP | 5-212039 A | 8/1993 |
| JP | 6007357 A | 1/1994 |
| JP | H 6-30945 A | 2/1994 |
| JP | H 06-26812 U | 4/1994 |
| JP | H 6-121798 A | 5/1994 |
| JP | 7051273 A | 2/1995 |
| JP | 7-124166 A | 5/1995 |
| JP | 07-171163 | 7/1995 |
| JP | 7-255735 A | 10/1995 |
| JP | 8-33642 A | 2/1996 |
| JP | 8033641 A | 2/1996 |
| JP | 8-164141 A | 6/1996 |
| JP | H 08-182684 A | 7/1996 |
| JP | H 08-507708 A | 8/1996 |
| JP | 8229050 A | 9/1996 |
| JP | H 09-501081 A | 2/1997 |
| JP | H 09-501577 A | 2/1997 |
| JP | 10-512469 | 12/1998 |
| JP | 2000-14632 | 1/2000 |
| JP | 2000033071 A | 2/2000 |
| JP | 2000-112002 A | 4/2000 |
| JP | 2000171730 A | 6/2000 |
| JP | 2000287987 A | 10/2000 |
| JP | 2000325303 A | 11/2000 |
| JP | 2001-514541 | 9/2001 |
| JP | 2001-517473 A | 10/2001 |
| JP | 2001286477 A | 10/2001 |
| JP | 2002143078 A | 5/2002 |
| JP | 2002369820 A | 12/2002 |
| JP | 2003-500153 A | 1/2003 |
| JP | 2003-164066 | 6/2003 |
| JP | 2003-521301 A | 7/2003 |
| JP | 2004-162035 A | 6/2004 |
| JP | 2004-229976 A | 8/2004 |
| JP | 2004-531280 A | 10/2004 |
| JP | 2004-532084 A | 10/2004 |
| JP | 2004-329624 A | 11/2004 |
| JP | 2004-344663 | 12/2004 |
| JP | 2005-028147 A | 2/2005 |
| JP | 2005-28148 A | 2/2005 |
| JP | 2005-028149 A | 2/2005 |
| JP | 2005-505309 A | 2/2005 |
| JP | 2005505322 T | 2/2005 |
| JP | 2005-103280 A | 4/2005 |
| JP | 2005-103281 A | 4/2005 |
| JP | 2005-511131 A | 4/2005 |
| JP | 2005103293 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005-144183 A | 6/2005 |
| JP | 2005-516714 A | 6/2005 |
| JP | 2005137423 A | 6/2005 |
| JP | 2005152416 A | 6/2005 |
| JP | 2005-523105 A | 8/2005 |
| JP | 2005524474 A | 8/2005 |
| JP | 2005-335432 A | 12/2005 |
| JP | 2006-034975 A | 2/2006 |
| JP | 2006-34977 A | 2/2006 |
| JP | 2006-034980 A | 2/2006 |
| JP | 2006-506106 A | 2/2006 |
| JP | 2006-187649 A | 7/2006 |
| JP | 2006-218297 A | 8/2006 |
| JP | 2006-281405 A | 10/2006 |
| JP | 2006-346445 A | 12/2006 |
| JP | 2007-61628 A | 3/2007 |
| JP | 2007-098130 A | 4/2007 |
| JP | 3906843 B2 | 4/2007 |
| JP | 2007-117725 A | 5/2007 |
| JP | 2007-222615 A | 6/2007 |
| JP | 2007-203051 A | 8/2007 |
| JP | 2007-203057 A | 8/2007 |
| JP | 2007/524435 A | 8/2007 |
| JP | 2007-229448 A | 9/2007 |
| JP | 2007-325922 A | 12/2007 |
| JP | 2008-68073 A | 3/2008 |
| JP | 2008-283459 A | 11/2008 |
| JP | 2009-506799 A | 2/2009 |
| JP | 2009-106752 A | 5/2009 |
| JP | 2009-539420 A | 11/2009 |
| JP | 2010-098844 A | 4/2010 |
| RU | 1814161 A1 | 5/1993 |
| RU | 2008830 C1 | 3/1994 |
| RU | 2141279 C1 | 11/1999 |
| RU | 2187249 C2 | 8/2002 |
| RU | 2189091 C2 | 9/2002 |
| RU | 32984 U1 | 10/2003 |
| RU | 2225170 C2 | 3/2004 |
| RU | 42750 U1 | 12/2004 |
| RU | 61114 U1 | 2/2007 |
| SU | 189517 A | 1/1967 |
| SU | 328636 A | 9/1972 |
| SU | 674747 A1 | 7/1979 |
| SU | 886900 A1 | 12/1981 |
| SU | 1009439 A | 4/1983 |
| SU | 1022703 A1 | 6/1983 |
| SU | 1333319 A2 | 8/1987 |
| SU | 1377053 A1 | 2/1988 |
| SU | 1509051 A1 | 9/1989 |

(56) References Cited

FOREIGN PATENT DOCUMENTS

| | | |
|---|---|---|
| SU | 1561964 A1 | 5/1990 |
| SU | 1708312 A1 | 1/1992 |
| SU | 1722476 A1 | 3/1992 |
| SU | 1752361 A1 | 8/1992 |
| WO | WO 82/02824 A1 | 9/1982 |
| WO | WO 86/02254 A1 | 4/1986 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/18893 A1 | 9/1994 |
| WO | WO 94/20030 A1 | 9/1994 |
| WO | WO 94/22378 A1 | 10/1994 |
| WO | WO 94/23659 A1 | 10/1994 |
| WO | WO 94/24943 A1 | 11/1994 |
| WO | WO 94-24947 A1 | 11/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/18344 A2 | 6/1996 |
| WO | WO 96/19151 A1 | 6/1996 |
| WO | WO 96/19152 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/01989 A1 | 1/1997 |
| WO | WO 97/06582 A1 | 2/1997 |
| WO | WO 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/34533 A1 | 9/1997 |
| WO | WO 97/37598 A1 | 10/1997 |
| WO | WO 97/39688 A2 | 10/1997 |
| WO | WO 98/17180 A1 | 4/1998 |
| WO | WO 98/27880 A1 | 7/1998 |
| WO | WO 98/30153 A1 | 7/1998 |
| WO | WO 98/47436 A1 | 10/1998 |
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/03587 A1 | 1/2001 |
| WO | WO 01/05702 A1 | 1/2001 |
| WO | WO 01/10482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/80757 A2 | 11/2001 |
| WO | WO 01/91646 A1 | 12/2001 |
| WO | WO 02/00121 A1 | 1/2002 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/013372 A2 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/086206 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |

(56) References Cited

FOREIGN PATENT DOCUMENTS

| | | |
|---|---|---|
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/019769 A1 | 3/2004 |
| WO | WO 2004/019803 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/078236 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/023486 A1 | 3/2006 |
| WO | WO 2006/023578 A2 | 3/2006 |
| WO | WO 2006/027014 A1 | 3/2006 |
| WO | WO 2006/028314 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/089603 A2 | 8/2007 |
| WO | WO 2007/098220 A2 | 8/2007 |
| WO | WO 2007/121579 A1 | 11/2007 |
| WO | WO 2007/131110 A2 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/147439 A1 | 12/2007 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/057281 A2 | 5/2008 |
| WO | WO 2008/070763 A1 | 6/2008 |
| WO | WO 2008/089404 A2 | 7/2008 |
| WO | WO 2008/101080 A1 | 8/2008 |
| WO | WO 2008/109125 A1 | 9/2008 |
| WO | WO 2008/124748 A1 | 10/2008 |
| WO | WO 2009/023851 A1 | 2/2009 |
| WO | WO 2009/046394 A1 | 4/2009 |
| WO | WO 2009/137761 A2 | 11/2009 |
| WO | WO 2009/143092 A1 | 11/2009 |
| WO | WO 2009/143331 A1 | 11/2009 |
| WO | WO 2010/028332 A2 | 3/2010 |
| WO | WO 2010/030434 A1 | 3/2010 |
| WO | WO 2010/054404 A1 | 5/2010 |
| WO | WO 2010/063795 A1 | 6/2010 |
| WO | WO 2010/098871 A2 | 9/2010 |
| WO | WO 2012/021671 A1 | 2/2012 |
| WO | WO 2012/044551 A1 | 4/2012 |
| WO | WO 2012/044820 A1 | 4/2012 |
| WO | WO 2012/044844 A2 | 4/2012 |

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, 2000, 3 pages.

"Biomedical Coatings," Fort Wayne Metals, Research Products Corporation, obtained online at www.fwmetals.com on Jun. 21, 2010 (1 page).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

ASTM procedure D2240-00, "Standard Test Method for Rubber Property-Durometer Hardness," (Published Aug. 2000).

ASTM procedure D2240-05, "Standard Test Method for Rubber Property-Durometer Hardness," (Published Apr. 2010).

Covidien Brochure, "Endo GIA™ Reloads with Tri-Staple™ Technology," (2010), 1 page.

Covidien Brochure, "Endo GIA™ Reloads with Tri-Staple™ Technology and Endo GIA™ Ultra Universal Staplers," (2010), 2 pages.

Covidien Brochure, "Endo GIA™ Black Reload with Tri-Stapler™ Technology," (2012), 2 pages.

Covidien Brochure, "Endo GIA™ Curved Tip Reload with Tri-Staple™ Technology," (2012), 2 pages.

Covidien Brochure, "Endo GIA™ Reloads with Tri-Staple™ Technology," (2010), 2 pages.

Covidien Brochure, "Endo GIA™ Ultra Universal Stapler," (2010), 2 pages.

Miyata et al., "Biomolecule-Sensitive Hydrogels," Advanced Drug Delivery Reviews, 54 (2002) pp. 79-98.

Jeong et al., "Thermosensitive Sol-Gel Reversible Hydrogels," Advanced Drug Delivery Reviews, 54 (2002) pp. 37-51.

(56) References Cited

OTHER PUBLICATIONS

Byrne et al., "Molecular Imprinting Within Hydrogels," Advanced Drug Delivery Reviews, 54 (2002) pp. 149-161.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 30-12.
Hoffman, "Hydrogels for Biomedical Applications," Advanced Drug Delivery Reviews, 54 (2002) pp. 30-12.
Peppas, "Physiologically Responsive Hydrogels," Journal of Bioactive and Compatible Polymers, vol. 6 (Jul. 1991) pp. 241-246.
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
Peppas, Editor "Hydrogels in Medicine and Pharmacy," vol. I, Fundamentals, CRC Press, 1986.
International Search Report for PCT/US2012/052751, dated Nov. 23, 2012 (3 pages).

* cited by examiner

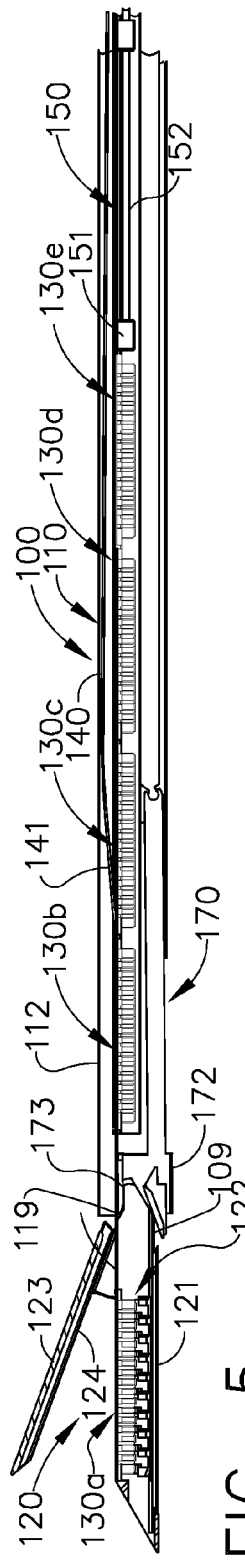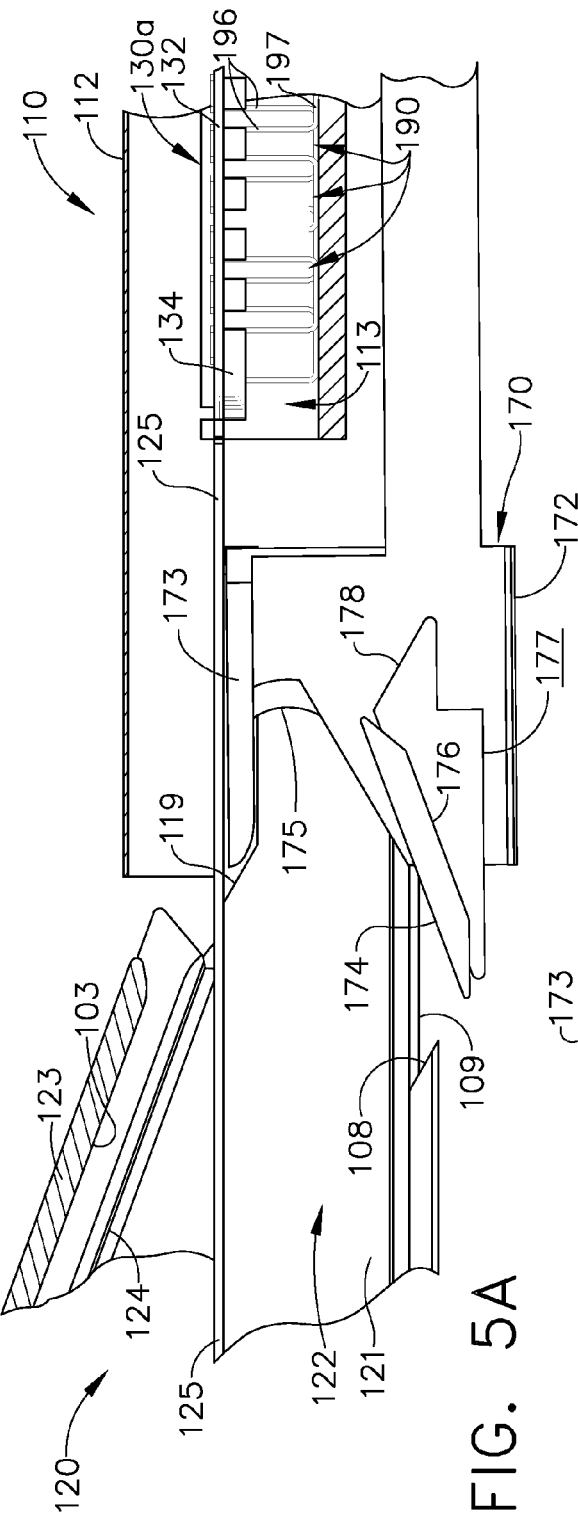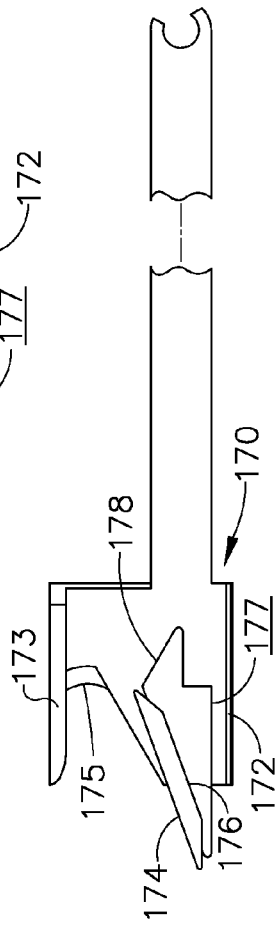

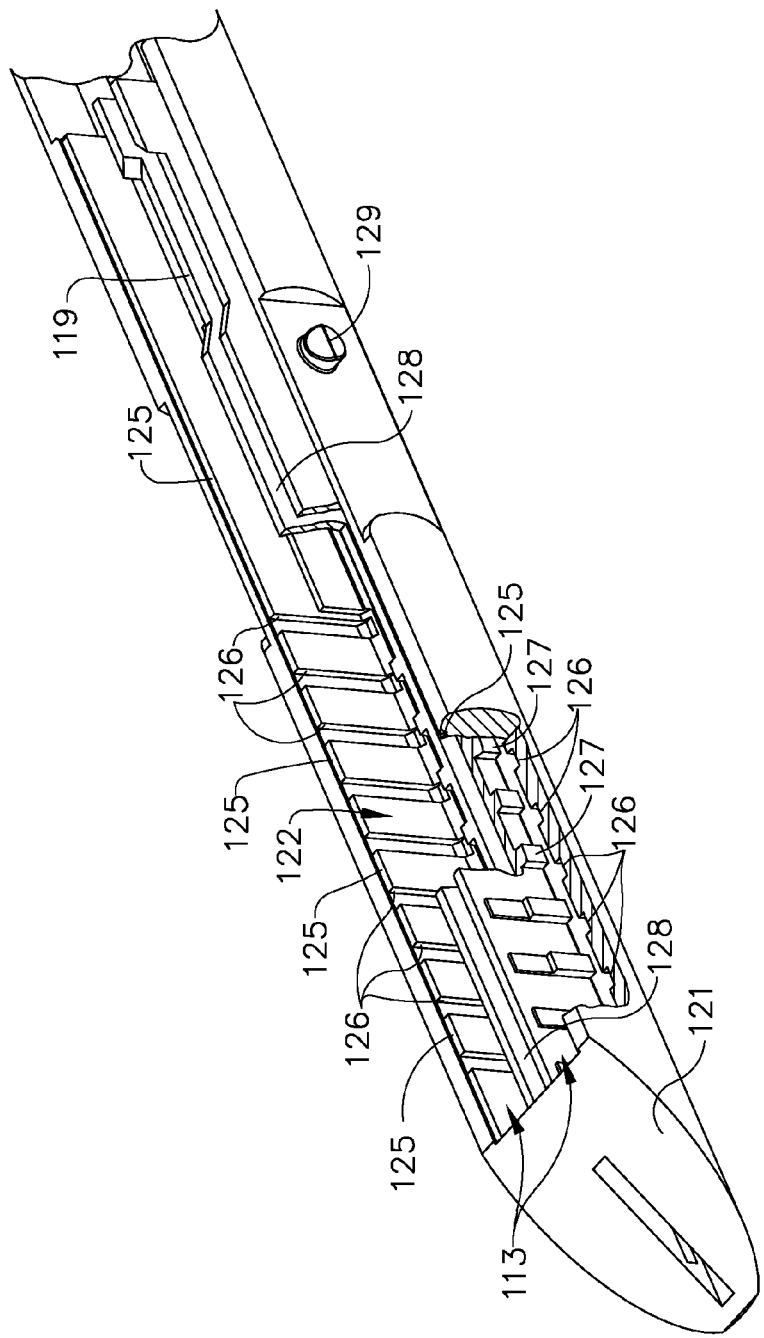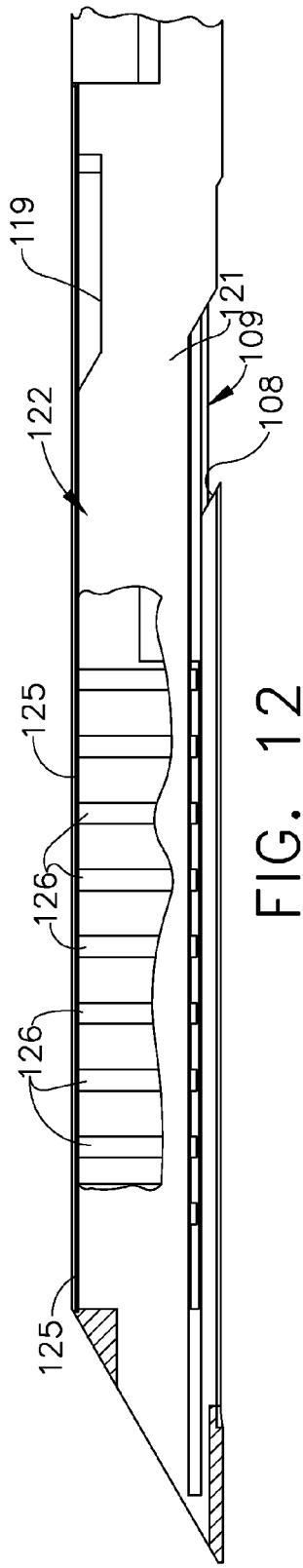

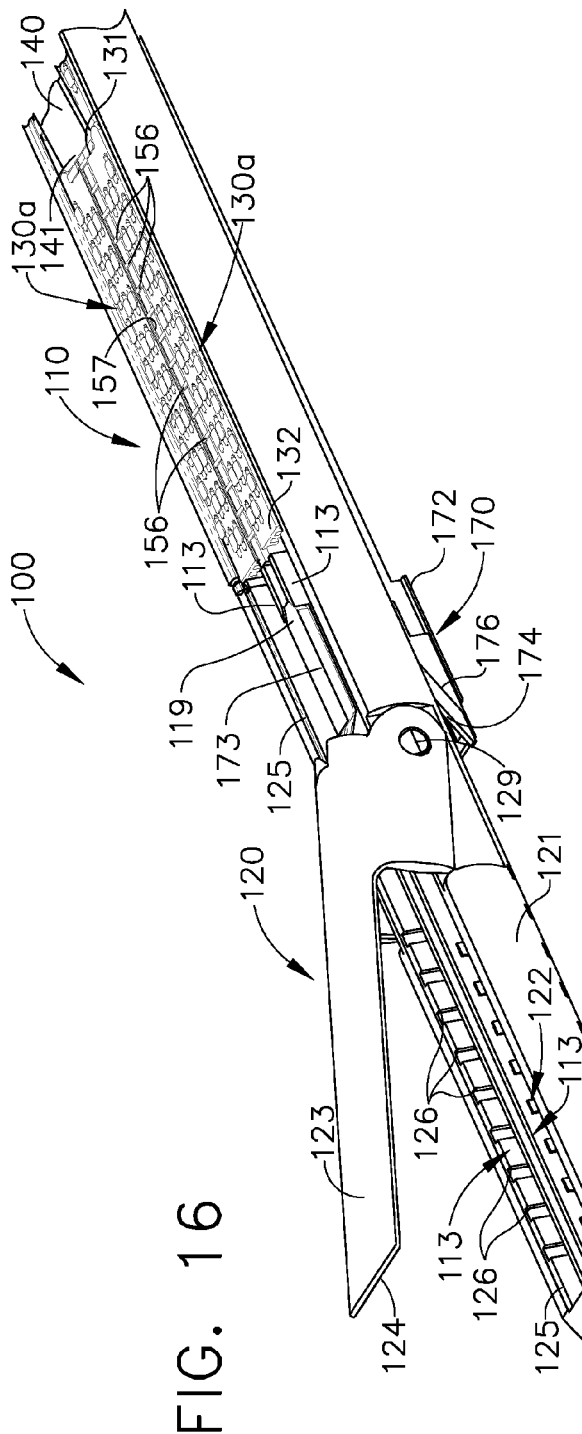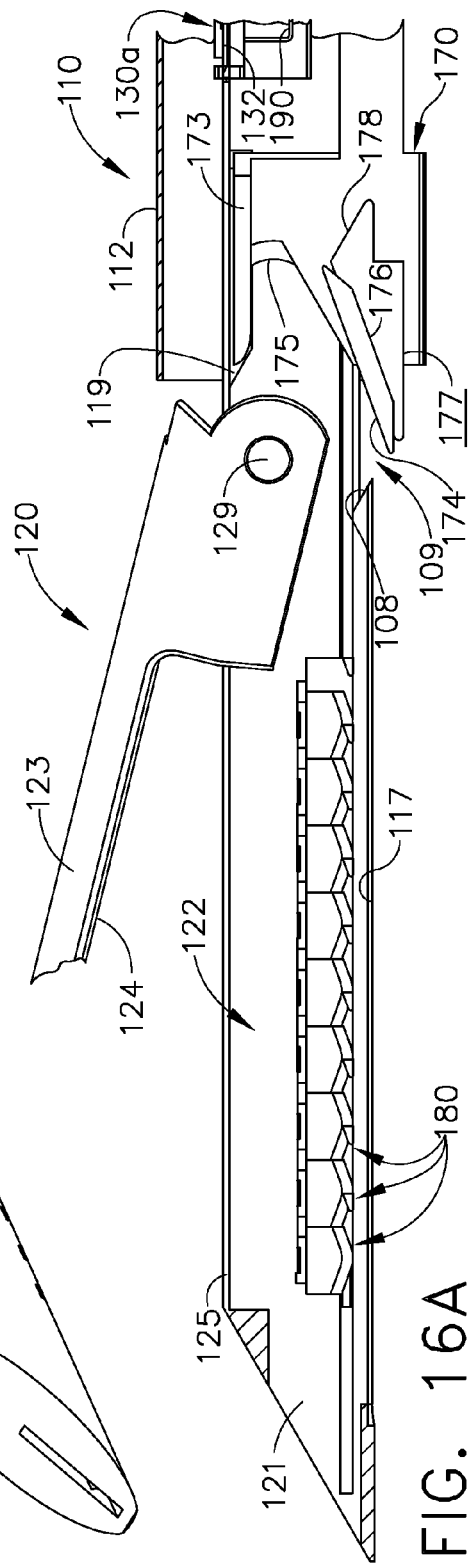

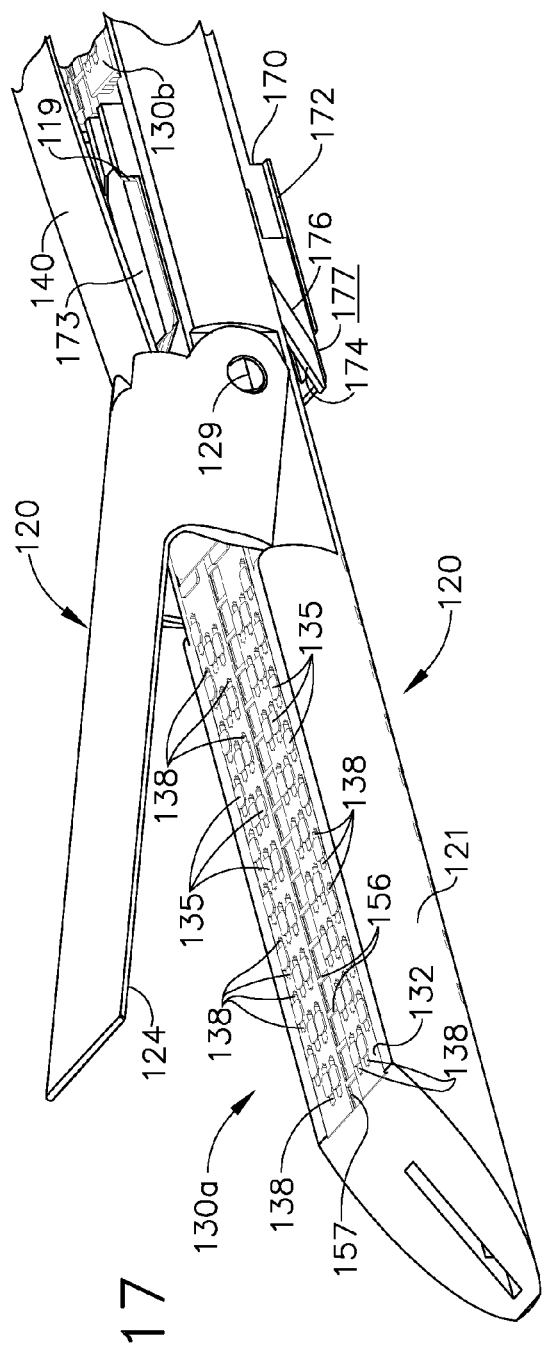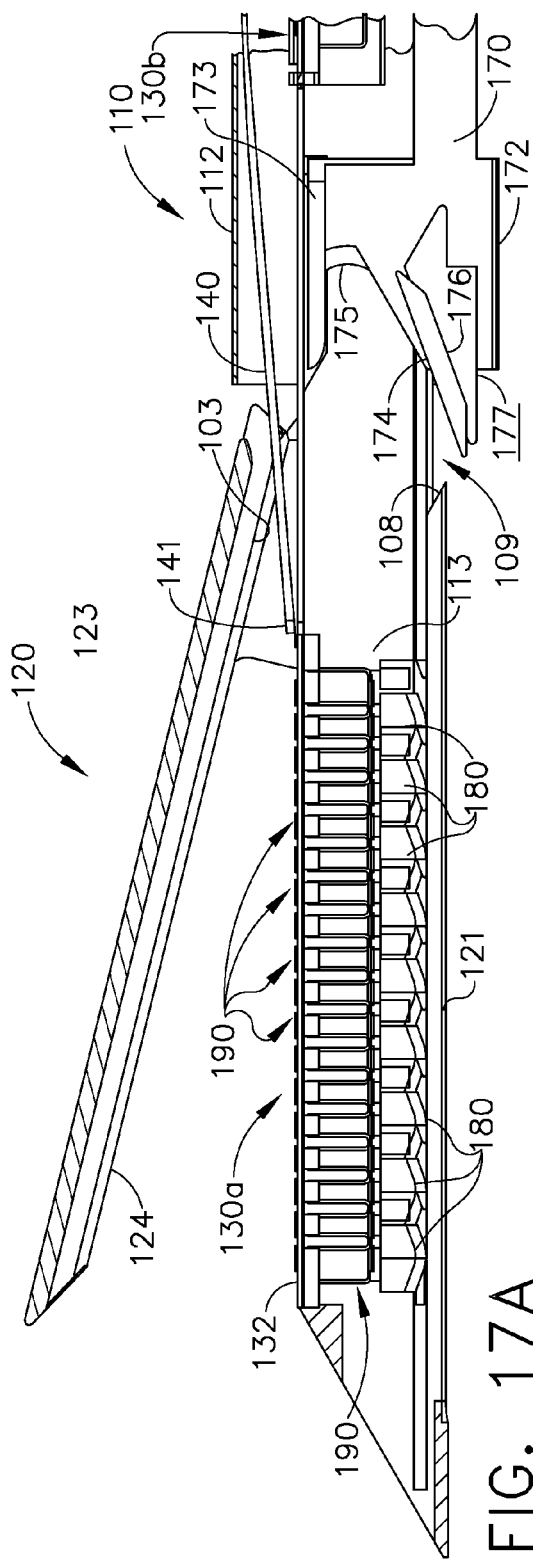

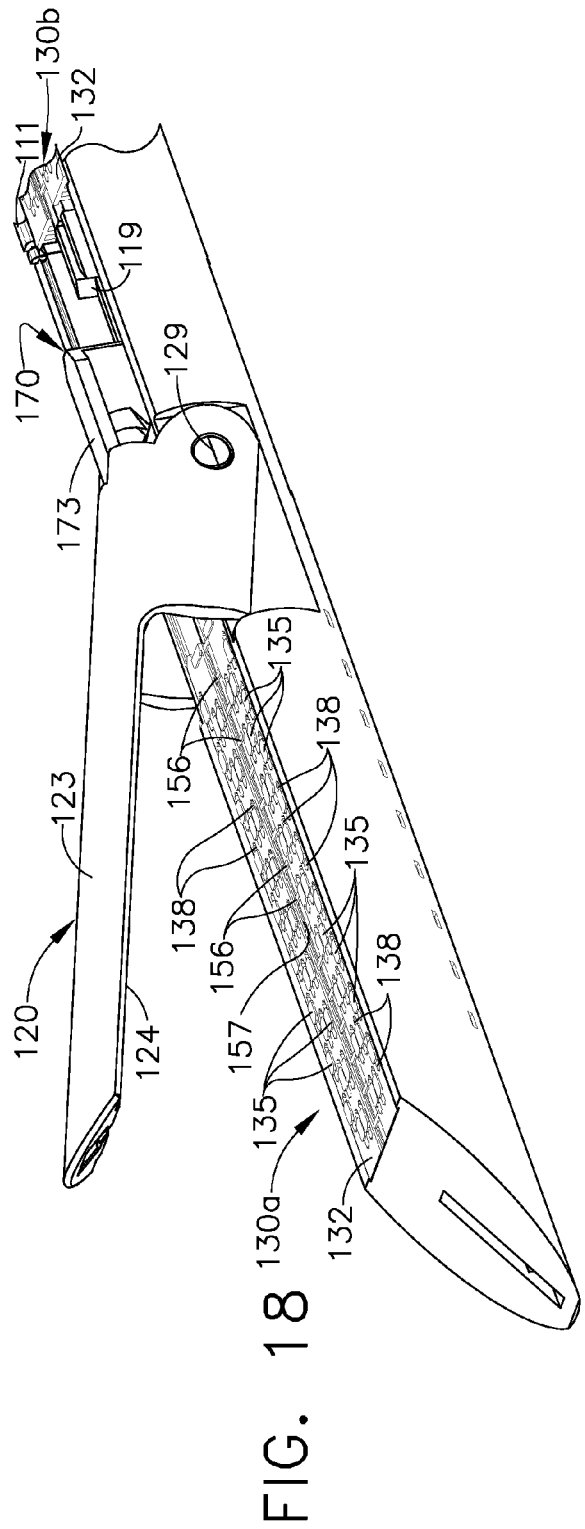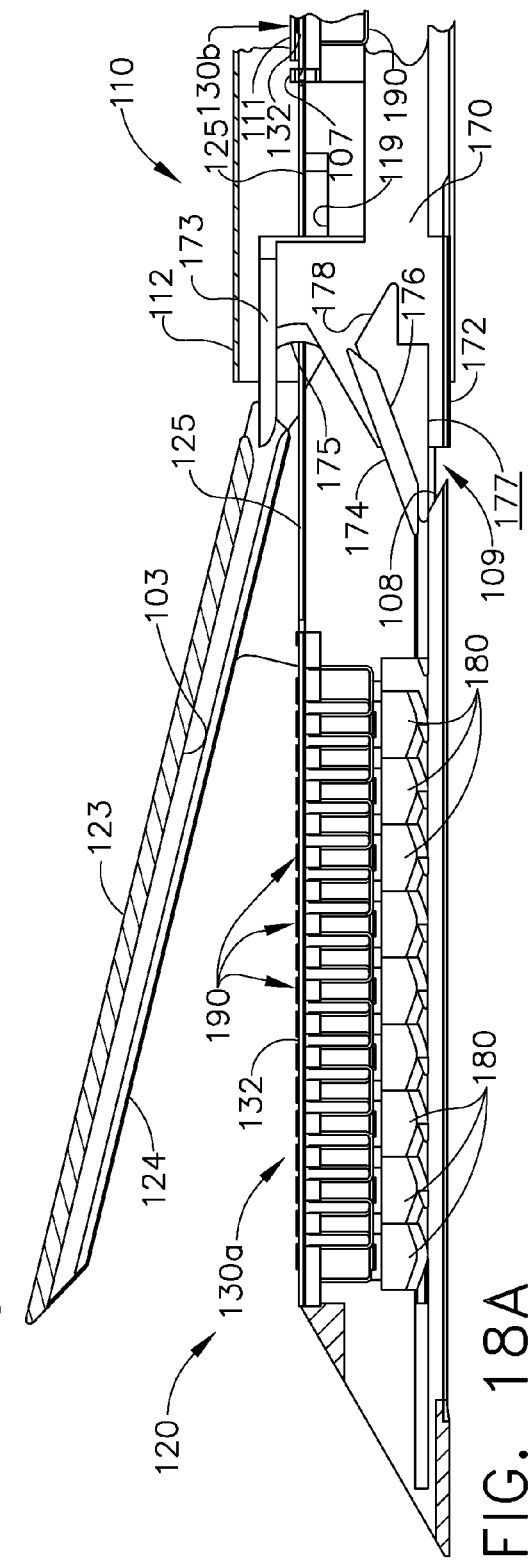

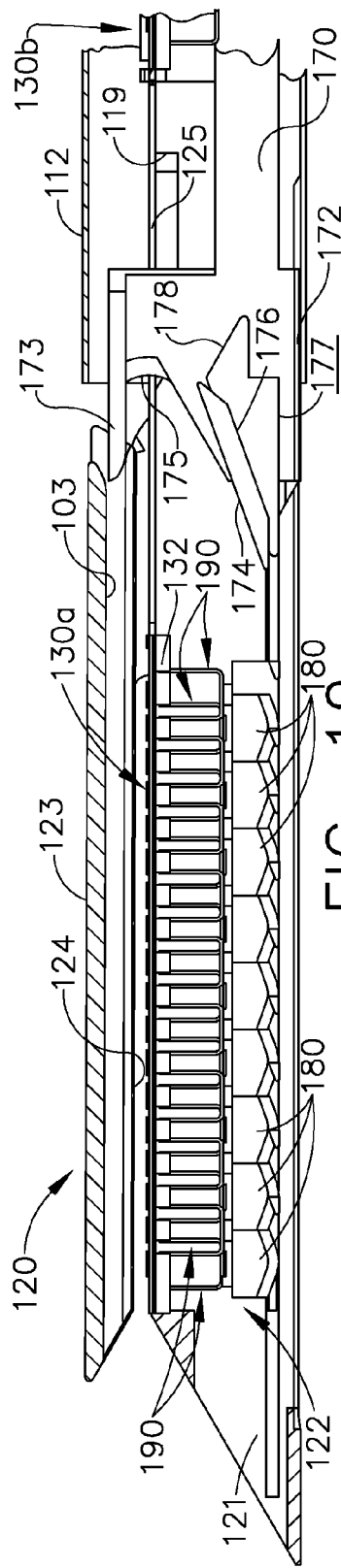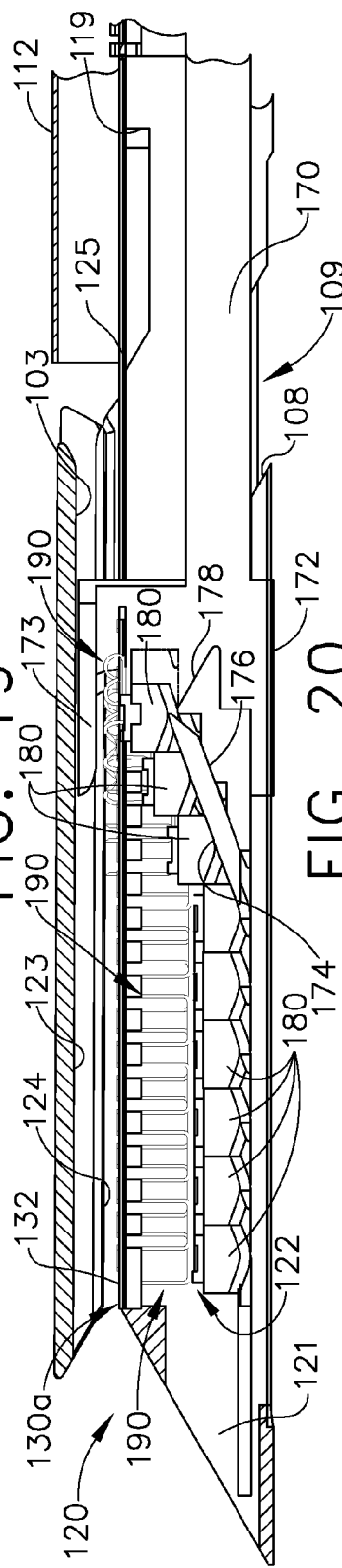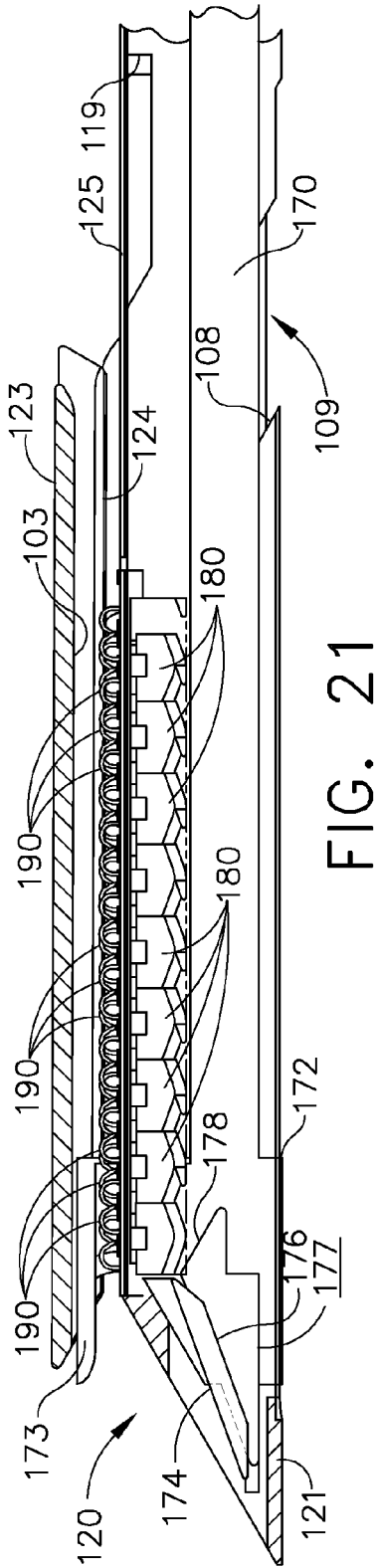

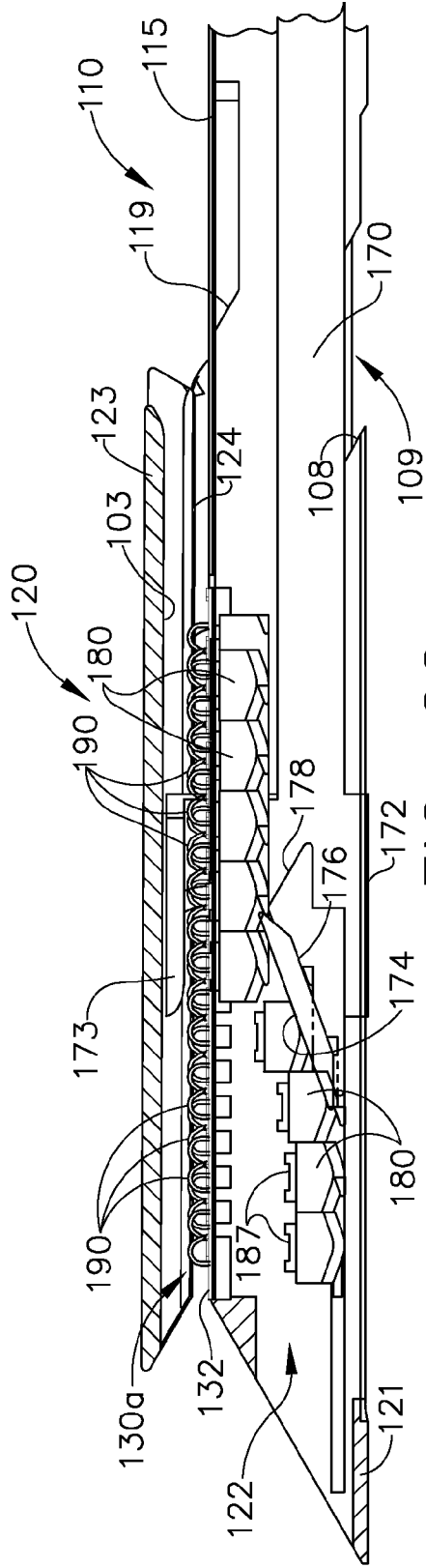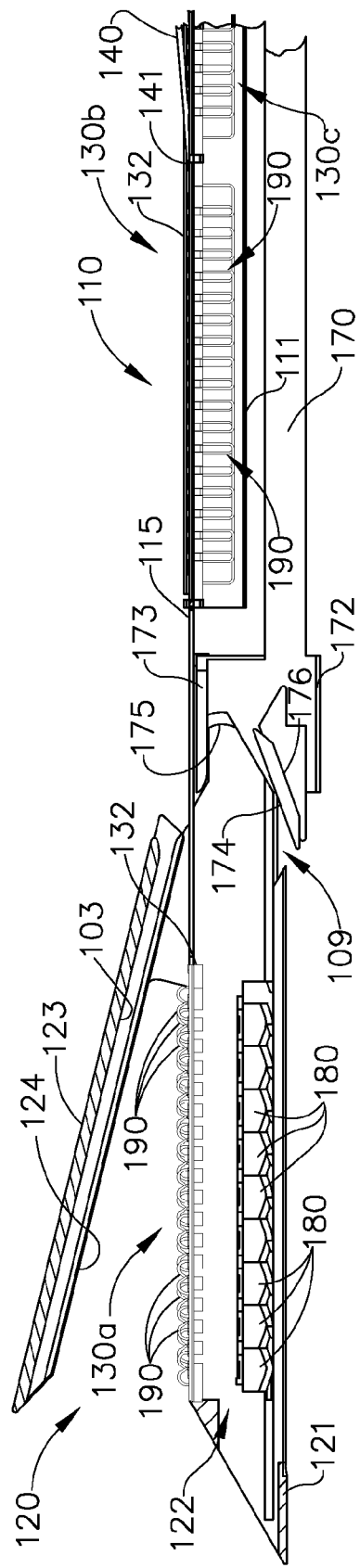

STAPLING INSTRUMENT COMPRISING A PLURALITY OF STAPLE CARTRIDGES STORED THEREIN

BACKGROUND

With regard to previous surgical stapling instruments, a surgical stapling instrument could include a handle, a shaft, and an end effector, wherein the end effector could be inserted into a surgical site within a patient to staple and/or incise tissue located within the surgical site. In various embodiments, the end effector could be configured to receive a staple cartridge wherein, after the staple cartridge had been at least partially expended, the staple cartridge could be removed from the end effector and replaced with a new, unspent staple cartridge. In order to replace the staple cartridge, in various circumstances, the end effector had to be removed from the surgical site. While suitable for their intended purpose, such procedures required considerable time to perform. Disclosed herein are improvements over the foregoing; however, this discussion of previous surgical stapling instruments is not intended to limit the scope of the claims in any way.

SUMMARY

In at least one form, a surgical stapling instrument can comprise a handle comprising a trigger, a shaft extending from the handle, wherein the shaft comprises a displacing cam, and a plurality of staple cartridges positioned within the shaft, wherein each staple cartridge comprises a cartridge body comprising a plurality of apertures; and a plurality of staples each comprising at least one staple leg positioned in an aperture, wherein the staple legs are slidable within the apertures. The surgical stapling instrument can further comprise a first jaw comprising a channel configured to receive a staple cartridge, wherein the first jaw comprises a plurality of staple drivers positioned within the channel, and wherein the firing member is configured to engage the staple drivers and move the staple drivers between a first position and a second position, and a second jaw comprising an anvil, wherein the staple legs are configured to contact the anvil when the staples are driven into their second position. The surgical stapling instrument can further comprise a cartridge driver configured to sequentially advance the staple cartridges into the channel and a firing member operably coupled with the trigger such that a firing motion can be transferred from the trigger to the firing member to move the firing member along a firing path, wherein the firing path comprises, one, a proximal position in which the firing member is in contact with the displacing cam and is displaced in a transverse direction with respect to the firing path, wherein a staple cartridge can slide past the firing member when the firing member is displaced in the transverse direction, two, a plurality of firing positions in which the firing member is in contact with the staple drivers, and, three, a distal position.

In at least one form, a surgical stapling instrument assembly can comprise a shaft including a removable magazine and a displacing cam and a plurality of staple cartridges positioned within the magazine, wherein each staple cartridge comprises cartridge body comprising a plurality of apertures and a plurality of staples each comprising a staple leg positioned in an aperture, wherein the staple legs are slidable within the apertures. The surgical stapling instrument can further comprise a first jaw comprising a channel configured to receive a staple cartridge, a second jaw comprising an anvil, wherein the staple legs are configured to contact the anvil, a cartridge driver configured to sequentially advance the staple cartridges into the channel; and a firing member configured to be moved along a firing path, wherein the firing path comprises a proximal position in which the firing member is in contact with the displacing cam and is displaced in a transverse direction with respect to the firing path, wherein a staple cartridge can slide past the firing member when the firing member is displaced in the transverse direction, and a plurality of firing positions in which the firing member drives the staples against the anvil.

In at least one form, a surgical stapling instrument can comprise a shaft comprising a frame and a plurality of staple cartridges positioned within the shaft, wherein each staple cartridge comprises a cartridge body comprising a plurality of apertures and a plurality of staples each comprising a staple leg positioned in an aperture, wherein the staple legs are slidable within the apertures. The surgical stapling instrument can further comprise a first jaw comprising a channel configured to receive a staple cartridge, a second jaw comprising an anvil, wherein the staple legs are configured to contact the anvil, a cartridge driver configured to sequentially advance the staple cartridges into the channel, and a firing member configured to be moved along a firing path, wherein the firing path comprises a proximal position in which the firing member is in contact with the frame and is displaced downwardly with respect to the firing path, wherein a staple cartridge can slide past the firing member when the firing member is displaced in the downward direction and a plurality of firing positions in which the firing member drives the staples against the anvil.

In at least one form, a surgical stapling instrument can comprise a handle including a trigger, a shaft extending from the handle, and a firing member operably coupled with the trigger such that a firing motion can be transferred from the trigger to the firing member to move the firing member along a firing path. The surgical stapling instrument can further comprise a plurality of staple cartridges positioned within the shaft, wherein each staple cartridge comprises a cartridge body and a plurality of staples, and a first jaw comprising a proximal end extending from the shaft, a distal end, a channel configured to receive a staple cartridge, and a plurality of staple drivers, wherein the firing member is configured to engage the staple drivers and move each staple driver from an undeployed position into a deployed position as the firing member is moved from the proximal end to the distal end, and wherein the firing member is configured to engage the staple drivers and move the staple drivers from the deployed position into the undeployed position as the firing member is moved from the distal end to the proximal end. The surgical stapling instrument can further comprise a second jaw comprising an anvil, wherein the staples are configured to contact the anvil when the staples are deployed, and a cartridge driver configured to sequentially advance a staple cartridge into the channel.

In at least one form, a surgical stapling instrument assembly can comprise a shaft, a plurality of staple cartridges positioned within the shaft, wherein each staple cartridge comprises a cartridge body and a plurality of staples, and a firing member configured to move along a firing path. The surgical stapling instrument assembly can further comprise a first jaw including a proximal portion attached to the shaft, a distal portion, a channel configured to receive a staple cartridge, and a plurality of staple drivers, wherein the firing member is configured to engage the staple drivers and move each staple driver from a first position into a second position as the firing member is moved from the proximal portion to the distal portion, and wherein the firing member is configured to engage the staple drivers and move the staple drivers from the second position into the first position as the firing member is moved from the distal portion to the proximal portion. The surgical stapling instrument assembly can further comprise, one, a second jaw comprising an anvil, wherein the staples are configured to contact the anvil when the staples are deployed, and, two, a cartridge driver configured to sequentially advance a staple cartridge into the channel.

In at least one form, a surgical stapling instrument can comprise, one, a shaft configured to store a plurality of staple cartridges, wherein each staple cartridge comprises a cartridge body, a plurality of staples, and a tissue contacting surface and, two, a firing member configured to move along a firing path. The instrument can further include a first jaw comprising a proximal portion attached to the shaft, a distal portion, and a plurality of staple drivers, wherein the firing member is configured to engage the staple drivers and lift each staple driver toward the tissue contacting surface as the firing member is moved between the proximal portion and the distal portion, and wherein the firing member is configured to engage the staple drivers and lower the staple drivers away from the tissue contacting surface as the firing member is moved between the distal portion and the proximal portion. The instrument can further include a second jaw comprising an anvil, wherein the staples are configured to contact the anvil when the staple drivers are lifted toward the tissue-contacting surface, and a cartridge driver configured to sequentially advance a staple cartridge into the first jaw.

In at least one form, a surgical stapling instrument can comprise a handle comprising a trigger, a shaft extending distally from the handle, and a firing member operably coupled with the trigger such that a firing motion can be transferred from the trigger to the firing member to move the firing member along a firing path. The instrument can further comprise a first staple cartridge positioned within the shaft comprising a first cartridge body comprising a plurality of first apertures and a plurality of first staples each comprising at least one first staple leg positioned in a first aperture, wherein the first staple legs are slidable within the first apertures, and wherein the first staple legs comprise a first length, and a second staple cartridge positioned within the shaft comprising a second cartridge body comprising a plurality of second apertures and a plurality of second staples each comprising at least one second staple leg positioned in a second aperture, wherein the second staple legs are slidable within the second apertures, and wherein the second staple legs comprise a second length which is different than the first length. The instrument can further comprise a first jaw comprising a channel configured to receive a staple cartridge, a second jaw comprising an anvil configured to deform the staples, and a cartridge driver configured to sequentially advance the first and second staple cartridges into the channel from a staging position.

In at least one form, a surgical stapling instrument assembly can comprise a shaft comprising a removable magazine, a firing member movable along a firing path, and a first staple cartridge positioned within the magazine, wherein the first staple cartridge comprises a first cartridge body comprising a plurality of first apertures and a plurality of first staples each comprising a first staple leg positioned in a first aperture, wherein the first staple legs are slidable within the first apertures, and wherein the first staples each comprise a first height. The instrument assembly further comprises a second staple cartridge positioned within the magazine, wherein the second staple cartridge comprises a second cartridge body comprising a plurality of second apertures and a plurality of second staples each comprising a second staple leg positioned in a second aperture, wherein the second staple legs are slidable within the second apertures, and wherein the second staples comprise a second height which is different than the first height. The instrument assembly can further include a first jaw comprising a channel configured to receive a staple cartridge, a second jaw comprising an anvil configured to deform the staples, and a cartridge driver configured to sequentially advance the first and second staple cartridges into the channel from a staging position.

In at least one form, a surgical stapling instrument can comprise a shaft, a firing member movable along a firing path, a first staple cartridge positioned within the shaft, wherein the first staple cartridge comprises a first cartridge body and a plurality of first staples, and wherein the first staples each comprise a first height, and a second staple cartridge positioned within the shaft, wherein the second staple cartridge comprises a second cartridge body and a plurality of second staples, wherein the second staples each comprise a second height which is different than the first height. The instrument can further comprise a first jaw comprising a channel configured to receive a staple cartridge, a second jaw comprising an anvil configured to deform the staples, and a cartridge driver configured to sequentially advance the first and second staple cartridges into the channel.

In at least one form, a surgical stapling instrument can comprise a handle comprising a trigger, a shaft extending from the handle, a firing member operably coupled with the trigger such that a firing motion can be transferred from the trigger to the firing member to move the firing member along a firing path, and a plurality of staple cartridges positioned within the shaft, wherein each staple cartridge comprises a cartridge body comprising a plurality of apertures and a plurality of staples each comprising a staple leg positioned in an aperture, wherein the staple legs are slidable within the apertures. The instrument can further comprise a first jaw comprising a channel configured to receive a staple cartridge, wherein the first jaw comprises a plurality of staple drivers positioned therein, and wherein the firing member is configured to engage the staple drivers and move the staple drivers between a first position and a second position. The instrument can further comprise a second jaw comprising an anvil, wherein the staple legs are configured to contact the anvil when the staples are driven into the second position, a cartridge driver configured to sequentially advance a staple cartridge into the channel from a staging position, and a biasing member configured to sequentially advance a staple cartridge into the staging position.

In at least one form, a surgical stapling instrument assembly can comprise a shaft comprising a removable magazine, a firing member operably couplable with an actuator such that a firing motion can be transferred from the actuator to the firing member to move the firing member along a firing path, and a plurality of staple cartridges positionable within the magazine, wherein each staple cartridge comprises a cartridge body comprising a plurality of apertures and a plurality of staples each comprising a staple leg positioned in an aperture, and wherein the staple legs are slidable within the apertures. The instrument assembly can further comprise a first jaw comprising a channel configured to receive a staple cartridge, wherein the first jaw comprises a plurality of staple drivers positioned therein, and wherein the firing member is configured to engage the staple drivers and move the staple drivers between a first position and a second position. The instrument assembly can further comprise a second jaw comprising an anvil, wherein the staple legs are configured to contact the anvil when the staples are driven into the second position, a cartridge driver configured to sequentially advance a staple cartridge into the channel from a staging position, and a biasing member configured to sequentially advance a staple cartridge into the staging position.

In at least one form, a surgical stapling instrument can comprise a handle comprising a trigger, a shaft extending from the handle, and a firing member operably coupled with the trigger such that a firing motion can be transferred from the trigger to the firing member to move the firing member along a firing path. The instrument can further include a plurality of staple cartridges positioned within the shaft, wherein each staple cartridge comprises a cartridge body comprising a plurality of apertures and a plurality of staples each comprising a staple leg positioned in an aperture, wherein the staple legs are slidable within the apertures. The instrument assembly can further comprise a first jaw comprising a channel configured to receive a staple cartridge, a second jaw comprising an anvil, wherein the staple legs are configured to contact the anvil, a cartridge driver configured to sequentially advance a staple cartridge into the channel from a staging position, and a biasing member configured to sequentially advance a staple cartridge into the staging position.

BRIEF DESCRIPTION OF THE DRAWINGS

The features and advantages of this invention, and the manner of attaining them, will become more apparent and the invention itself will be better understood by reference to the following description of embodiments of the invention taken in conjunction with the accompanying drawings, wherein:

FIG. 1A is a cross-sectional view of the end effector of FIG. 1 taken along line 1A-1A in FIG. 1;

FIG. 2A is a cross-sectional view of the end effector and shaft of FIG. 1 taken along line 2A-2A in FIG. 2;

FIG. 5 is a cross-sectional elevation view of the end effector and shaft of FIG. 1 illustrating a firing member in a dropped position;

FIG. 5A is a detail view of the firing member of FIG. 5 positioned in its dropped position;

FIG. 5B is a detail view of the firing member of FIG. 5 illustrating a cutting member, or distal knife portion, thereof;

FIG. 11 is a cut-away perspective view of the staple cartridge channel of FIG. 4A;

FIG. 12 is a cut-away elevational view of the staple cartridge channel of FIG. 4A;

FIG. 16 is a perspective view of the end effector of FIG. 1 without a staple cartridge positioned therein;

FIG. 16A is a cross-sectional elevational view of the end effector of FIG. 1 as illustrated in FIG. 16;

FIG. 17 is a perspective view of the end effector of FIG. 1 illustrating a staple cartridge positioned therein and the cutting member of FIG. 5B in a dropped condition;

FIG. 17A is a cross-sectional elevational view of the end effector of FIG. 1 as illustrated in FIG. 17;

FIG. 18 is a perspective view of the end effector of FIG. 1 illustrating the cutting member of FIG. 5B in a raised condition and the anvil of the end effector in an open condition;

FIG. 18A is cross-sectional elevational view of the end effector of FIG. 1 as illustrated in FIG. 18;

FIG. 19 is a cross-sectional elevational view of the end effector of FIG. 1 illustrating the cutting member in a partially advanced condition and the anvil in a closed condition;

FIG. 20 is a cross-sectional elevational view of the end effector of FIG. 1 illustrating the cutting member in a partially advanced condition and a plurality of staple drivers and staples in a fired condition;

FIG. 21 is a cross-sectional elevational view of the end effector of FIG. 1 illustrating the cutting member in a fully advanced condition;

FIG. 22 is a cross-sectional elevational view of the end effector of FIG. 1 illustrating the cutting member in a partially retracted condition and a plurality of staple drivers returned to an unfired condition;

FIG. 23 is a cross-sectional elevational view of the end effector of FIG. 1 illustrating the cutting member in a fully retracted and depressed condition and the anvil in an open condition wherein a staple cartridge positioned within the shaft can be advanced into the end effector after the previous staple cartridge has been removed therefrom.

Corresponding reference characters indicate corresponding parts throughout the several views. The exemplifications set out herein illustrate certain embodiments of the invention, in one form, and such exemplifications are not to be construed as limiting the scope of the invention in any manner.

DETAILED DESCRIPTION

Figure 1:
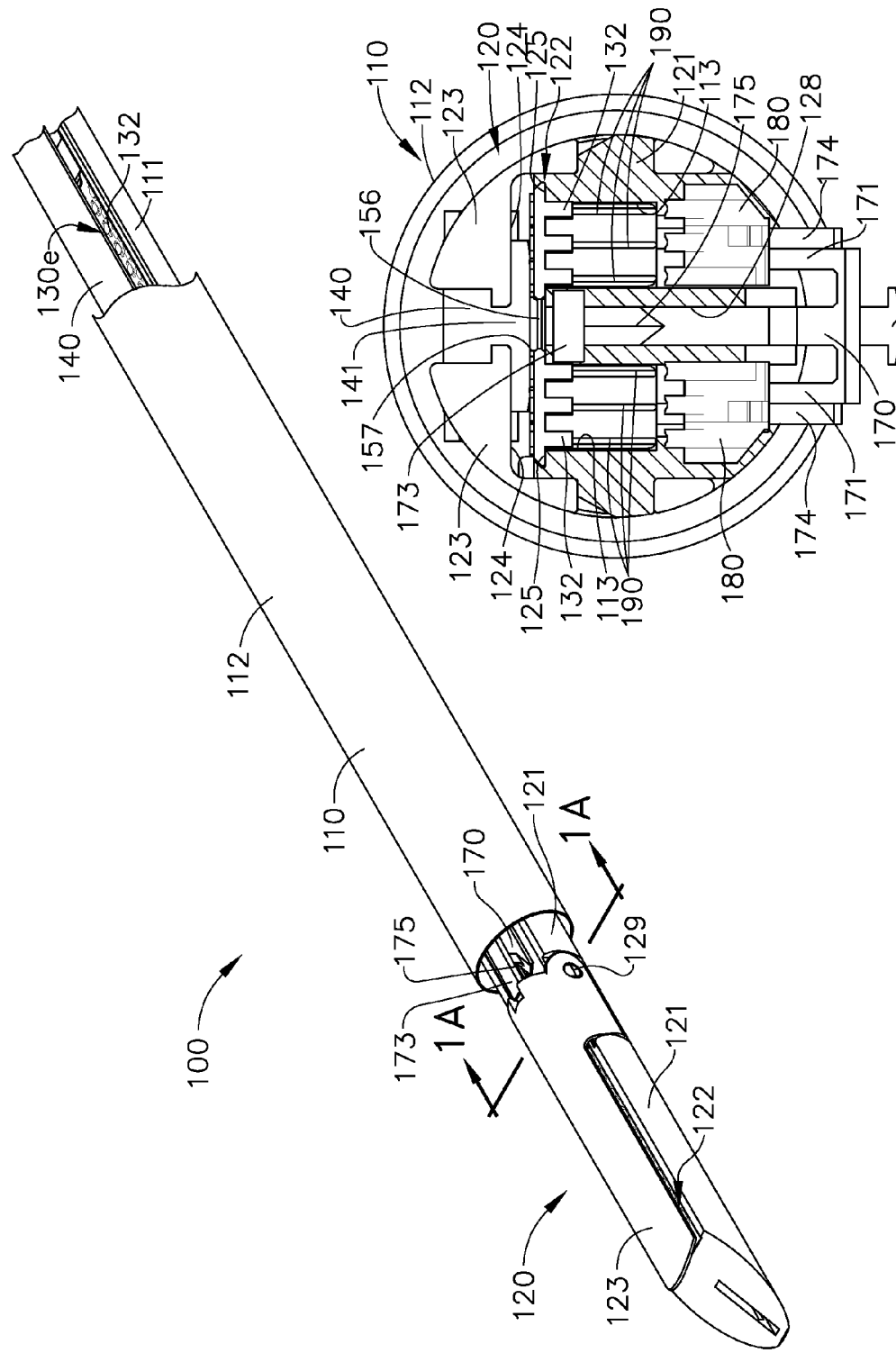
FIG. 1 is a perspective view of an end effector and a shaft of a surgical stapling instrument.

The Applicant of the present application also owns the U.S. patent applications identified below which were filed on even date herewith and which are each herein incorporated by reference in their respective entirety:

U.S. patent application Ser. No. 13/225,866, entitled FIRING MEMBER DISPLACEMENT SYSTEM FOR A STAPLING INSTRUMENT, now U.S. Patent Publication No. 2013/0056522, Inventor: Brett Swensgard;

U.S. patent application Ser. No. 13/225,857, entitled STAPLING INSTRUMENT COMPRISING RESETTABLE STAPLE DRIVERS; now U.S. Patent Publication No. 2013/0056521, Inventor: Brett Swensgard; and U.S. patent application Ser. No. 13/225,842, entitled CONTINUOUS STAPLING INSTRUMENT, now U.S. Patent Publication No. 2013/0056520, Inventor: Brett Swensgard.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

In various embodiments, a surgical stapling instrument can comprise a plurality of staple cartridges stored therein. In at least one embodiment, the stapling instrument can comprise an end effector configured to receive the staple cartridges in a sequential order. For example, the end effector can comprise a jaw configured to receive a first staple cartridge therein wherein, after the first staple cartridge has been deployed, a second, or subsequent, staple cartridge can be fed into the jaw so that the surgical stapling instrument can be used once again. In at least one such embodiment, the end effector can be attached to a shaft of the surgical stapling instrument and the staple cartridges can be stored in the shaft. In order to sequentially insert the staple cartridges into the end effector, in various embodiments, the stapling instrument can further comprise a reciprocating driver which can advance the staple cartridges into position.

In various embodiments, referring now to FIG. 1, a stapling instrument, such as stapling instrument 100, for example, can comprise a shaft 110 and an end effector 120. Referring primarily to FIG. 1A, the shaft 110 can comprise a frame 111 and an outer housing 112. In at least one embodiment, the outer housing 112 can entirely, or at least partially, surround the frame 111. In certain embodiments, referring now to FIG. 2, the shaft 110 can comprise a plurality of staple cartridges 130 positioned therein. In at least one embodiment, the outer housing 112 can comprise a detachable portion which can be disassembled from the shaft 110 such that the staple cartridges 130 can be loaded into the shaft 110. In certain embodiments, the shaft 110 can comprise an access port through which the staple cartridges 130 can be loaded therein. In various embodiments, the staple cartridges 130 can be individually loaded into the shaft 110. In certain embodiments, the staple cartridges 130 can be pre-loaded into a magazine which is insertable into and removable from the shaft 110.

In various embodiments, referring again to FIGS. 1 and 2, the surgical instrument 100 can be supplied to a surgeon with a staple cartridge, such as first staple cartridge 130a, for example, already loaded into the end effector 120. In certain other embodiments, the surgical instrument 100 can be supplied to a surgeon without a staple cartridge positioned within the end effector 120. In order to position a staple cartridge within the end effector 120, in various embodiments, the surgical instrument 100 can comprise a cartridge driver, or feeding bar, 140 which can be configured to advance a staple cartridge into the end effector 120. Referring now to FIGS. 16 and 16A, the end effector 120 can comprise a first jaw 121 including a cartridge channel 122 wherein, in at least one such embodiment, the cartridge driver 140 can be configured to advance the first staple cartridge 130a, for example, into the cartridge channel 122. As illustrated in FIGS. 16 and 16A, the staple cartridge 130a can be positioned proximally with respect to the end effector 120 prior to being advanced into the end effector 120. In such a position, a distal end 141 of the cartridge driver 140 can be positioned within a proximal recess 131 defined in the proximal end of the staple cartridge 130a. In order to advance the staple cartridge 130a into the cartridge channel 122, referring now to FIGS. 17 and 17A, the cartridge driver 140 can be moved distally to engage a sidewall defining the proximal recess 131 and then move the staple cartridge 130a distally into the cartridge channel 122.

In various embodiments, referring again to FIGS. 16 and 16A, the cartridge channel 122 can comprise one or more support ledges 125, for example, located on opposite sides of the cartridge channel 122 which can be configured to support a staple cartridge, such as staple cartridge 130a, for example, as illustrated in FIGS. 17 and 17A. Similarly, referring to FIGS. 2 and 2A, the shaft 110 can comprise one or more support ledges 115, for example, located on opposite sides of the shaft frame 111 which can be configured to support one or more staple cartridges, such as the first staple cartridge 130a, a second staple cartridge 130b, a third staple cartridge 130c, a fourth staple cartridge 130d, and/or a fifth staple cartridge 130e, for example. In various embodiments, referring now to FIGS. 13 and 14, each staple cartridge 130a-130e, for example, can comprise a cartridge body 132 and a plurality of staples 190 at least partially positioned within the cartridge body 132. Hereinafter, any general reference to a staple cartridge 130 can apply to any one or more of the staple cartridges 130a-130e, for example. In various embodiments, the cartridge body 132 can comprise a first lateral support rail 133 extending along a first side of the cartridge body 132 and a second lateral support rail 133 extending along a second side of the cartridge body 132. In certain embodiments, the lateral support rails 133 of the cartridge body 132 can be supported by the support ledges 115 and/or the support ledges 125 wherein, when a staple cartridge 130 is moved from the shaft 110 to the end effector 120, the staple cartridge 130 can be slid between a position in which it is supported by the support ledges 115 in the shaft 110 to a position in which it is supported by the support ledges 125 in the end effector 120.

Figure 24:
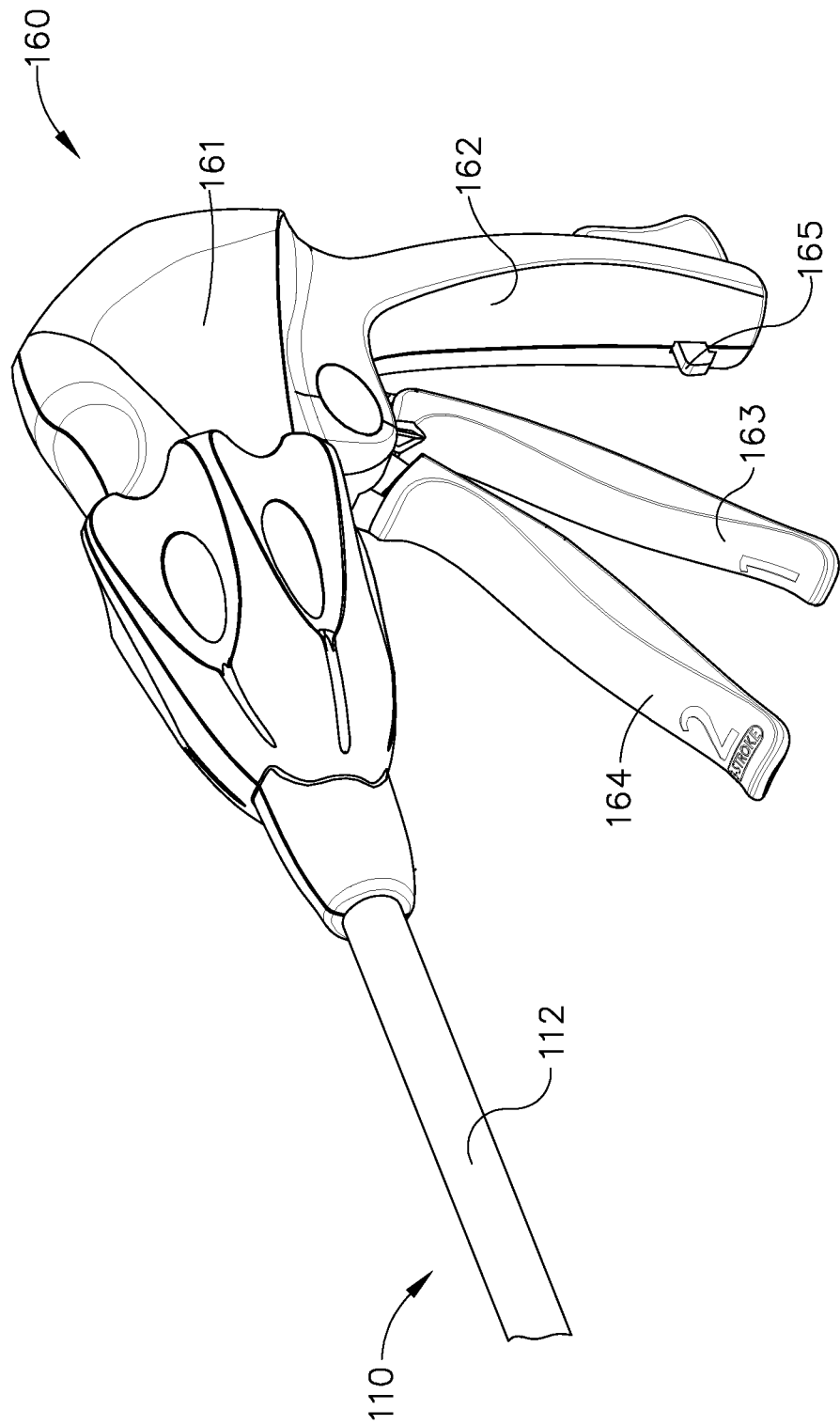
FIG. 24 is a perspective view of a handle of a surgical stapling instrument in accordance with at least one embodiment.

In various embodiments, referring now to FIG. 24, the surgical instrument 100 can further comprise a handle, such as handle 160, for example, wherein the handle 160 can comprise a housing 161 and a pistol grip 162. In certain embodiments, the handle 160 can further comprise a first trigger 163 and a second trigger 164, wherein the first trigger 163 and the second trigger 164 can be pivotably coupled to the housing 161. In certain embodiments, the cartridge driver 140 can be operably coupled to the first trigger 163 such that, when the first trigger 163 is moved toward the pistol grip 162 between an unactuated position (FIG. 24) and an actuated position, the cartridge driver 140 can be moved distally toward the end effector 120. In at least one embodiment, a complete stroke of the first trigger 163 can cause the cartridge driver 140 to completely advance a staple cartridge 130 into the end effector 120, as described above. In at least one such embodiment, the proximal end of the cartridge driver 140 can comprise a rack, for example, wherein the first trigger 163 can comprise a driver configured to engage the rack and displace the cartridge driver 140 distally. In various other embodiments, any suitable drive arrangement can be utilized to operably couple the first trigger 163 and the cartridge driver 140. In various embodiments, the handle 160 can further comprise a lock 165 which can be configured to hold the first trigger 163 in an actuated position. In various other embodiments, the handle 160 can further comprise a first trigger spring which can be configured to bias the first trigger 163 back to its unactuated position (FIG. 24) after the first trigger 163 has been actuated. In certain other embodiments, a return spring can be connected to the cartridge driver 140 and the handle housing 161 wherein, when the first trigger 163 and the cartridge driver 140 have reached the end of their stroke, the drive member can be disengaged from, or be rotated out of engagement with, the cartridge driver 140. In such circumstances, the return spring can bias the cartridge driver 140 proximally back to its unactuated position. In any event, the cartridge driver 140 can be advanced from a proximal, unactuated position to a distal, actuated position in order to advance a staple cartridge 130 into the end effector 120 and then return back to its proximal position once again.

Figure 2:
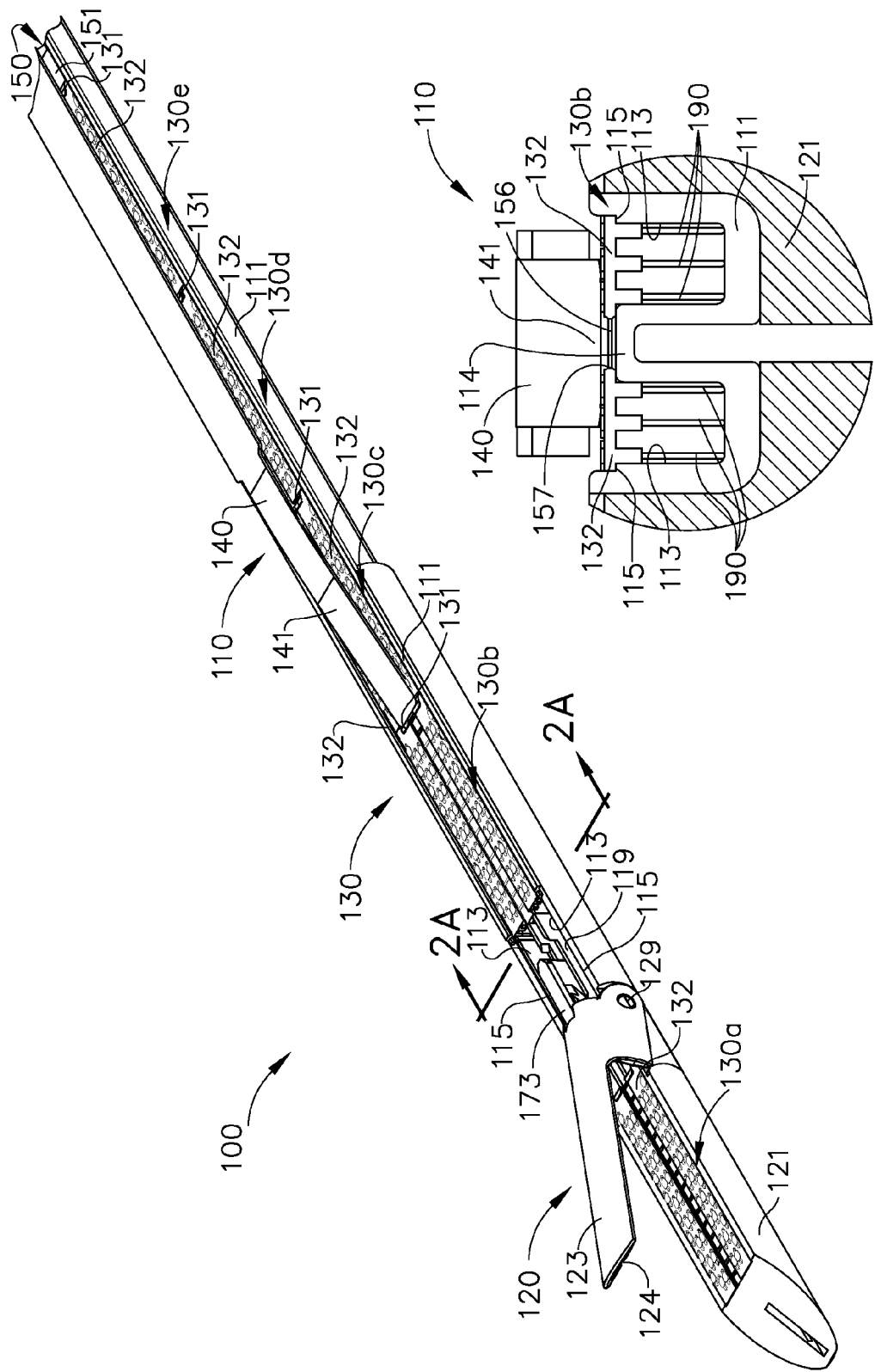
FIG. 2 is a perspective view of the end effector and shaft of FIG. 1 illustrating a staple cartridge positioned within the end effector and a plurality of staple cartridges positioned within the shaft illustrated with some components removed.
Figure 3:
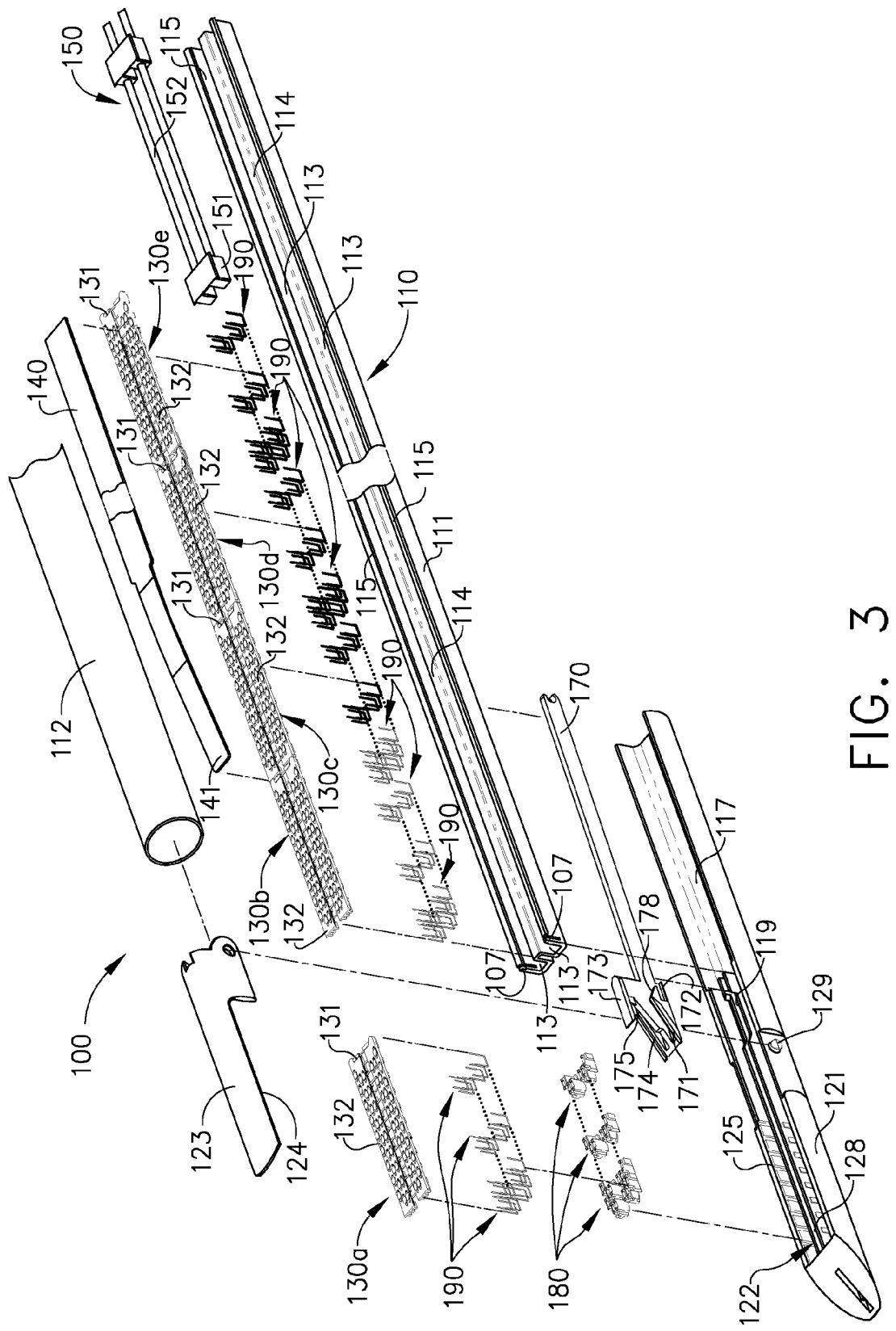
FIG. 3 is an exploded view of the end effector and shaft of FIG. 1.

Once the first staple cartridge 130a has been positioned in the end effector 120, as illustrated in FIG. 2, the end effector 120 can be positioned within a surgical site. In various embodiments, the end effector 120 can further comprise a second jaw 123 which can be pivotably coupled to the first jaw about a pivot 129. In at least one embodiment, the second jaw 123 can be pivoted between an open position (FIG. 2) and a closed position (FIG. 1) by an actuator. In at least one such embodiment, primarily referring now to FIGS. 3, 18, 18A, and 19, the surgical instrument 100 can further comprise a firing member 170 which can be advanced distally in order to engage the second jaw 123 and pivot the second jaw 123 downwardly toward the first jaw 121. In various embodiments, the firing member 170 can comprise a first flange 172 and a second flange 173 wherein the first flange 172 can be configured to engage the first jaw 121 and the second flange 173 can be configured to engage the second jaw 122. More particularly, referring primarily to FIG. 19, the first flange 172 can be configured to slide alongside the outside surface of the first jaw 121 and the second flange 173 can be configured to enter into a slot 103 defined in the second jaw 123 and engage a sidewall of the slot 103 in order to cam the second jaw 123 from an open position (FIG. 18) to a closed position (FIG. 19). In various embodiments, referring again to FIG. 24, the second trigger 164 of the handle 160 can be operably coupled to the firing member 170 such that, when the second trigger 164 is moved toward the pistol grip 162, the firing member 170 can be driven distally, as described above. In at least one embodiment, the proximal end of the firing member 170 can comprise a rack including a plurality of teeth and the second trigger 164 can comprise a gear portion which can be configured to engage the rack teeth and drive the rack and the firing member 170 distally as the second trigger 164 is moved between an unactuated position (FIG. 24) and an actuated position. In at least one such embodiment, a complete actuation of the second trigger 164 can result in a complete actuation of the firing member 170, which is described in greater detail further below.

As outlined above, the drive member 140 and the firing member 170 can be actuated sequentially and independently of one another by two separate triggers. In certain other embodiments, though, a surgical instrument can comprise a single trigger which, when actuated, can sequentially actuate the drive member 140 and the firing member 170. In either event, the reader will appreciate that the drive member 140 and the firing member 170 can be moved relative to each other during the operation of the surgical instrument 100. For example, when the drive member 140 is advanced distally to position a staple cartridge 130 in the end effector 120, the drive member 140 can move relative to the firing member 170. In certain embodiments, however, referring now to FIG. 18A, the firing member 170 can comprise a distal knife portion 175 which can be positioned intermediate the cartridge channel 122 of the end effector 120 and the frame 111 of the shaft 110 when the firing member 170 is in its unactuated position. Stated another way, the distal knife portion 175 can block the advancement of a staple cartridge 130 as the staple cartridge 130 is advanced between the cartridge channel 122 and the frame 111 unless, as described in greater detail below, the distal knife portion 175 is moved out of the way when the staple cartridge 130 is advanced into the cartridge channel 122.

In order to move the distal knife portion 175 out of the way, further to the above, the distal knife portion 175 can be moved from its unactuated position (FIG. 18) to a dropped position which is illustrated in FIGS. 5A and 16A. In various embodiments, the firing member 170 can be retracted proximally such that the distal knife portion 175 can contact the frame 111 of the shaft 110 and/or a portion of the first jaw 121 and be displaced downwardly, for example, into a position in which the cartridge body 132 of a staple cartridge 130 can slide over the top of the distal knife portion 175, as described in greater detail below. In at least one such embodiment, referring now to FIG. 4A, the first jaw 121 can comprise at least one declined ramp, or cam, 118 wherein the knife portion 175 can be configured to contact the declined ramp 118 and slide down the declined surface thereof. In certain embodiments, the knife portion 175 can further comprise at least one corresponding declined surface, or follower, 178 which can be configured to engage the at least one declined ramp 118. In at least one such embodiment, the declined ramp 118 and the declined surface 178 can be oriented at the same, or at least substantially the same, angle. In certain embodiments, as a result, the knife portion 175, for example, of the firing member can descend in a direction which is transverse to its firing path, i.e., the path in which firing member 170 is advanced to fire, or deploy, the staples of the staple cartridge 130, as described in greater detail further below. In at least one such embodiment, such a firing path can comprise a longitudinal axis extending between its proximal, unactuated position and its distal, actuated position, for example.

Figure 4:
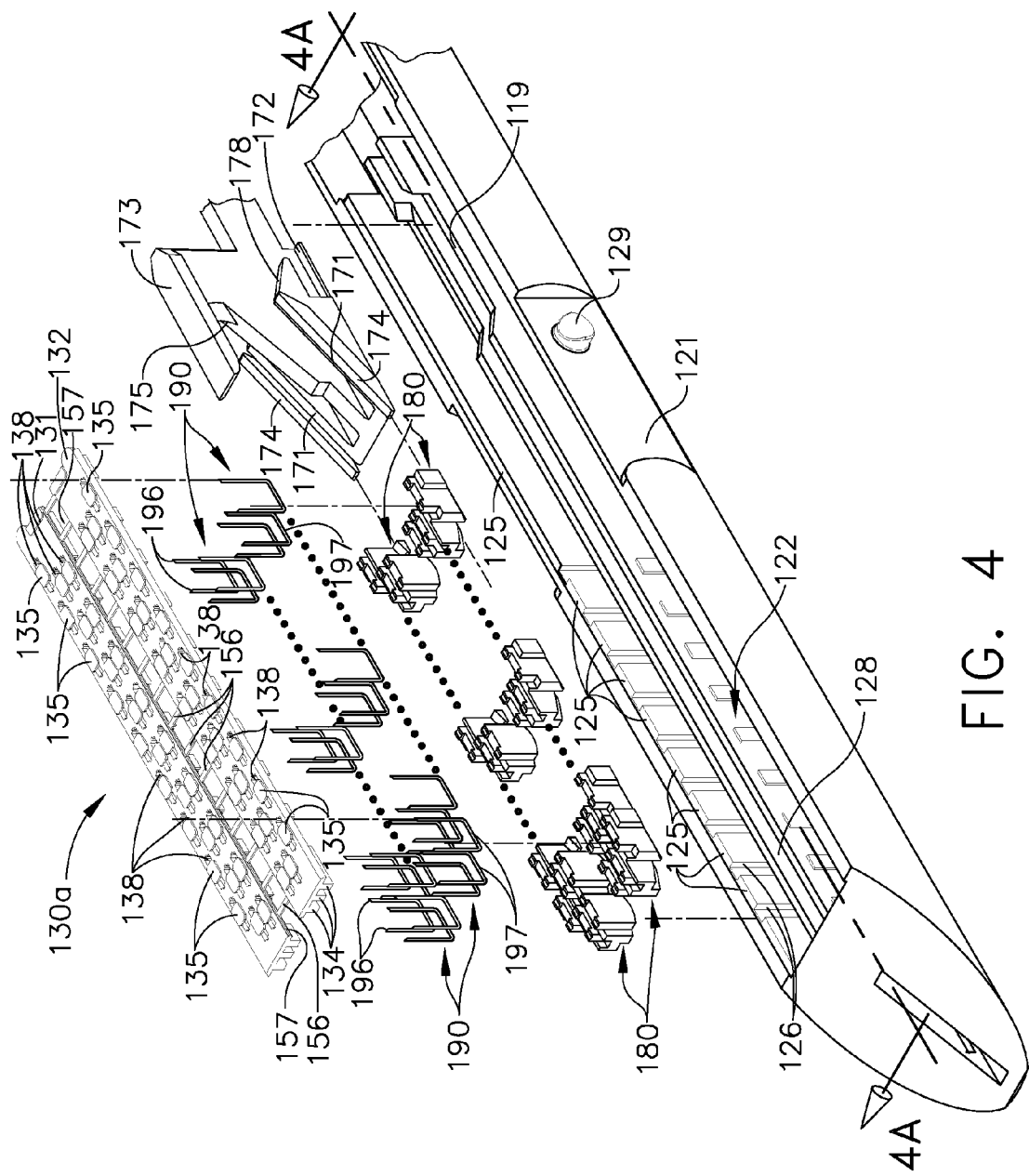
FIG. 4 is an exploded view of a jaw of the end effector of FIG. 1 configured to receive a staple cartridge including a plurality of staple drivers configured to eject the staple cartridge from the jaw.
Figure 4A:
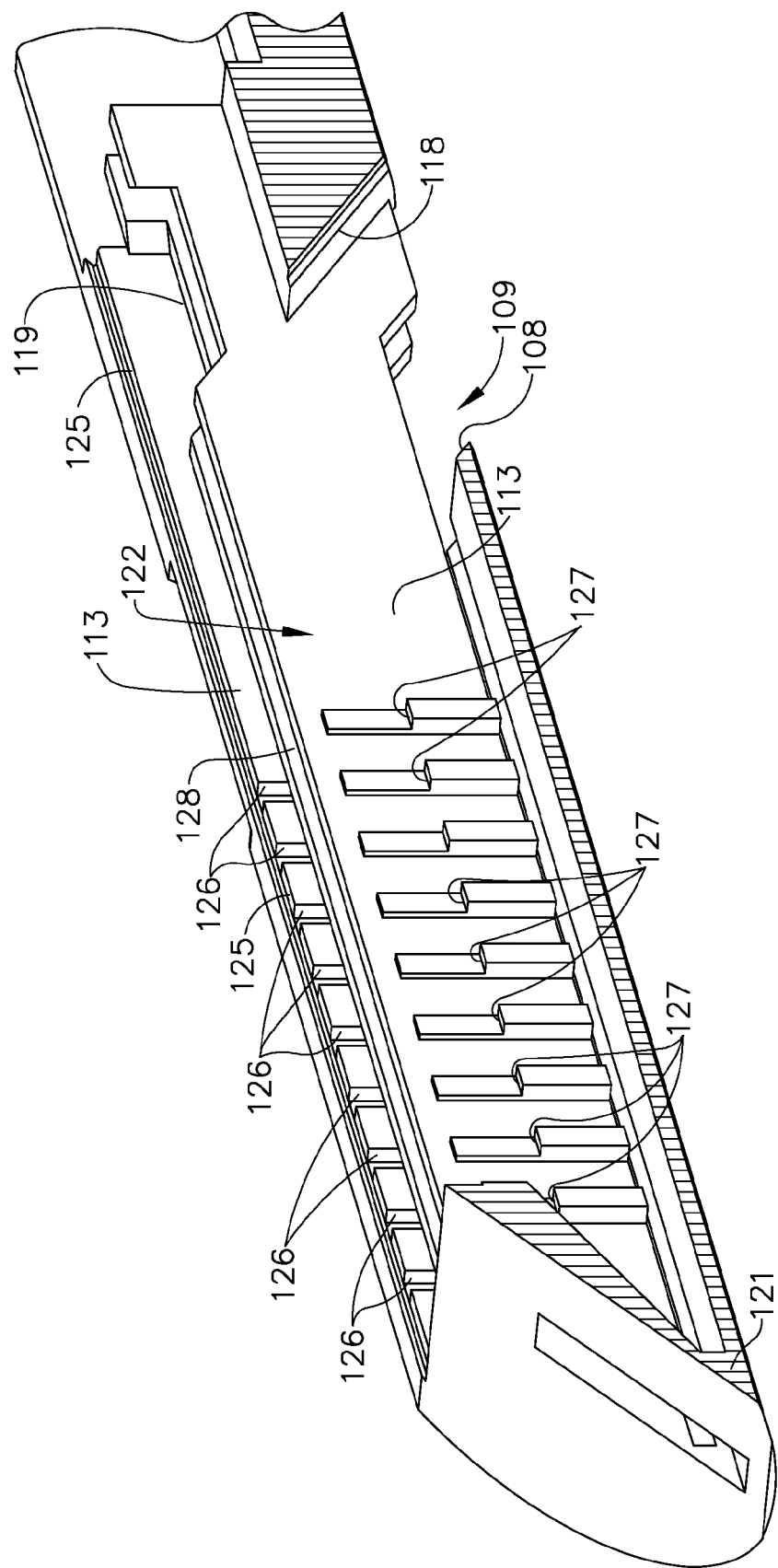
FIG. 4A is a cross-sectional view of a staple cartridge channel of the jaw of FIG. 4.

In various embodiments, referring to FIGS. 4A and 5A, the first jaw 121 can comprise one or more windows, openings, slots, channels, and/or recesses which can be configured to permit the distal knife portion 175 to move from its unactuated position to its dropped position. In at least one embodiment, the first jaw 121 can comprise a recess 119 which can be configured to receive the second flange 173 of the firing member 170 and a window, or opening, 109 which can be configured to permit the first flange 172 of the firing member 170 to at least partially drop downwardly out of the first jaw 121 when the knife portion 175 is moved into its dropped position. At such point, referring again to FIG. 16A, the distal knife portion 175 may no longer obstruct the path of the staple cartridges and, as a result, a staple cartridge 130 can be slid distally past the distal knife portion 175, as illustrated in FIGS. 17 and 17A, as described above. In at least one such embodiment, the top surface of the second flange 173 can be completely recessed within the recess 119, or positioned substantially flush with the top of the recess 119, such that the cartridge body 132 of a staple cartridge 130 can slide thereover. In various embodiments, the top surface of the second flange 173 can be aligned with and/or positioned below the cartridge support surfaces 115 and/or the cartridge support surfaces 125 such that the cartridge body 132 of the staple cartridge 130 can slide thereover without interference, or with little interference, therebetween. Further to the above, referring generally to FIG. 2A, each staple cartridge 130 can comprise a plurality of staple rows which can slide within a first lateral channel 113 alongside a first side of the distal knife portion 175 and a plurality of staple rows which can slide within a second lateral channel 113 alongside a second, or opposite, side of the distal knife portion 175 as the staple cartridge 130 is advanced past the distal knife portion 175 into the cartridge channel 122.

In various embodiments, further to the above, the firing member 170 can also be selectively engaged with the first trigger 163 such that, when the first trigger 163 is pulled toward the pistol grip 162 to advance a staple cartridge 130 into the end effector 120, as described above, the first trigger 163 can pull the firing member 170 proximally into contact with the declined ramp 118 in order to move the distal knife portion 175 into its descended position. In various embodiments, the first trigger 163 can comprise another drive member which can be configured to engage the rack portion of the firing member 170 and pull the firing member 170 proximally when the first trigger 163 is actuated. Also similar to the above, such a drive member can become disengaged from the firing member 170 when the first trigger 163 has reached the end of its actuation such that the firing member 170 can be subsequently and independently actuated by the second trigger 164. Nonetheless, once the staple cartridge 130 has been slid past the lowered knife portion 175 and the staple cartridge 130 has been sufficiently positioned within the end effector 120, the cartridge driver 140 can be retracted to its unactuated position, as described above, and the firing member 170 can be returned upwardly to its unactuated position. In such circumstances, the firing member 170 can be displaced distally such that the declined surface 178 slides upwardly along the declined ramp 118. In at least one such embodiment, the firing member 170 can be resiliently deflected downwardly when the distal knife portion 175 is moved into its dropped position such that the firing member 170 can resiliently return to its unactuated position. In certain embodiments, the surgical instrument 100 can further comprise a spring which can be configured to bias the firing member 170 into its unactuated position. In any event, once a staple cartridge 130 has been positioned within the end effector 120, and the cartridge driver 140 and the firing member 170 have been returned to their unactuated positions, the firing sequence to deploy the staple cartridge 130 can begin, as described in greater detail further below.

Turning now to FIG. 19 once again, the firing member 170 can be advanced distally from its unactuated position to engage the second jaw 123 and move the second jaw 123 into a closed position, as described above. In various circumstances, such movement of the firing member 170 can be generated by a partial actuation of the second trigger 164 wherein, if the surgeon desires, the surgeon can release the partially-actuated second trigger 164 to return the firing member 170 back to its unactuated position and allow the second jaw 123 to be returned to its open position. In at least one such embodiment, the end effector 120 can comprise a spring which can be configured to bias the second jaw 123 into its open position as the firing member 170 is being retracted. Furthermore, the handle 160 can further comprise a trigger spring operably engaged with the second trigger 164 which can be configured to return the second trigger 164 to its unactuated position when it is released by the surgeon. In any event, the surgeon can reopen the end effector 120 in order to reposition the jaws 121 and 123 relative to the targeted tissue and, once the surgeon is satisfied with the position of the jaws 121 and 123, the surgeon can actuate the second trigger 164 to close the second jaw 123 once again. As the second jaw 123 is moved into its closed position, the second jaw 123 can contact the tissue positioned intermediate the first jaw 121 and the second jaw 123 and position the tissue against a top, or tissue-contacting, surface 136 of the cartridge body 132. In at least one such embodiment, the tips of the staple may be recessed with respect to, and/or positioned flush with, the tissue-contacting surface 136 such that, when the tissue is compressed against the cartridge body 132, the staple tips do not penetrate, or at least substantially penetrate, the tissue positioned thereagainst. Once the second jaw 123 has been closed and the tissue has been compressed, the firing member 170 can be advanced distally, as described above.

Figure 6:
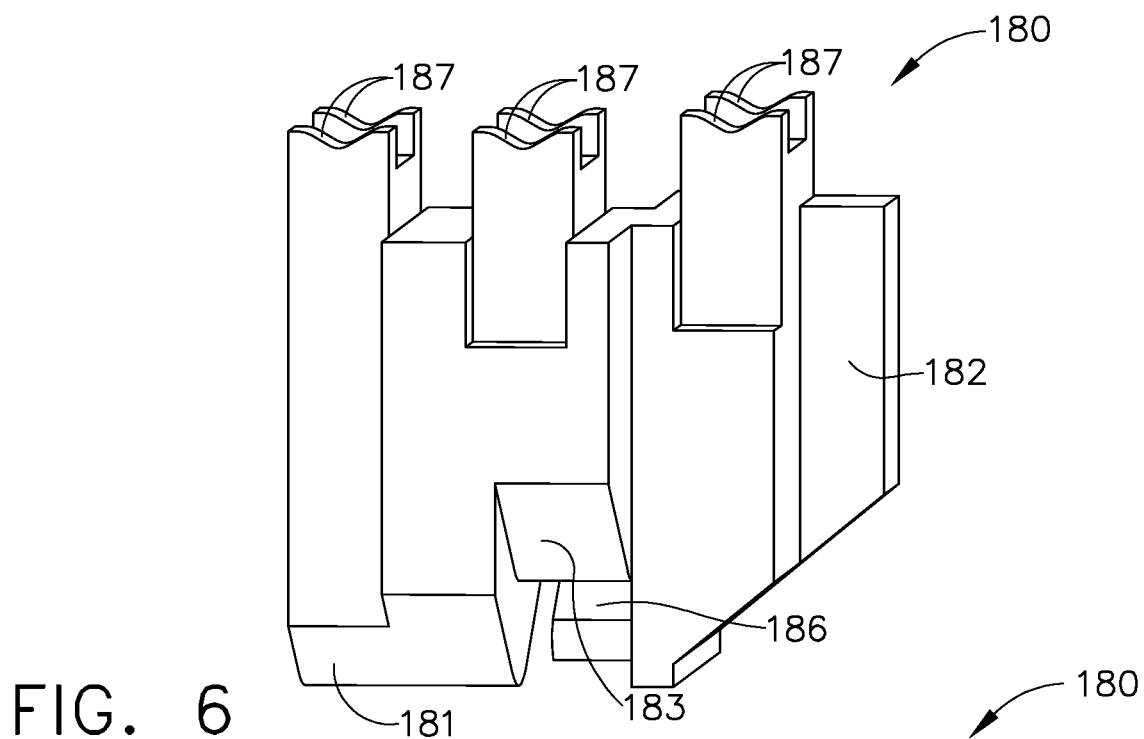
FIG. 6 is a perspective view of a staple driver of FIG. 4.
Figure 7:
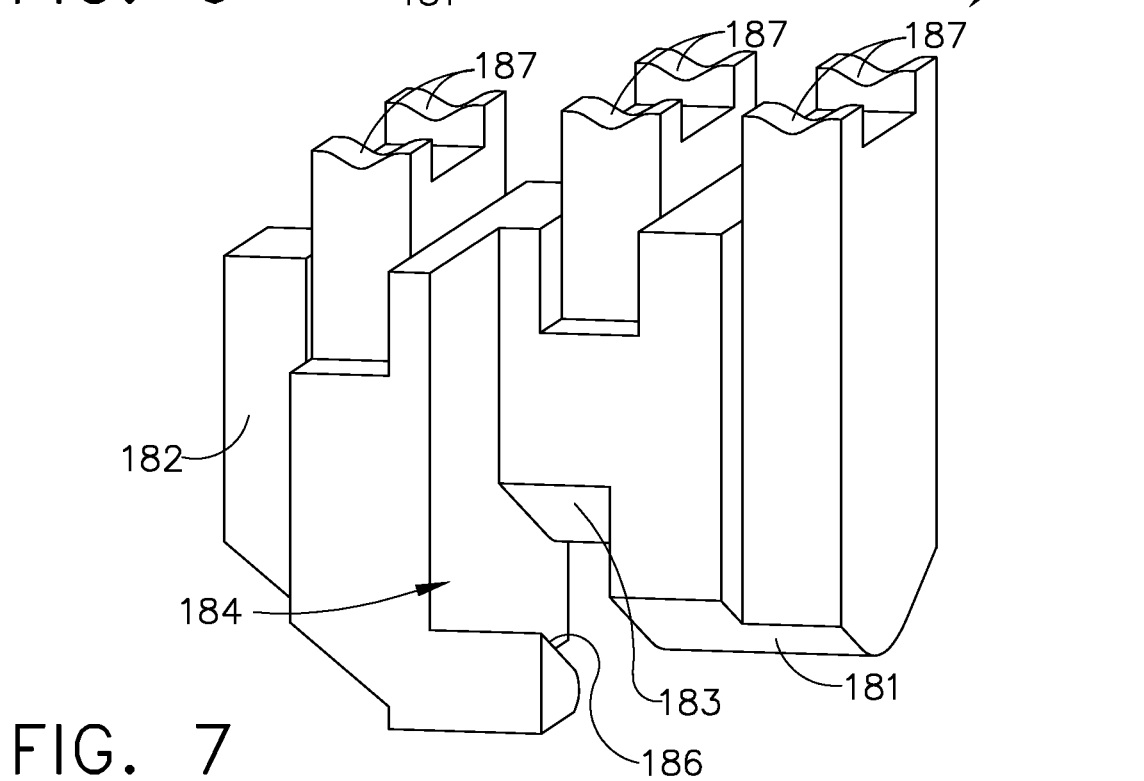
FIG. 7 is another perspective view of the staple driver of FIG. 6.
Figure 8C:
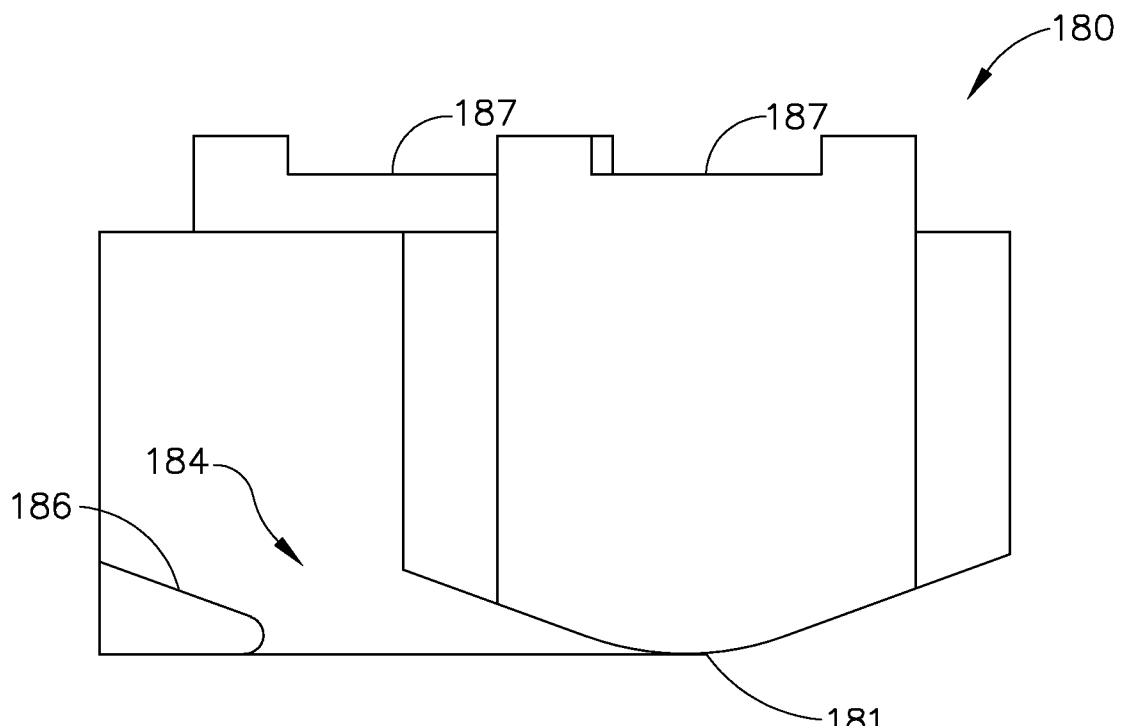
FIG. 8C is an elevation view of the staple driver of FIG. 6.
Figure 8:
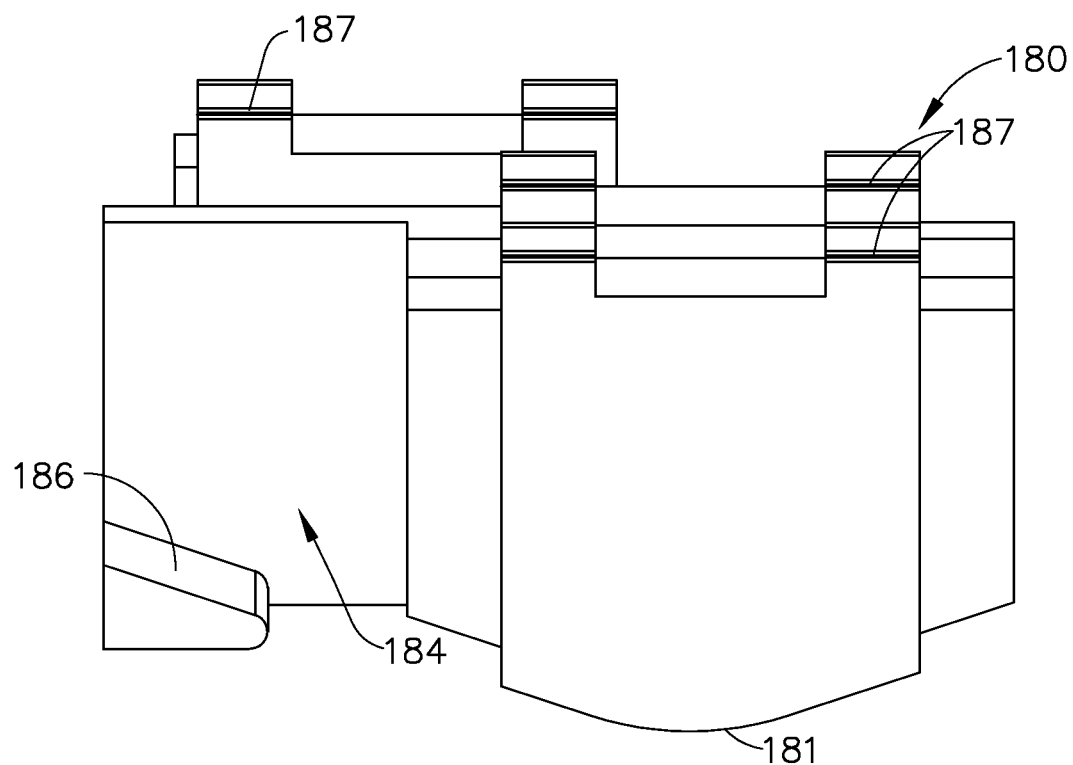
FIG. 8 is another perspective view of the staple driver of FIG. 6.
Figure 8B:
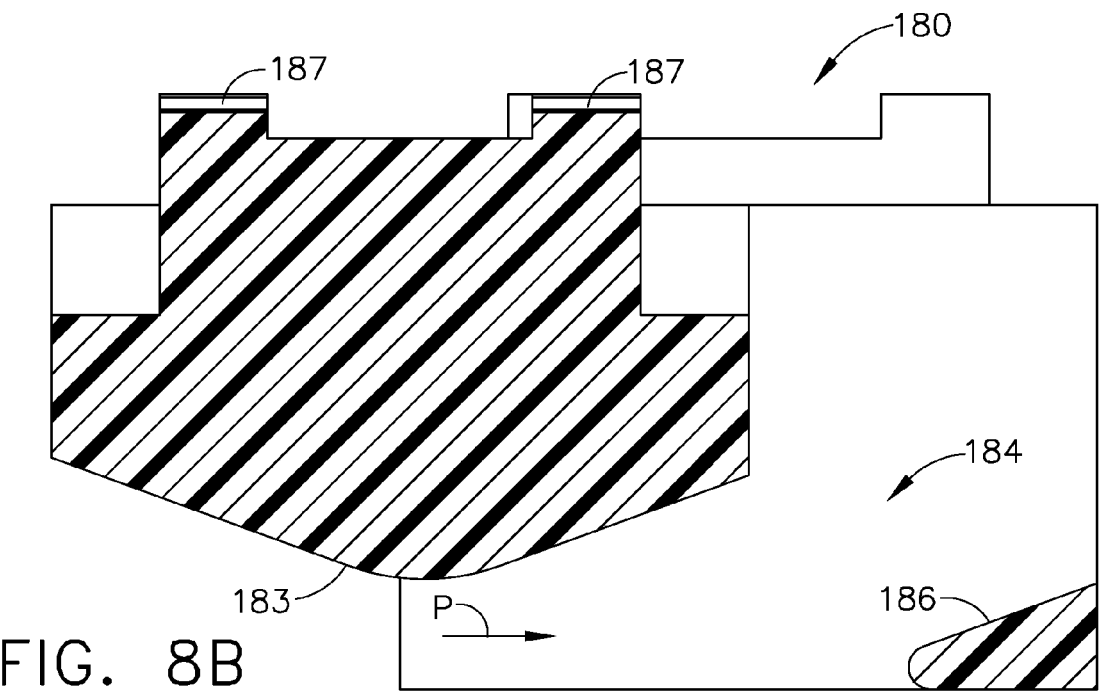
FIG. 8B is a cross-sectional perspective view of the staple driver of FIG. 6.
Figure 8A:
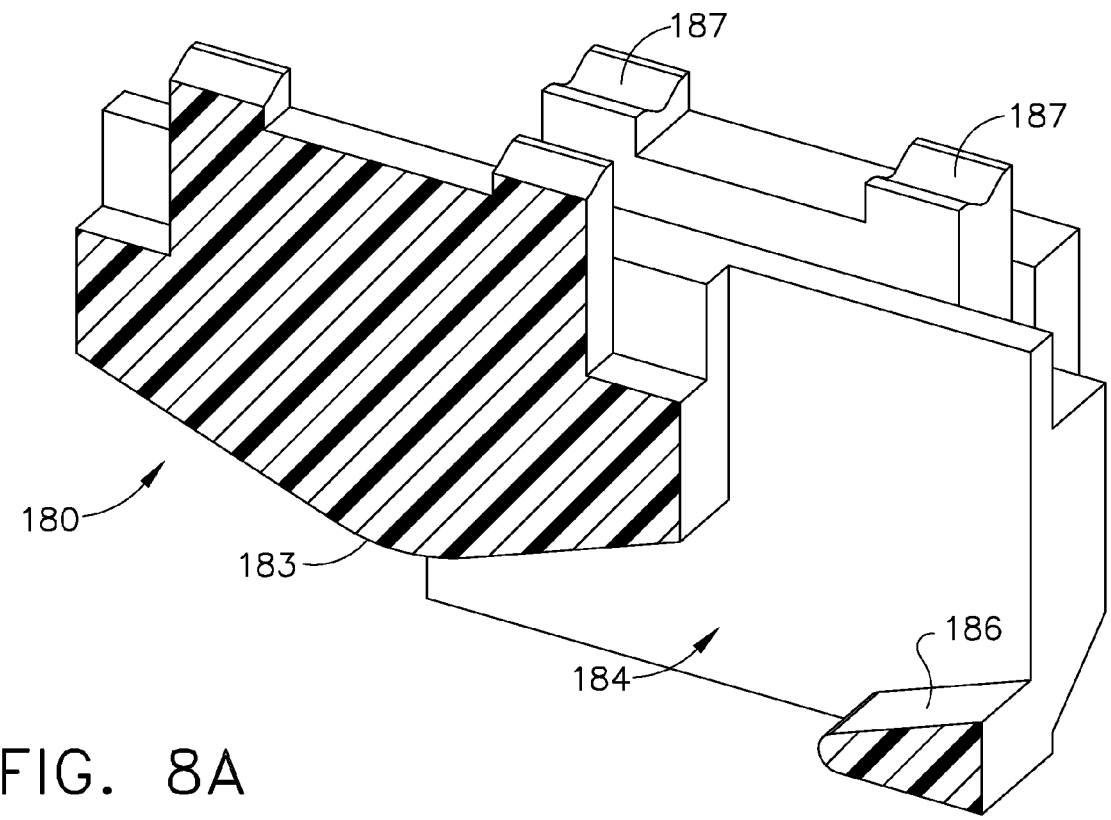
FIG. 8A is a cross-sectional elevation view of the staple driver of FIG. 6.
Figure 9:
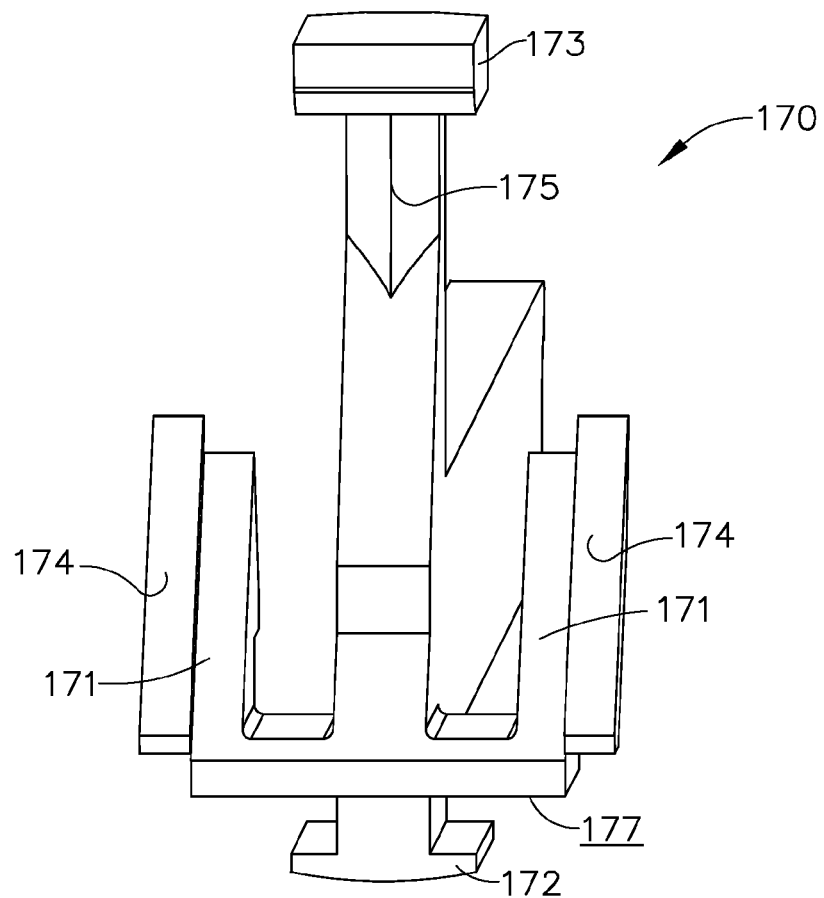
FIG. 9 is a perspective view of the cutting member of FIG. 5B.
Figure 10:
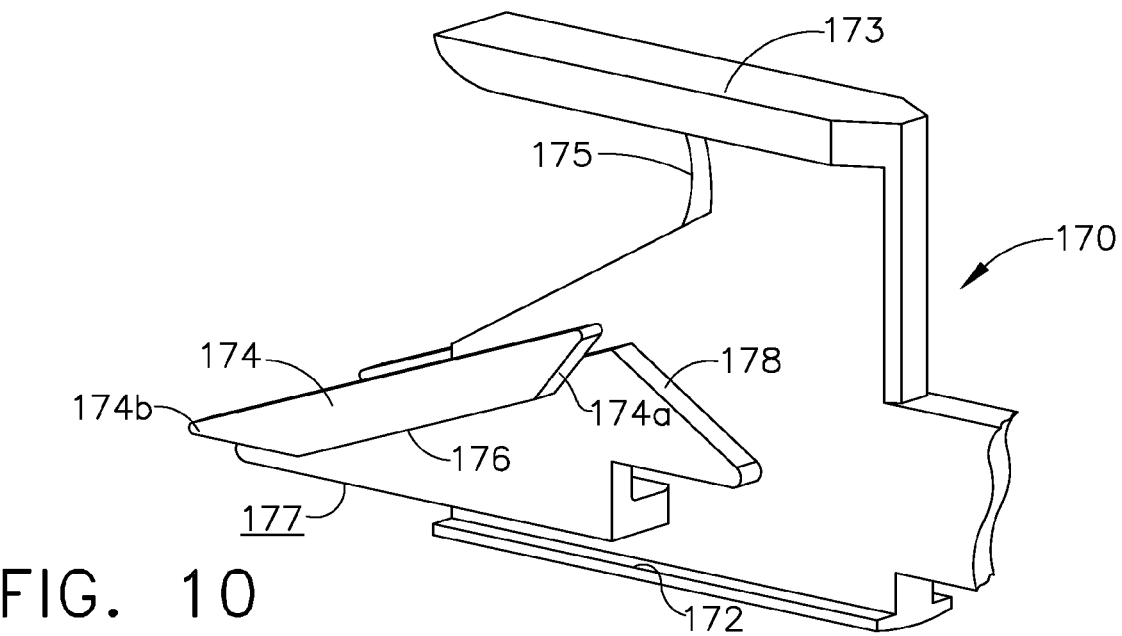
FIG. 10 is another perspective view of the cutting member of FIG. 5B.
Figure 13:
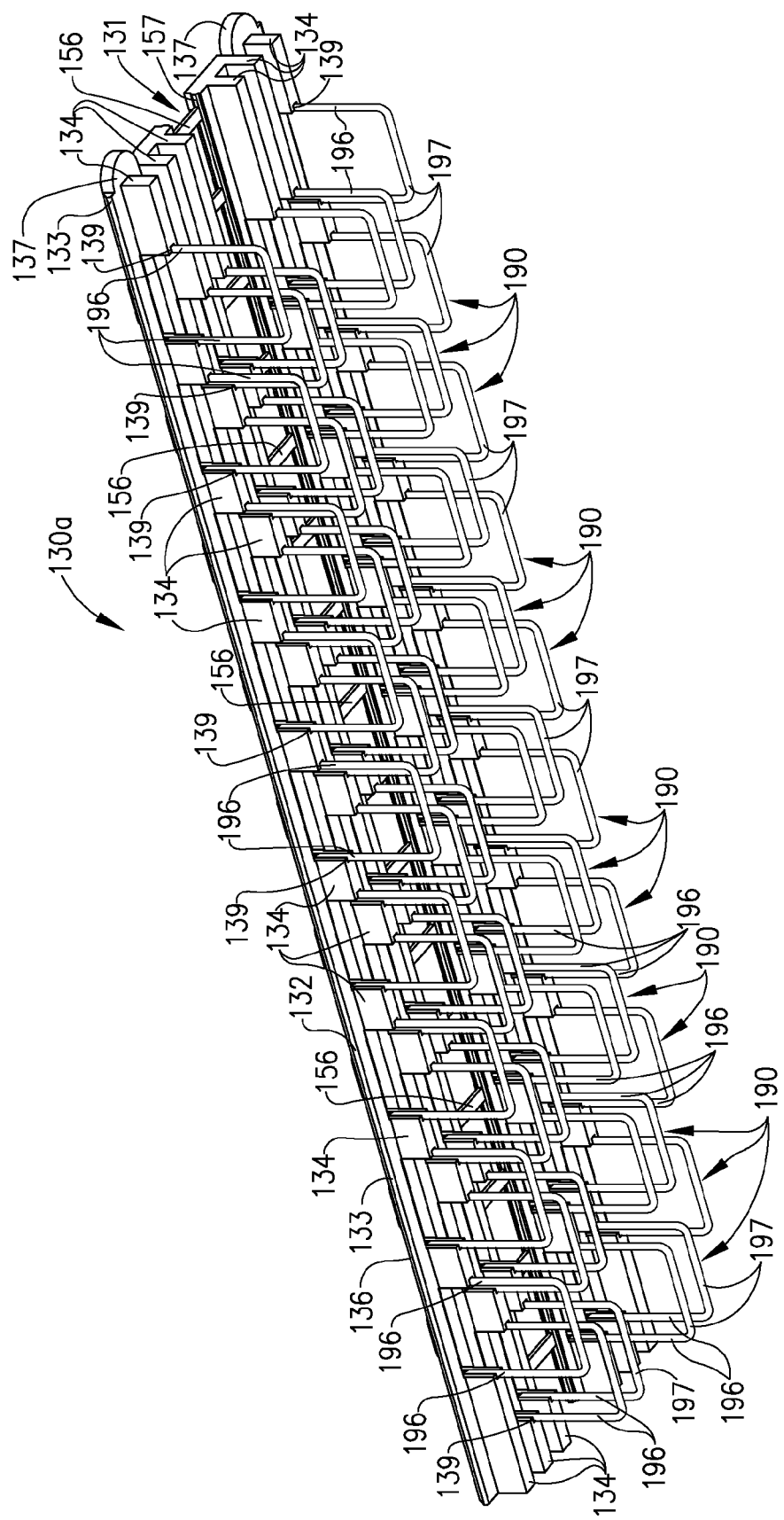
FIG. 13 is a bottom perspective view of a staple cartridge of FIG. 2 illustrated in an unfired condition.
Figure 14:
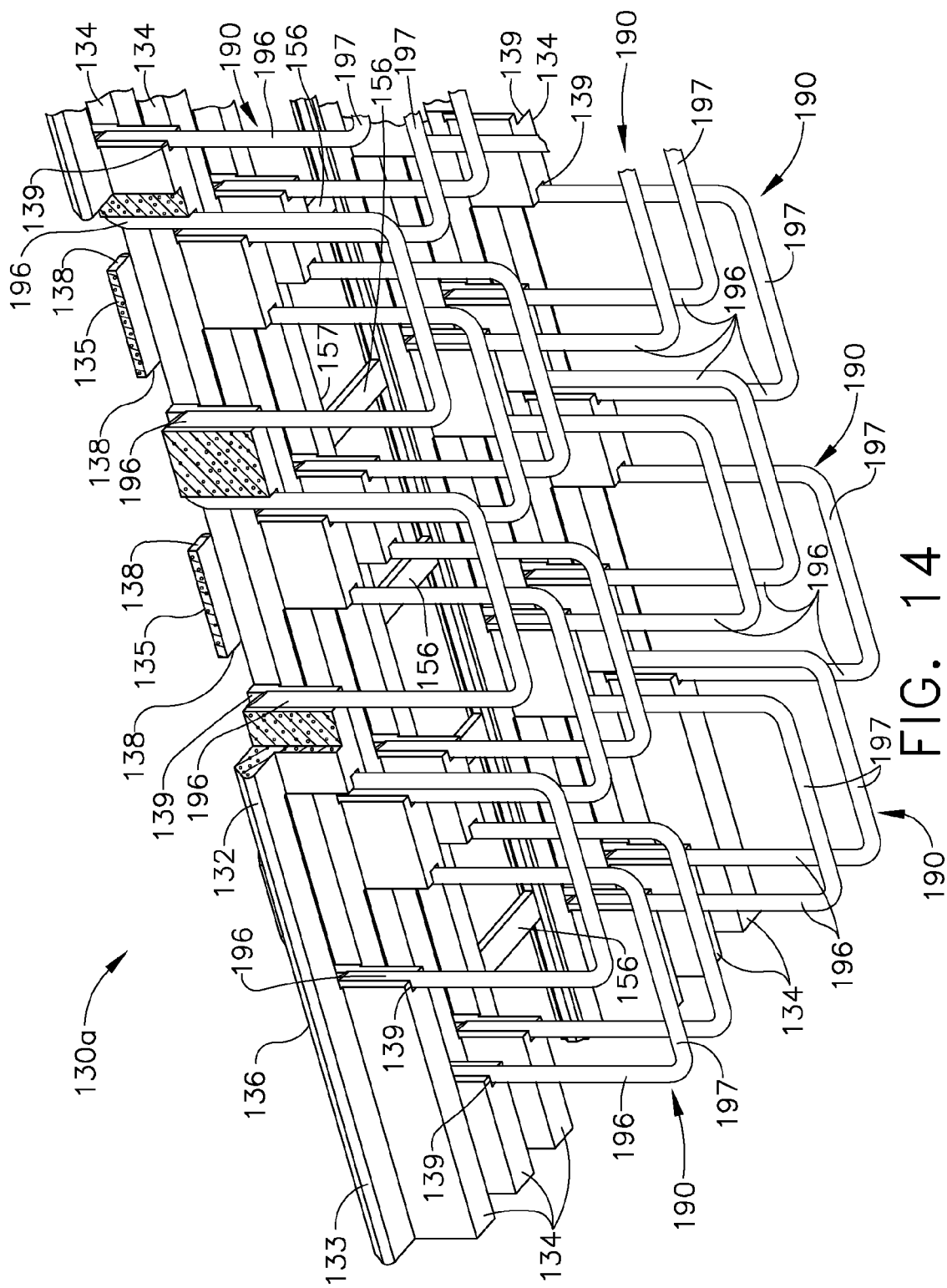
FIG. 14 is a partial cross-sectional view of the staple cartridge of FIG. 13.

Upon comparing FIG. 19 and FIG. 20, the reader will note that the firing member 170 has been partially advanced within the end effector 120. As illustrated in FIG. 20, the distal end of the firing member 170 can be configured to sequentially engage a plurality of staple drivers 180 positioned within the first jaw 121 in order to lift a plurality of staples 190 toward the second jaw 123. Referring now to FIGS. 9 and 10, the distal portion of the firing member 170 can further comprise one or more lift ramps 171 which can be configured to engage the staple drivers 180 and lift the staple drivers 180 upwardly as the lift ramps 171 pass thereunder. Referring now to FIGS. 6, 7, 8, 8A, 8B, and 8C, each staple driver 180 can comprise a corresponding inclined surface 181 which can be contacted by a lift ramp 171. In various embodiments, the lift ramps 171 of the firing member and the inclined surfaces 181 of the staple drivers 180 can be inclined at the same, or at least substantially the same, angle. Referring primarily to FIGS. 6 and 7, each staple driver 180 can comprise one or more staple cradles 187 which can each be configured to support a staple 190 thereon, as illustrated in FIG. 19. In at least one embodiment, referring now to FIGS. 13 and 14, each staple 190 can comprise a base 197, which can be positioned within a cradle 187, and one or more staple legs 196 extending upwardly from the base 197. As also illustrated in FIGS. 13 and 14, at least a portion of the staple legs 196 can be positioned within and/or extend through the cartridge body 132 wherein, as described in greater detail below, the staple drivers 180 can be configured to move the staples 190 relative to the cartridge body 132 as the firing member 170 is advanced.

Referring primarily to FIG. 120, the lift ramps 171 of the firing member 170 can contact the proximal-most staple drivers 180 and begin to lift them, and the staples 190 supported thereon, toward the second jaw 123. As the firing member 170 is progressed even further toward the distal end of the end effector 120, the lift ramps 171 can sequentially contact the staple drivers 180 and lift the staples 190 supported thereon toward the second jaw 123. As illustrated in FIG. 20, the staple drivers 180 can progressively slide up the lift ramps 171 as the lift ramps 171 are slid thereunder. In various embodiments, the cartridge body 132 of the staple cartridge 130 can be held in place by the tissue and the second jaw 123 wherein, as a result, the staple legs 196 of the staples 190 can move relative to the cartridge body 132 when the staples 190 are lifted upwardly. In various embodiments, referring again to FIGS. 13 and 14, the cartridge body 132 can comprise a plurality of guide slots 139 which can each be configured to guide the staple legs 196 as they are moved relative to the cartridge body 132. In at least one embodiment, the guide slots 139 can be configured to closely receive the staple legs 196 such that relative movement therebetween can be limited to the upward movement described herein. As the staple legs 196 are lifted upwardly, the staple legs 196 can emerge from the cartridge body 132 through holes, or apertures, 138 defined in the cartridge body 132. In various embodiments, referring again to FIGS. 13 and 14, the cartridge body 132 can further comprise a plurality of longitudinal rails 134 in which the guide slots 139 and the apertures 138 can be defined. In at least one such embodiment, the longitudinal rails 134 can define three rows of staples 190 on a first side of a longitudinal slot 157 and three rows of staples 190 on a second side of the slot 157, for example.

As described above, the staple drivers 180 can be displaced upwardly toward the second jaw 123. In various embodiments, referring primarily now to FIG. 4A, the cartridge channel 122 of the first jaw 121 can comprise one or more features configured to guide the staple drivers 180 along a predetermined path as they are moved relative to the cartridge channel 122. In at least one embodiment, referring to FIGS. 6 and 7, each staple driver 180 can comprise a guide rail 182 which can be configured to be slidably received within a guide slot 126 defined in the outer sidewalls of the cartridge channel 122. In at least one such embodiment, the guide slots 126 can each be configured to confine the movement of a staple driver 180 along a straight line, or axis, which can be perpendicular, or at least substantially perpendicular, to the top surface 136 of the cartridge body 132, for example. In addition to or in lieu of the above, the cartridge channel 122 can further comprise one or more guide channels 127, for example, defined in the inner sidewalls of the cartridge channel 122 which can at least partially comprise cavities configured to slidably receive at least a portion of the drivers 180 therein. In various embodiments, the guide channels 127 can each be configured to confine the movement of a staple driver along a straight line which can be perpendicular, or at least substantially perpendicular, to the top surface 136 of the cartridge body 132, for example. In embodiments comprising both guide slots 126 and guide channels 127, each driver 180 can be guided on opposite sides thereof, for example.

In various embodiments, further to the above, the second jaw 123 can comprise an anvil 124 which can be configured to deform the staple legs 196 of the staples 190, as illustrated in FIGS. 20 and 21. In certain embodiments, the anvil 124 can comprise a plurality of staple pockets, for example, which can each be configured to receive at least one staple leg 196 therein and deform the staple legs 196 to a desired configuration. As the staple legs 196 are being deformed, each staple 190 can capture a portion of the tissue therein and compress the tissue against the top surface 136 of the cartridge body 132. In various embodiments, the staple legs 196 of each staple 190 can be bent inwardly toward one another and hold and/or compress the tissue captured therebetween against a bridge 195 extending between the staple leg apertures 198 defined in the cartridge body 132, for example. In certain embodiments, the staples 190 can be pushed upwardly until the bases 196 of the staples 190 are positioned adjacent to or in contact with the bridges 195. In at least one embodiment, referring primarily to FIG. 14, the cartridge body 132 can comprise a first portion including two or more rows of staples 190 and a second portion including two or more rows of staples 190, for example, wherein the first portion can be connected to the second portion by one or more connectors 156. In at least one such embodiment, the connectors 156 can extend across a longitudinal slot 157 defined in the cartridge body 132 wherein the connectors 156 can be broken and/or incised by the distal knife portion 175 as the firing member 170 is advanced distally to deploy the staples 190 and transect the tissue, as described above. After the connectors 156 have been separated, broken, or incised, the first and second portions of the cartridge body 132 may be unconnected to one another.

As illustrated in FIG. 21, the firing member 170 can be advanced distally until the distal knife portion 175 of the firing member 170 has reached the distal end of the end effector 120. At such point, in various circumstances, all of the staple drivers 180 will have been moved from their unfired positions to their fired positions, as also illustrated in FIG. 21. In certain other circumstances, the firing member 170 may not be fully advanced within the end effector 120 and only some of the staple drivers 180 may be moved upwardly from their unfired positions. In either event, the firing bar 170 can be retracted to its unactuated position after firing at least some of the staples 190. In various embodiments, referring now to FIG. 22, the distal knife portion 175 of the firing member 170 can be configured to engage the fired staple drivers 180 and return the staple drivers 180 to their unfired position as the firing bar 170 is being retracted. Referring now to FIGS. 8A and 8B, each driver 180 can further comprise a reset ramp 186 which can be engaged by a reset member 174 extending from the firing member 170. More particularly, a reset member 174 of the firing member 170 can enter into a reset cavity 184 defined in the driver 180 such that a bottom drive, or cam, surface 176 extending along the bottom side of the reset member 174 can engage the reset ramp 186 and push the reset ramp 186 downwardly, i.e., toward its unfired position. In various embodiments, the drive surface 176 and the resent ramp 186 can be oriented at the same, or at least substantially the same, angle while, in other embodiments, they may be oriented at different angles. In various other embodiments, a staple driver 180 can include any suitable surface against which the drive surface 176 can apply a force thereto. In at least one embodiment, the reset member 174 can comprise a proximal lead-in portion 174a which, in certain circumstances, can be configured to enter the reset cavity 184 before the drive surface 176 contacts the reset ramp 186. In at least one such embodiment, the proximal lead-in portion 174a can comprise a beveled surface which can initially contact the staple driver 180 and adjust the position of the staple driver 180 before the staple driver 180 is cammed downwardly by the drive surface 176. As discussed above, the movement of each staple driver 180 can be confined to a vertical path, for example, wherein each staple driver 180 can be displaced downwardly along this vertical path as the reset member 174 passes therethrough. By the time that a distal portion 174b of the reset member 174 has exited the reset cavity 184 of the staple driver 180, in various embodiments, the staple driver 180 will have been returned to its unfired position.

Referring again to FIGS. 22 and 23, the reset members 174 of the firing member 170 can initially reset the distal-most staple drivers 180 and then sequentially reset the remainder of the staple drivers 180 as the firing member 170 is retracted to its unactuated position. As the firing member 170 is being retracted, the second flange 173 of the firing member 170 can exit the longitudinal slot 103 of the second jaw 123 thereby allowing the second jaw 123 to re-open, as discussed above. Once the second jaw 123 has been sufficiently re-opened, as illustrated in FIG. 23, the first jaw 121 can be moved away from the implanted staple cartridge 130a. More particularly, as discussed above, the staples 190 can capture the cartridge body 132 against the tissue such that, when the first jaw 121 is moved away from the tissue, the cartridge body 132 can detach from the first jaw 121 and remain behind with the tissue. The disclosure of U.S. patent application Ser. No. 13/097,856, entitled STAPLE CARTRIDGE COMPRISING STAPLES POSITIONED WITHIN A COMPRESSIBLE PORTION THEREOF, filed on Apr. 29, 2011, is hereby incorporated by reference in its entirety. The disclosure of U.S. patent application Ser. No. 12/894,369, entitled IMPLANTABLE FASTENER CARTRIDGE COMPRISING A SUPPORT RETAINER, filed on Sep. 30, 2010, is also hereby incorporated by reference in its entirety. After the staple cartridge 130a has been implanted and removed from the staple cartridge channel 122, a second staple cartridge, such as staple cartridge 130b, for example, can be advanced into the staple cartridge channel 122. As described above, the firing member 170 can be retracted from its unactuated position to its lowered position such that the staple cartridge 130b can be advanced distally past the firing member 170 and into the end effector 120 by the cartridge driver 140. At such point, the reloaded surgical stapler 100 can be used once again.

After the second staple cartridge 130b has been implanted, further to the above, a third staple cartridge 130c can be advanced into the end effector 120. In fact, the illustrated embodiment of surgical stapler 100 can comprise five staple cartridges 130 positioned therein although other embodiments are contemplated which comprise less than five staple cartridges or more than five staple cartridges positioned therein. In any event, a continuous, or sequential, supply of staple cartridges 130 may allow the surgeon to repeatedly use the surgical stapler 100 without having to remove the end effector 120 from the surgical site in order to be reloaded. Stated another way, certain previous surgical staplers required the end effectors thereof to be removed from the surgical site in order to be reloaded, which increased the time needed to complete a surgical procedure. Furthermore, certain previous surgical staplers required a surgeon to remove a spent staple cartridge from the end effectors thereof in order to insert a new staple cartridge, which also increased the time needed to complete a surgical procedure. In any event, certain embodiments are contemplated herein wherein, once the supply of staple cartridges 130 contained within the shaft 110 have been exhausted, additional staple cartridges 130 can be inserted into the shaft 110 of the surgical stapler 100 such that the staple cartridges 130 can be fed into the end effector 120, as described above. Furthermore, at least one embodiment is contemplated in which a staple cartridge 130 can be manually inserted into the staple cartridge channel 122 after the supply of staple cartridges 130 contained within the surgical stapler 100 has been exhausted.

As described above, the surgical stapler 100 can be configured to supply a continuous, or sequential, number of staple cartridges 130 into the end effector 120. As also described above, the cartridge driver 140 of the surgical stapler 100 can be reciprocated between proximal and distal positions in order to sequentially advance the distal-most staple cartridge 130 contained within the shaft 110 into the cartridge channel 122. Stated another way, the cartridge driver 140 can be configured to advance a staple cartridge 130 from a staging position (FIG. 16) to a loaded position (FIG. 2) and, after the cartridge driver 140 has been returned to its proximal position and the loaded staple cartridge 130 has been implanted, the cartridge driver 140 can advance another staple cartridge 130 from the staging position to the loaded position once again. In at least one such embodiment, the cartridge driver 140 can extend over the proximal-most staple cartridges 130 such that the distal end of the cartridge 140 can directly engage the distal-most staple cartridge 130. In various embodiments, referring again to FIG. 3, the surgical instrument 100 can further comprise a biasing member 150 which can be configured to supply the staging position with another staple cartridge 130 as the staple cartridge 130 that was previously positioned in the staging position is advanced into the cartridge channel 122, as described above. In at least one such embodiment, the biasing member 150 can comprise a distal sled 151 which can be configured to contact the proximal-most cartridge 130 and, in addition, one or more push rods 152 which can be configured to transmit a biasing force to the distal sled 151. In at least one such embodiment, the biasing member 150 can comprise a spring and/or any other suitable resilient member which can be configured to apply a continuous biasing force to the proximal-most cartridge 130. Referring again to FIG. 13, the cartridge body 132 of each staple cartridge 130 can comprise alignment protrusions 137 which can be engaged by the distal sled 151 to transmit the biasing force to the cartridge body 132. In certain embodiments, the alignment protrusions 137 can define the proximal recess 131 wherein the distal sled 151 can be received within the proximal recess 131.

Figure 15:
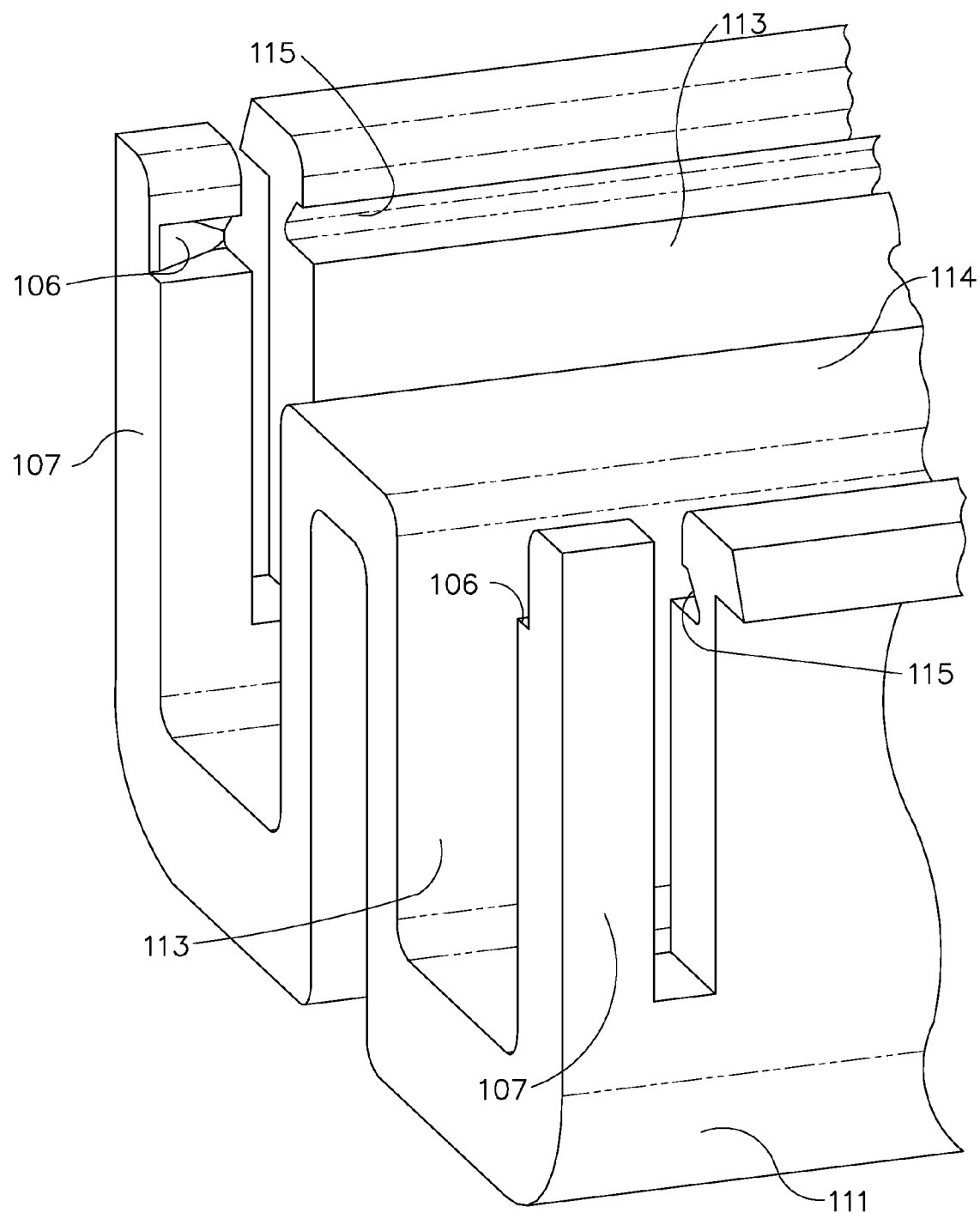
FIG. 15 is a perspective view of the distal end of the shaft of FIG. 1.

In various embodiments, further to the above, the biasing force applied to the proximal-most staple cartridge 130 by the biasing member 150 can cause the proximal-most staple cartridge 130 to slide forward and/or abut the adjacent staple cartridge 130 positioned distally thereto. With respect to FIG. 3, the biasing member 150 can apply a biasing force to the staple cartridge 130e which can abut the staple cartridge 130d and transmit the biasing force thereto. Similarly, the staple cartridge 130d can abut the staple cartridge 130c and the staple cartridge 130c can abut the staple cartridge 130b such that the biasing force is transmitted from the biasing member 150 all the way to the second staple cartridge 130b, for example. As the reader will appreciate, the biasing force being applied to the proximal-most staple cartridge 130e by the biasing member 150 tends to push all of the staple cartridges 130 distally and, specifically, tends to push the second staple cartridge 130b distally out of the staging position. In order to hold the second staple cartridge 130b, and/or any other staple cartridge 130, in the staging position until it is advanced distally by the cartridge driver 140, as described above, the shaft frame 111, for example, can comprise one or more holding members which can be configured to releasably hold a staple cartridge 130 in the staging position. Referring now to FIG. 15, the shaft frame 111 can comprise retention arms 107 which can each include a stop 106 configured to block the distal advancement of a staple cartridge 130. More particularly, the stops 106 can be aligned with the support ledges 115 such that cartridge body 132 of the staple cartridge 130 can abut the stops 106 and such that the stops 106 can releasably hold the cartridge body 132 within the support ledges 115. In at least one such embodiment, the stops 106 can define the distal end of the staging position wherein, when a staple cartridge is in contact with the stops 106, the staple cartridge 130 can be held in the staging position. In various embodiments, the retention arms 107 are sufficiently stiff to withstand and resist the biasing force being transmitted through the staple cartridges 130 by the biasing member 150, as described above. In such embodiments, however, the cartridge driver 140 is able to supply a sufficient force to the second cartridge 130b in order to dislodge it from the staging position and advance it distally. In such circumstances, the retention arms 107, and the stops 106 defined therein, can flex or move outwardly such that the second staple cartridge 130b, for example, can pass thereby. As the staple cartridge 130b is moved distally, the retention arms 107 can be engaged with the side rails 133 of the cartridge body 132 and, once the cartridge body 132 has passed by the retention arms 107, the retention arms 107 can resiliently return inwardly.

Further to the above, the reader will note that, as the second staple cartridge 130b is being advanced distally, the biasing member 150 may act to keep the third staple cartridge 130c in contact with the second staple cartridge 130b. In such circumstances, the retention arms 107 may resiliently return from their expanded position to catch the third staple cartridge 130c and hold the staple cartridge 130c in the staging position. In at least one embodiment, the cartridge body 132 of each staple cartridge may comprise a divot or recess, for example, defined in the distal ends of the side rails 133 which can provide a suitable catch for the resilient arms 107 to engage and stop a staple cartridge 130 from being prematurely advanced out of the staging position. In addition to or in lieu of the above, the side rails 133 of each cartridge body 132 may also comprise a proximal divot or recess, for example, which can allow the resilient arms 107 to resiliently return to their unflexed state prior to the subsequent staple cartridge 130 reaching its fully staged position and thereby stop the subsequent staple cartridge 130 from being advanced past the staging position. In any event, once the second staple cartridge 130b has been positioned in the end effector 120 by the cartridge driver 140, the cartridge driver 140 can be retracted to its proximal, unactuated position such that the distal end 141 of the cartridge driver 140 is positioned within the distal recess 131 of the third staple cartridge 131c. After the second cartridge 130b has been deployed, the cartridge driver 140 can advance the third staple cartridge 130c from the staging position into the end effector 120 as the biasing member 150 advances the fourth staple cartridge 130d into the staging position. Similarly, after the third cartridge 130c has been deployed, the cartridge driver 140 can advance the fourth staple cartridge 130d from the staging position into the end effector 120 as the biasing member 150 advances the fifth staple cartridge 130e into the staging position, and so forth.

As described above, a staple cartridge 130 can be slid into the end effector 120 such that the staples 190 of the staple cartridge 130 can be deployed, or fired, by the staple drivers 180. In various embodiments, the staple cartridge 130 can be advanced to a predetermined position in which the bases 197 of the staples 190 are aligned with the staple cradles 187 of the staple drivers 180. In at least one embodiment, the cartridge channel 122 can comprise a forward stop, or datum, against which the staple cartridge 130 can be positioned by the cartridge driver 140 wherein, when the cartridge body 132 is positioned against this datum, the bases 197 of the staples 190 may be aligned with the staple cradles 187. In various embodiments, the support ledges 125 defined in the sides of the cartridge channel 122 and/or the support ledges 115 defined in the shaft frame 111, for example, can define channels, slots, and/or recesses configured to closely receive the support rails 133. In at least one such embodiment, referring primarily to FIG. 14, the support ledges 115, and/or the support ledges 125, can comprise an at least partially enclosed trough which can prohibit, or at least limit, the upward movement of the cartridge body 132 relative to the shaft frame 111, and/or cartridge channel 122. In various embodiments, the troughs comprising the support ledges 125 can be configured to releasably hold the cartridge body 132 in position until the first jaw 121 is moved away from the implanted cartridge body 132, as described above. In at least one such embodiment, the cartridge body 132 can be configured to flex as the first jaw 121 is pulled away such that that support rails 133 can pop or snap out of the support ledge troughs. In various embodiments, the cartridge body 132 can be comprised of at least one bioabsorbable, biocompatible, and/or biostable plastic material, for example, which is sufficiently flexible to flex as described above.

As described above, the surgical instrument 100 can comprise a plurality of staple cartridges 130a-130e, for example, stored therein which can be consecutively or sequentially supplied to the end effector 120 thereof. In various embodiments, the staple cartridges 130a-130e, for example, can be identical, or at least substantially identical. In at least one embodiment, the staples 190 of the staple cartridges 130a-130e can each be comprised of a wire having the same, or at least substantially the same, diameter, for example. In various embodiments, this wire can be comprised of at least one metal, such as stainless steel and/or titanium, for example. The staples 190 of staple cartridges 130a-130e can also be comprised of wires having the same, or at least substantially the same, length, for example. In various embodiments, the staples 190 of staple cartridges 130a-130e can have the same, or at least substantially the same, overall unformed height. In at least one such embodiment, the overall unformed height of a staple 190 can be defined as the distance between the bottom surface of its base 197 and the tips of its staple legs 196. In at least one embodiment, the staple legs 196 can have the same, or at least substantially the same, length, i.e., the distance between the top surface of the staple base 197 and the tips of the staple legs 196. In any event, the surgical stapler 100 can be configured to supply consecutive identical, or nearly identical, staple cartridges 130 to the end effector 120, in various embodiments.

In various other embodiments, one or more of the staple cartridges stored within the surgical stapler 100 can be different than the other staple cartridges stored within the surgical stapler 100 in at least one regard. In at least one such embodiment, one or more of the staple cartridges stored within the surgical stapler 100 can comprise staples having at least one different diameter. For example, a first staple cartridge stored within the surgical stapler can comprise a plurality of first staples comprised of wires having a first diameter, a second staple cartridge stored within the surgical stapler can comprise a plurality of second staples comprised of wires having a second diameter, and a third staple cartridge stored within the surgical stapler can comprise a plurality of third staples comprised of wires having a third diameter, wherein the first diameter can be different than the second diameter, the second diameter can be different than the third diameter, and the first diameter can be different than the third diameter. In certain embodiments, a staple cartridge can comprise a first row of staples comprised of wires having a first diameter, a second row of staples comprised of wires having a second diameter, and/or a third row of staples comprised of wires having a third diameter, wherein the first diameter can be different than the second diameter, the second diameter can be different than the third diameter, and the first diameter can be different than the third diameter, for example. In certain embodiments, one or more of the staple cartridges stored within the surgical stapler 100 can comprise staples having at least one different unformed height. For example, a first staple cartridge stored within the surgical stapler can comprise a plurality of first staples having a first height, a second staple cartridge stored within the surgical stapler can comprise a plurality of second staples having a second height, and a third staple cartridge stored within the surgical stapler can comprise a plurality of third staples having a third height, wherein the first height can be different than the second height, the second height can be different than the third height, and the first height can be different than the third height. In certain embodiments, a staple cartridge can comprise a first row of staples having a first height, a second row of staples having a second height, and/or a third row of staples having a third height, wherein the first height can be different than the second height, the second height can be different than the third height, and the first height can be different than the third height, for example. In certain embodiments, one or more of the staple cartridges stored within the surgical stapler 100 can comprise staples having at least one different unformed leg length. For example, a first staple cartridge stored within the surgical stapler can comprise a plurality of first staples having a first leg length, a second staple cartridge stored within the surgical stapler can comprise a plurality of second staples having a second leg length, and a third staple cartridge stored within the surgical stapler can comprise a plurality of third staples having a third leg length, wherein the first leg length can be different than the second leg length, the second leg length can be different than the third leg length, and the first leg length can be different than the third leg length. In certain embodiments, a staple cartridge can comprise a first row of staples having a first leg length, a second row of staples having a second leg length, and/or a third row of staples having a third leg length, wherein the first leg length can be different than the second leg length, the second leg length can be different than the third leg length, and the first leg length can be different than the third leg length, for example.

In various embodiments, further to the above, the staple cartridges 130 contained within the surgical stapling instrument can comprise different cartridge bodies. For example, the cartridge body of a first staple cartridge 130 can have a first thickness while the cartridge body of a second staple cartridge 130 can have a second thickness which is different than the first thickness. In at least one such embodiment, the second thickness can be thicker than the first thickness, for example. In certain embodiments, the cartridge body of a first staple cartridge 130 can be comprised of a first material while the cartridge body of a second staple cartridge 130 can be comprised of a second material which is different than the first material. In at least one such embodiment, the second material can be more flexible than the first material, for example.

In various embodiments, the different staple cartridges can be loaded into the shaft 110 in a predetermined order such that the staple cartridges are utilized according to a predetermined sequence. In at least one such embodiment, a surgical procedure may require the surgical instrument to staple and transect a first portion of stomach tissue having a first thickness and then a second portion of stomach tissue having a thicker thickness wherein, in such circumstances, the first staple cartridge can comprise staples having a shorter unformed height than the staples contained within the second staple cartridge, for example. Such circumstances may arise when performing a Rouen-Y surgical technique, for example.

In various alternative embodiments, further to the above and referring again to FIGS. 9 and 10, the top surfaces of reset members 174 can comprise drive surfaces which can be configured to engage the staple drivers 180. In at least one such embodiment, referring now to FIGS. 6 and 7, each staple driver 180 can comprise a drive surface 183 which can be engaged by the top surfaces of the reset members 174 as the firing member 170 is advanced distally in order to displace the staple drivers 180, and the staples 190 supported thereon, upwardly. In at least one embodiment, the top surfaces of the reset members 174 can define inclined lifting surfaces which can be parallel, or at least substantially parallel, to the bottom lowering surfaces 176. In certain embodiments, as a result of the above, the reset members 174 can comprise a ramp which includes a top surface which lifts the staple drivers 180 and a bottom surface which lowers the staple drivers 180. In various embodiments, the reset members 174 can be configured such that the ends 174a and 174b of each reset member 174 are positioned distally with respect to the cutting edge of the distal knife portion 175. In at least one such embodiment, the staples can be formed to their fully fired height, or at least substantially fully fired height, before the cutting edge passes through and incises the stapled portion of the tissue. In various embodiments, referring again to FIGS. 9 and 10, the distal knife portion 175 of the firing member 170 can comprise a bottom surface 177 which can be configured to slide along a bottom surface of the staple cartridge channel 122. In at least one such embodiment, the first jaw 121 can further comprise a lead-in 108 (FIG. 4A) including a radiused and/or beveled edge, for example, which can be configured to guide the bottom surface 177 into the cartridge channel 122, especially after the distal knife portion 175 has been moved into its lowered position, for example.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A surgical stapling instrument, comprising:
    a handle comprising a trigger;
    a shaft extending distally from said handle;
    a firing member operably coupled with said trigger such that a firing motion can be transferred from said trigger to said firing member to move said firing member along a firing path;
    a first staple cartridge positioned within said shaft, wherein said first staple cartridge comprises:
        a first cartridge body comprising a plurality of first apertures positioned in a first longitudinal row; and
        a plurality of first staples each comprising at least one first staple leg positioned in a said first aperture, wherein said first staple legs are slidable within said first apertures, and wherein said first staple legs comprise a first length;
    a staged second staple cartridge positioned within said shaft behind said first staple cartridge, wherein said second staple cartridge comprises:
        a second cartridge body comprising a plurality of second apertures positioned in a second longitudinal row, wherein said second longitudinal row is longitudinally aligned with said first longitudinal row; and
        a plurality of second staples each comprising at least one second staple leg positioned in a said second aperture, wherein said second staple legs are longitudinally aligned with said first staple legs, wherein said second staple legs are slidable within said second apertures, and wherein said second staple legs comprise a second length which is different than said first length of said longitudinally aligned first staple legs thereby making said second staple cartridge different than said first staple cartridge;
    a first jaw comprising a channel configured to receive a said staple cartridge;
    a second jaw comprising an anvil configured to deform said staples; and
    a cartridge driver configured to sequentially advance said first and second staple cartridges into said channel from a staging position.

2. The surgical stapling instrument of claim 1, wherein said first staple cartridge is positioned in said staging position, and wherein said second staple cartridge is positioned proximally with respect to said first staple cartridge.

3. The surgical stapling instrument of claim 2, wherein said second length is longer than said first length.

4. The surgical stapling instrument of claim 2, further comprising a third staple cartridge positioned within said shaft, wherein said third staple cartridge comprises:
    a third cartridge body comprising a plurality of third apertures; and
    a plurality of third staples each comprising at least one third staple leg positioned in a said third aperture, wherein said third staple legs are slidable within said third apertures, and wherein said third staple legs comprise a third length which is different than said first length and said second length.

5. The surgical stapling instrument of claim 1, wherein said first staple cartridge comprises at least one inner row of first staples and at least one outer row of staples comprising a length different than said first length, and wherein said second staple cartridge comprises at least one inner row of second staples and at least one outer row of staples having a length different than said second length.

6. The surgical stapling instrument of claim 1, wherein said first staple cartridge comprises at least one inner row of first staples and at least one outer row of staples comprising a length greater than said first length, and wherein said second staple cartridge comprises at least one inner row of second staples and at least one outer row of staples comprising a length different than said second length.

7. The surgical stapling instrument of claim 1, wherein said first staples are each comprised of wire having a first diameter, and wherein said second staples are each comprised of wire having a second diameter different than said first diameter.

8. A surgical stapling instrument assembly, comprising:
    a shaft comprising a removable magazine;
    a firing member movable along a firing path;
    a first staple cartridge positioned within said magazine, wherein said first staple cartridge comprises:
        a first cartridge body comprising a plurality of first apertures positioned in a first longitudinal row; and
        a plurality of first staples each comprising a first staple leg positioned in a said first aperture, wherein said first staple legs are slidable within said first apertures, and wherein said first staples each comprise a first height;
    a staged second staple cartridge positioned behind said first staple cartridge within said magazine, wherein said second staple cartridge comprises:
        a second cartridge body comprising a plurality of second apertures positioned in a second longitudinal row, wherein said second longitudinal row is longitudinally aligned with said first longitudinal row; and a plurality of second staples each comprising a second staple leg positioned in a said second aperture, wherein said second staple legs are longitudinally aligned with said first staple legs, wherein said second staple legs are slidable within said second apertures, and wherein said second staples comprise a second height which is different than said first height of said longitudinally aligned first staple legs thereby making said second staple cartridge different than said first staple cartridge;

a first jaw comprising a channel configured to receive a said staple cartridge;

a second jaw comprising an anvil configured to deform said staples; and a cartridge driver configured to sequentially advance said first and second staple cartridges into said channel from a staging position.

9. The surgical stapling instrument assembly of claim 8, wherein said first staple cartridge is positioned in said staging position, and wherein said second staple cartridge is positioned proximally with respect to said first staple cartridge.

10. The surgical stapling instrument assembly of claim 9, wherein said second height is greater than said first height.

11. The surgical stapling instrument assembly of claim 9, further comprising a third staple cartridge positioned within said magazine, wherein said third staple cartridge comprises:
a third cartridge body comprising a plurality of third apertures; and
a plurality of third staples each comprising a third staple leg positioned in a said third aperture, wherein said third staple legs are slidable within said third apertures, and wherein said third staples comprise a third height which is different than said first height and said second height.

12. The surgical stapling instrument assembly of claim 8, wherein said first staple cartridge comprises at least one inner row of first staples and at least one outer row of staples comprising a height different than said first height, and wherein said second staple cartridge comprises at least one inner row of second staples and at least one outer row of staples having a height different than said second height.

13. The surgical stapling instrument assembly of claim 8, wherein said first staple cartridge comprises at least one inner row of first staples and at least one outer row of staples comprising a height greater than said first height, and wherein said second staple cartridge comprises at least one inner row of second staples and at least one outer row of staples comprising a height different than said second height.

14. The surgical stapling instrument assembly of claim 8, wherein said first staples are each comprised of wire having a first diameter, and wherein said second staples are each comprised of wire having a second diameter different than said first diameter.

15. A surgical stapling instrument, comprising:
a shaft;
a firing member movable along a firing path;
a first staple cartridge positioned within said shaft, wherein said first staple cartridge comprises a first cartridge body and a plurality of first staples arranged in a first longitudinal row, wherein said first staples each comprise a first height;
a staged second staple cartridge positioned within said shaft behind said first staple cartridge, wherein said second staple cartridge comprises a second cartridge body and a plurality of second staples arranged in a second longitudinal row, wherein said second longitudinal row is longitudinally aligned with said first longitudinal row, wherein said second staples are longitudinally aligned with said first staples, and wherein said second staples each comprise a second height which is different than said first height of said longitudinally aligned first staples thereby making said second staple cartridge different than said first staple cartridge;
a first jaw comprising a channel configured to receive a said staple cartridge;
a second jaw comprising an anvil configured to deform said staples; and
a cartridge driver configured to sequentially advance said first and second staple cartridges into said channel.

16. The surgical stapling instrument of claim 15, wherein said second height is greater than said first height.

17. The surgical stapling instrument of claim 15, further comprising a third staple cartridge comprising a third cartridge body and a plurality of third staples each comprising a third height which is different than said first height and said second height.

18. The surgical stapling instrument of claim 15, wherein said first staple cartridge comprises at least one inner row of first staples and at least one outer row of staples comprising a height different than said first height, and wherein said second staple cartridge comprises at least one inner row of second staples and at least one outer row of staples having a height different than said second height.

19. The surgical stapling instrument of claim 15, wherein said first staple cartridge comprises at least one inner row of first staples and at least one outer row of staples comprising a height greater than said first height, and wherein said second staple cartridge comprises at least one inner row of second staples and at least one outer row of staples comprising a height different than said second height.

20. The surgical stapling instrument of claim 15, wherein said first staples are each comprised of wire having a first diameter, and wherein said second staples are each comprised of wire having a second diameter different than said first diameter.

* * * * *